(12) United States Patent
Labrie

(10) Patent No.: US 11,576,891 B2
(45) Date of Patent: Feb. 14, 2023

(54) METHODS OF TREATING OR PREVENTING ESTROGEN-RELATED DISEASES

(75) Inventor: Fernand Labrie, Québec (CA)

(73) Assignee: ENDORECHERCHE, INC.

( * ) Notice: Subject to any disclaimer, the term of this patent is extended or adjusted under 35 U.S.C. 154(b) by 0 days.

(21) Appl. No.: 13/162,486

(22) Filed: Jun. 16, 2011

(65) Prior Publication Data

US 2011/0312925 A1    Dec. 22, 2011

Related U.S. Application Data

(60) Provisional application No. 61/355,465, filed on Jun. 16, 2010.

(51) Int. Cl.
| | |
|---|---|
| A61K 31/35 | (2006.01) |
| A61K 31/56 | (2006.01) |
| A61K 31/453 | (2006.01) |
| A61K 45/06 | (2006.01) |
| A61P 5/04 | (2006.01) |
| A61P 5/24 | (2006.01) |
| A61P 5/30 | (2006.01) |
| A61P 15/08 | (2006.01) |
| A61P 15/00 | (2006.01) |
| A61P 15/02 | (2006.01) |
| A61P 25/28 | (2006.01) |
| A61P 25/06 | (2006.01) |
| A61P 35/00 | (2006.01) |

(52) U.S. Cl.
CPC ............ *A61K 31/35* (2013.01); *A61K 31/453* (2013.01); *A61K 31/56* (2013.01); *A61K 45/06* (2013.01); *A61P 5/04* (2018.01); *A61P 5/24* (2018.01); *A61P 5/30* (2018.01); *A61P 15/00* (2018.01); *A61P 15/02* (2018.01); *A61P 15/08* (2018.01); *A61P 25/06* (2018.01); *A61P 25/28* (2018.01); *A61P 35/00* (2018.01)

(58) Field of Classification Search
CPC ...... A61K 31/35; A61K 31/453; A61K 31/56; A61K 45/06; A61P 5/04; A61P 5/24; A61P 5/30; A61P 15/02; A61P 15/08; A61P 15/00
See application file for complete search history.

(56) References Cited

U.S. PATENT DOCUMENTS

| | | | |
|---|---|---|---|
| 3,742,951 A | 7/1973 | Zaffaroni | |
| 3,797,444 A | 3/1974 | Stubbs | |
| 4,024,248 A | 5/1977 | Konig et al. | |
| 4,100,274 A | 7/1978 | Dutta et al. | |
| 4,118,483 A | 10/1978 | König et al. | |
| 4,481,190 A | 11/1984 | Nestor et al. | |
| 4,568,343 A | 2/1986 | Leeper et al. | |
| 4,624,665 A | 11/1986 | Nuwayser | |
| 4,666,441 A | 5/1987 | Andriola et al. | |
| 5,071,644 A | 10/1991 | Viegas et al. | |
| 5,064,654 A | 11/1991 | Berner et al. | |
| 5,071,657 A | 12/1991 | Oloff et al. | |
| 5,135,480 A | 8/1992 | Bannon et al. | |
| 5,154,922 A | 10/1992 | Govil et al. | |
| 5,162,037 A | 11/1992 | Whitson-Fischman | |
| 5,204,337 A | 4/1993 | Labrie et al. | 514/182 |
| 5,393,785 A | 2/1995 | Labrie et al. | 514/622 |
| 5,395,842 A | 3/1995 | Labrie et al. | 514/320 |
| 5,484,797 A | 1/1996 | Bryant et al. | 514/319 |
| 5,550,107 A | 8/1996 | Labrie | 514/11 |
| 5,567,828 A | 10/1996 | Dodge | 549/51 |
| 5,889,042 A | 3/1999 | MacLean et al. | |
| 6,281,205 B1 | 8/2001 | Tanabe et al. | |
| 6,710,059 B1 | 3/2004 | Labrie et al. | |
| 7,309,691 B2 | 12/2007 | Stockemann et al. | 514/16 |
| 8,518,890 B2 | 8/2013 | Hara et al. | |
| 2001/0041672 A1 | 11/2001 | Stockemann et al. | 514/16 |
| 2004/0110689 A1* | 6/2004 | Garnick | A61K 38/09 514/10.2 |
| 2004/0259915 A1 | 12/2004 | Kanojia et al. | |
| 2005/0159361 A1* | 7/2005 | Hara | A61P 43/00 514/19.5 |

(Continued)

FOREIGN PATENT DOCUMENTS

| | | |
|---|---|---|
| CA | 2244675 | 8/1997 |
| CA | 2 334 577 A1 | 12/1999 |
| CA | 2 458 452 A1 | 2/2003 |

(Continued)

OTHER PUBLICATIONS

International Search Report dated Sep. 2, 2011 in corresponding International Application No. PCT/CA2011/000709.
Written Opinion dated Sep. 2, 2011 in corresponding International Application No. PCT/CA2011/000709.
Pickersgill, "GnRH agonists and add-back therapy: is there a perfect combination?," British Journal of Obstetrics and Gynecology, (May 1998), vol. 105, pp. 475-485.
Pelletier, et al., "Role of Extra-Ovarian Oestrogens in the Regulation of Gonadotropin Releasing Hormone mRNA Expression in the Rat Brain," Journal of Neuroendocrinology, (2001), vol. 13, pp. 678-682.

(Continued)

*Primary Examiner* — Kara R McMillian
(74) *Attorney, Agent, or Firm* — Ostrolenk Faber LLP

(57) ABSTRACT

Methods for treating or reducing the likelihood of acquiring estrogen-related (e.g. estrogen-exacerbated) diseases including endometriosis include administering to a patient a selective estrogen receptor modulator (SERM), in combination with inhibiting ovarian secretions, e.g., by administering an LHRH agonist or antagonist. In some embodiments, a precursor of sex steroids, said precursor being selected from the group consisting of dehydroepiandrosterone (DHEA), dehydroepiandrosterone sulfate (DHEA-S), androst-5-ene-3β,17β-diol (5 diol), and androstenedione or a compound transformed into one of these, is also administered.

1 Claim, 11 Drawing Sheets

(56) References Cited

U.S. PATENT DOCUMENTS

2005/0215528 A1    9/2005    Furuya et al.

FOREIGN PATENT DOCUMENTS

| | | |
|---|---|---|
| CA | 2 478 827 A1 | 9/2003 |
| EP | 0 058 481 A1 | 8/1982 |
| EP | 0 279 982 A1 | 8/1988 |
| EP | 0 652 005 A1 | 5/1995 |
| EP | 0 703 228 A1 | 3/1996 |
| EP | 0 729 951 A1 | 9/1996 |
| EP | 0 731 093 A1 | 9/1996 |
| EP | 0 761 669 A2 | 3/1997 |
| EP | 0 802 183 A1 | 10/1997 |
| EP | 2004-2321 | 1/2004 |
| EP | 1 424 080 A1 | 6/2004 |
| EP | 1 488 807 A1 | 12/2004 |
| GB | 2 185 187 A | 7/1987 |
| GB | 2 303 628 A | 2/1997 |
| JP | 10-036347 A | 2/1998 |
| JP | 2002-517433 | 6/2002 |
| JP | 2003-137814 | 5/2003 |
| KR | 10-1999-0082080 | 11/1999 |
| WO | WO 9609040 A1 | 3/1996 |
| WO | WO 9609041 A1 | 3/1996 |
| WO | WO 96/26201 | 8/1996 |
| WO | WO 97/04763 | 2/1997 |
| WO | WO 97/25034 | 7/1997 |
| WO | WO 97/25035 | 7/1997 |
| WO | WO 97/25036 | 7/1997 |
| WO | WO 97/25037 | 7/1997 |
| WO | WO 97/25038 | 7/1997 |
| WO | WO 97/27863 | 8/1997 |
| WO | WO 97/32837 | 9/1997 |
| WO | WO 98/07740 | 2/1998 |
| WO | WO 99/63973 A2 | 12/1999 |
| WO | WO 99/63974 | 12/1999 |
| WO | WO 01/68634 A1 | 9/2001 |
| WO | WO 02/056903 A2 | 7/2002 |
| WO | WO 03/015820 A1 | 2/2003 |
| WO | WO 03/017973 A1 | 3/2003 |
| WO | WO 03/017974 A1 * | 3/2003 |
| WO | WO 03/045972 A1 | 6/2003 |
| WO | WO 03/075958 A1 | 9/2003 |
| WO | WO 2004/009086 A1 | 1/2004 |
| WO | WO 2005/073190 A1 | 8/2005 |
| WO | WO 2005/073205 A1 | 8/2005 |
| WO | WO 2005/073206 A1 | 8/2005 |
| WO | WO 2005/073244 A1 | 8/2005 |
| WO | WO 2006/042409 A1 | 4/2006 |

OTHER PUBLICATIONS

Labrie, "Future perspectives of selective estrogen receptor modulators used alone and in combination with DHEA," Endocrine-Related Cancer, (2006), vol. 13, pp. 335-355.
International Preliminary Report on Patentability dated Jan. 3, 2013 containing Written Opinion of the International Searching Authority dated Sep. 2, 2011 in corresponding International Application No. PCT/CA2011/000709.
Ailawadi, R. K., S. Jobanputra, M. Kataria, B. Gurates and S. E. Bulun (Feb. 2004) "Treatment of endometriosis and chronic pelvic pain with letrozole and norethindrone acetate: a pilot study." Fertil Steril 81(2): 290-6.
Allen, L. V. with the contributions by D. B. Worthen and B. Mink (2008). Suppository bases and their characteristics (Chapter 3). Suppositories. Pharmaceutical Press, London, UK: 27-49.
Auclair, C., P. A. Kelly D. H. Coy, A. V. Schally and F. Labrie (1977). "Potent inhibitory activity of [D-Leu$^6$, des-Gly-NH$_2$ $^{10}$] ethylamide on LH/hCG and PRL testicular receptor levels in the rat." Endocrinology 101: 1890-1893.
Auclair, C., P. A. Kelly, F. Labrie, D. H. Coy and A. V. Schally (1977). "Inhibition of testicular luteinizing receptor level by treatment with a potent luteinizing hormone-releasing hormone agonist of human chorionic gonadotropin." Biochem. Biophys. Res. Commun. 76: 855-862.
Auclair, C., L. Ferland, L. Cusan, P. A. Kelly, F. Labrie, G. Azadian-Boulanger and J. P. Raynaud (1978). "Effet inhibiteur de la LHRH sur les récepteurs de la LH dans le testicule chez le rat." C.R. Acad. Sci. Paris, Série D 286: 1305-1307.
Barbieri, R. (Feb. 1992). "Hormone treatment of endometriosis: the estrogen threshold hypothesis." Am. J. Obstet. Gynecol. 166: 740-745.
Bardon, S., F. Vignon, D. Chalbos and H. Rochefort (1985). "RU486, a progestin and glucocorticoid antagonist, inhibits the growth of breast cancer cells via the progesterone receptor." J. Clin. Endocrinol. Metab. 60: 692-697.
Baxendale, P. M., M. J. Reed and V. H. James (1981). "Inability of human endometrium or myometrium to aromatize androstenedione." J Steroid Biochem 14(3): 305-6.
Bélanger, A., C. Auclair, C. Séguin, P. A. Kelly and F. Labrie (1979). "Down-regulation of testicular androgen biosynthesis and LH receptor levels by an LHRH agonist, role of prolactin." Mol. Cell. Endocrinol. 13: 47-53.
Bélanger, A., F. Labrie, A. Lemay, S. Caron and J. P. Raynaud (1980). "Inhibitory effects of a single intranasal administration of [D-Ser(TBU)6, des-Gly-NH210]LPIRH agonist, a potent LHRH agonist, on serum steroid levels in normal adult men." J. Steroid Biochem. 13: 123-126.
Black, L. J., M. Sato, E. R. Bowley, D. E. Magee, A. Bekele, D. C. Williams, G. J. Cullinan, R. Bendele, R. F. Kaufman, W. R. Bensch, C. A. Frolik, J. D. Termine and H. U. Bryant (1994). "Raloxifene (LY139481 HCl) prevents bone loss and reduces serum cholesterol without causing uterine hypertrophy in ovariectomized rats." J. Clin. Invest. 93: 63-69.
Bulun, S. E., S. Yang, Z. Fang, B. Gurates, M. Tamura J. Zhou and S. Sebastian (2001). "Role of aromatase in endometrial disease." J Steroid Biochem Mol Biol 79(1-5): 19-25.
Bulun, S. E., Z. Lin, G. Imir, S. Amin, M. Demura, B. Yilmaz, R. Martin, H. Utsunomiya, S. Thung, B. Gurates, M. Tamura, D. Langoi and S. Deb (2005). "Regulation of aromatase expression in estrogen-responsive breast and uterine disease: from bench to treatment." Pharmacol Rev 57(3): 359-83.
Burger, H. G., J. Hailes, M. Menelaus, J. Nelson, B. Hudson and N. Balazs (1984). "The management of persistent menopausal symptoms with oestradiol-testosterone implants: clinical, lipid and hormonal results." Maturitas 6: 351-358.
Casson P. R., R. N. Andersen H. G. Herrod, F. B. Stentz, A. B. Straughn, G. E. Abraham and J. E. Buster (Dec. 1993). "Oral dehydroepiandrosterone in physiologic doses modulates immune function in postmenopausal women", Am. J. Obstet. Gynecol. 169: 1536-1539.
Cedars, M., J. Lu, D. Meldrum and H. Judd (Apr. 1990). "Treatment of endometriosis with a long-acting gonadotropin-releasing hormone agonist plus medroxyprogesterone acetate." Obstet. Gynecol. 5: 641-645.
Colditz, G. A., S. E. Hankinson, D. J. Hunter, W. C. Willett, J. E. Manson, M. J. Stampfer, C. Hennekens, B. Rosner and F. E. Speizer (Jun. 15, 1995). "The use of estrogens and progestins and the risk of breast cancer in postmenopausal women." N. Engl. J. Med. 332: 1589-1593.
Coleman, D. L., E. H. Leiter and R. W. Schwizer (Sep. 1982). "Therapeutic effects of dehydroepiandrosterone (DHEA) in diabetic mice." Diabetes 31: 830-833.
Conley G. Lacey, (1984). "Disorders of the Uterine Corpus", Current Obstetric and Gynecologic Diagnosis and Treatment. Lange Medical Publications: 258-263.
Corbin, A., F. J. Bex and R. C. Jones (1984): "Comparison of LHRH agonist (AG) and antagonist (ANT): antifertility and therapeutic developments." J. Steroid Biochem. 20 (6B)(1369): A9.
Couillard, S., M. Gutman, C. Labrie, A. Bélanger, B. Candas and F. Labrie (1998). "Comparison of the effects of the antiestrogens EM-800 and Tamoxifen on the growth of human breast ZR-75-1 cancer xenografts in nude mice." Cancer Res. 58: 60-64.
Couillard, S., C. Labrie, A. Bélanger, B. Candas, F. Pouliot and F. Labrie (1998. "Effect of dehydroepiandrosterone and the antiestrogen

(56) References Cited

OTHER PUBLICATIONS

EM-800 on the growth of human ZR-75-1 breast cancer xenografts." J. Natl. Cancer Inst. 90, Reports 772-778.

Coy, D. H., A. Horvath, M. V. Nekola, E. J. Coy, J. Erchegyi and A. V. Schally (1982). "Peptide antagonists of LHRH: large increases in antiovulatory activities produced by basic D-amino acids in the six position." Endocrinology 110: 1445-1447.

Diamond, P., L. Cusan, J. L. Gomez, A. Bélanger and F. Labrie (1996). "Metabolic effects of 12-month percutaneous DHEA replacement therapy in postmenopausal women." J. Endocrinol. 150: S43-S50.

Dizerega, S. G., D. L. Barber and G. D. Hodgen .(1980). "Endometriosis: role of ovarian steroids in initiation, maintenance, and suppression." Fertil. Steril. 33: 649-653.

Draper, M. W., D. E. Flowers, J. A. Neild, W. J. Huster and R. L. Zerbe (1995). "Antiestrogenic properties of raloxifene." Pharmacology 50(4): 209-217.

Draper, M. W., D. E. Flowers, W. J. Huster, J. A. Neild, K. D. Harper and C. Arnaud. (1996). "A controlled trial of raloxifene (LY139481) HCl: impact on bone turnover and. serum lipid profile in healthy postmenopausal women." J. Bone Miner. Res. 11(6): 835-842.

Dutta, A. S., B. J. A. Furr, M. B. Giles and B. Valcaccia (1978). "Synthesis and biological activity of highly active a-aza analogues of luliberin." J. Med. Chem. 21(10): 1018-1024.

Eldred J., P. Haynes and C. Thomas (1992). "A randomized double-blind placebo controlled trial of the effects of bone metabolism of the combination of nafarelin acetate and norethisterone." Clin. Endocrinol. 37: 354-359.

Erchegyi, J., D. H. Coy, M. V. Nekola, E. J. Coy, A. V. Schally, I. Mezo and I. Teplan (1981). "Luteinizing. hormone-releasing hormone analogs with increased activity." Biochem. Biophys. Res. Commun. 100: 915-920.

Erickson, L. D. and S. J. Ory (1989). "GnRH analogues in the treatment of endometriosis." Obstet. Gynecol. Clin. North Am. 16: 23-45.

Fang, Z., S. Yang, B. Gurates, M. Tamura, E. Simpson, D. Evans and S. E. Bulun (2002). "Genetic or enzymatic disruption of aromatase inhibits the growth of ectopic uterine tissue." J Clin Endocrinol Metab 87(7): 3460-6.

Fogelman, I. (1992). "Gonadotropin-releasing hormone agonists and the skeleton." Fertil. Steril. 57: 715-724.

Friedman, A. J. (Mar. 1989). "Treatment of leiomyomata uteri with short-term leuprolide followed by leuprolide plus estrogen-progestin hormone replacement therapy for 2 years: a pilot study." Fertil. Steril. 51: 526-528.

Gauthier, S., B. Caron, J. Cloutier, Y. L. Dory, A. Favre, D. Larouche, J. Mailhot, C. Ouellet, A. Schwerdtfeger, G. Leblanc, C. Martel, J. Simard, Y. Merand, A. Bélanger, C. Labrie and F. Labrie (1997). "(S)7(+)-4-[7-(2,2-dimethyl-1-oxopropoxy)-4-methyl-2-[4-[2-(1-piperidinyl)-ethoxylphenyl]-2H-1-benzopyran-3-yl]-phenyl 2,2-dimethylpropanoate (EM-800): a highly potent, specific, and orally active nonsteroidal antiestrogen." J. Med. Chem. 40: 2117-2122.

Gordon, G. B., L. M. Shantz and P. Talalay (1987). "Modulation of growth, differentiation and carcinogenesis by dehydroepiandrosterone." Adv. Enzyme Regul. 26: 355-382.

Goulding, A. and L. Fisher (1991). "Preventive effects of clomiphene citrate on estrogen-deficiency osteopenia elicited by LHRH agonist administration in the rat." J. Bone Miner. Res. 6(11): 1177-81.

Gurates, B., S. Sebastian, S. Yang, J. Zhou, M. Tamura, Z. Fang, T. Suzuki, H. Sasano and S. E. Bulun (2002). "WT1 and DAX-1 inhibit aromatase P450 expression in human endometrial and endometriotic stromal cells." J Clin Endocrinol Metab 87(9): 4369-77.

Henderson, E. J. Y. Yang and A. Schwartz (1992). "Dehydroepiandrosterone (DHEA) and sysnthetic DHEA analogs are modest inhibitors of HIV-1 IIIB replication." Aids Res. Hum. Retroviruses 8: 625-631.

Henneman, P. H. and S. Wallach (1957). "The use of androgens and estrogens and their metabolic effects. A review of the prolonged use of estrogens and androgens in postmenopausal and senile osteoporosis." AMA: Arch. Int. Med. 100: 715-723.

Henzl, M. R., S. L. Corson, K. Moghissi, V. C. Buttram, C. Bergvist and J. Jacobson (1988). "Administration of Nasal Nafarelin as Compared With Oral Danazol for Endometriosis: A Multicentre Double-Blind comparative Trial." N. Engl. J. Med. 318: 485-489.

Jankowski, C. M., W. S. Gozansky, R. S. Schwartz D. J. Dahl, J. M. Kittelson, S. M. Scott, R. E. Van Pelt and W. M. Kohrt (2006). "Effects of dehydroepiandrosterone replacement therapy on bone mineral density in older adults: a randomized, controlled trial." J Clin Endocrinol Metab 91(8): 2986-93.

Johnston Jr, C. C. and S. Epstein (1981). "Clinical, biochemical, radiographic, epidemiologic, and economic features of osteoporosis." Orthop. Clin. North. Am. 12: 539-569.

Jones, H. W. and G. S. Jones (1981). Novak's, Textbook of Gynecology. Tenth Edition Baltimore, Williams and Wilkins: 609-635.

Kauffman, R. F. and H. U. Bryant (1995). "Effective therapeutic management of the postmenopausal state will be a cornerstone in strategies for preserving or improving women's health in the 21st century." Drug News and Perspectives 8: 531-539.

Kistner, R. W. (1959). "The treatment of endometriosis by inducing pseudopregnancy with ovarian hormones: a report of fifty-eight cases." Fertil. Steril. 10: 539-556.

Kistner, R. W. (1962). "Infertility with endometriosis: a plan of therapy." Fertil. Steril. 13: 237-245.

Kistner, R. W. (1979). "Endometriosis and infertility." Clin. Obstet. Gynecol. 22: 101-119.

Kitawaki, J., T. Noguchi, T. Amatsu, K. Maeda, K. Tsukamoto, T. Yamamoto, S. Fushiki, Y. Osawa and H. Honjo (1997). "Expression of aromatase cytochrome P450 protein and messenger ribonucleic acid in human endometriotic and adenomyotic tissues but not in normal endometrium." Biol Reprod 57(3): 514-9.

Kledzik, G. S., L. Cusan, C. Auclair, P. A. Kelly and F. Labrie (Sep. 1978). "Inhibition of ovarian LH and FSH receptor levels with an LH-releasing hormone agonist during the estrous cycle in the rat." Fertil. Steril. 30: 348-353.

Labrie, C., A. Bélanger and F. Labrie (1988). "Androgenic Activity of Dehydroppiandrosterone and Androstenedione in the Rat Ventral Prostate." Endocrinology 123: 1412-1417.

Labrie, F. (1991). "Intracrinology." Mol. Cell. Endocrinol. 78: C113-C118.

Labrie, F., J. Simard, V. Luu-The, A. Bélanger and G. Pelletier (1992a). "Structure, Function and Tissue-specific Gene Expression of 3β-hydroxysteroid Dehydrogenase/5-ene-4-ene Isomerase Enzymes in Classical and Peripheral Intracrine Steroidogenic Tissues." J. Steroid Biochem. Mol. Biol. 43: 805-826.

Labrie, F., J. Simard, V. Luu-The, G. Pelletier, A. Bélanger Y. Lachance, H. F. Zhao, C. Labrie, N. Breton, Y. de Launoit, M. Dumont, E. Duonf, E. Rheaume, C. Martel, J. Couet and C. Trudel (1992b). "Structure and Tissue-specific Expression of 3β-hydroxysteroid Dehydrogenase/5-ene-4-ene Isomerase Genes in Human and Rat Classical and Peripheral Steroidogenic Tissues." J. Steroid Biochem. Mol. Biol. 41: 421-435.

Labrie, F., J. Simard, V. Luu-The, A. Bélanger, G. Pelletier, Y. Morel, F. Mebarki, R. Sanchez, F. Durocher, C. Turgeon, Y. Labne, E. Rhéaume, C. Labrie and Y. Lachance (1996). The 3β-hydroxysteroid Dehydrogenase/isomerase Gene Family: Lessons from Type II 3β-HSD Congenital Deficiency. Signal Transduction in Testicular Cells, Ernst Schering Research Foundation Workshop. V. Hansson, F.O. Levy and K. Taskén. Berlin, Heidelberg, Springer-Verlag. Suppl. 2: 185-218.

Labrie, F., A. Belanger, L. Cusan and B. Candas (1997a). "Physiological changes in dehydroepiandrosterone are not reflected by serum levels of active androgens and estrogens but of their metabolites: Intracrinology." J Clin Endocrinol Metab 82(8): 2403-2409.

Labrie, F., A. Belanger, L. Cusan, J. L. Gomez and B. Candas (1997b). "Marked decline in serum concentrations of adrenal C19 sex steroid precursors and conjugated androgen metabolites during aging." J Clin Endocrinol Metab 82: 2396-2402.

Labrie, F., P. Diamond, L. Cusan, J. L. Gomez, A. Belanger and B. Candas (1997). "Effect of 12-month dehydroepiandrosterone replace-

(56) References Cited

OTHER PUBLICATIONS ment therapy on bone, vagina, and endometrium in postmenopausal women." J Clin Endocnnol Metab 82(10): 3498-505.
Labrie, F., V. Luu-The, S. X. Lin, C. Labrie, J. Simard, R. Breton and A. Bélanger (1997). "The key role of 17β-HSDs in sex steroid biology." Steroids 62: 148-158.
Labrie, F., C. Labrie, A. Bélanger, J. Simard, V. Giguère, A. Tremblay and G. Tremblay (2001). "EM-652 (SCH 57068), a pure SERM having complete antiestrogenic activity in the mammary gland and endometnum." J. Steroid Biochem. Mol. Biol. 79: 213-225.
Labrie, F., V. Luu-The, C. Labrie, A. Bélanger, J. Simard, S.-X. Lin and G. Pelletier (2003). "Endocrine and intracnne sources of androgens in women: inhibition of breast cancer and other roles of androgens and their precursor dehydroepiandrosterone." Endocrine Reviews 24(2): 152-182.
Labrie, F., V. Luu-The, A. Bélanger, S.-X. Lin, J. Simard and C. Labrie (2005). "Is DHEA a hormone? Starling Review." J Endocrinol 187: 169-196.
Labrie, F., A. Bélanger, P. Bélanger, R. Bérubé, C. Martel, L. Cusan, J. L. Gomez, B. Candas, I. Castiel, V. Chaussade, C. Deloche and J. Leclaire (2006). "Androgen glucuronides instead of testosterone as the new markers of androgenic activity in women." Journal Ster Biochem & Mol Biol 99: 182-188.
Labrie, F. (2007). "Drug Insight: breast cancer prevention and tissue-targeted hormone replacement therapy." Nature Clinical Practice, Endocrinology & Metabolism 3(8): 584-593.
Labrie, F., A. Belanger, P. Belanger, R. Berube, C. Martel, L. Cusan, J. Gomez, B. Candas, V. Chaussade, I. Cashel, C. Deloche and J. Leclaire (2007). "Metabolism of DHEA in postmenopausal women following percutaneous administration." J Steroid Biochem Mol Biol 103(2): 178-88.
Labrie, F., L. Cusan, J. L. Gomez, I. Côté, R. Bérubé, P. Bélanger, C. Martel and C. Labrie (2008). "Effect of Intravaginal DHEA on Serum DHEA and Eleven of its Metabolites in Postmenopausal Women." Journal Ster Biochem & Mol Biol 111: 178-94.
Labrie, F., D. Archer, C. Bouchard, M. Fortier, L. Cusan, J. L. Gomez, G. Girard, M. Baron, N. Ayotte, M. Moreau, R. Dubé, I. Côté, C. Labrie, L. Lavoie, L Berger, L. Gilbert, C. Martel and J. Balser (2009a). "Effect on intravaginal dehydroepiandrosterone (Prasterone) on libido and sexual dysfunction in postmenopausal women." Menopause 16: 923-931.
Labrie, F., D. Archer, C. Bouchard, M. Fortier, L. Cusan, J. L. Gomez, G. Girard, M. Baron, N. Ayotte, M. Moreau, R. Dubé, I. Côté, C. Labrie, L. Lavoie, L. Berger, L. Gilbert, C. Martel and J. Balser (2009b). "Intravaginal dehydroepiandrosterone (Prasterone), a physiological and highly efficient treatment of vaginal atrophy." Menopause 16: 907-922.
Labrie, F., D. Archer, C. Bouchard, M. Fortier, L. Cusan, J. L. Gomez, G. Girard, M. Baron, N. Ayotte, M. Moreau, R. Dubé, I. Côté, C. Labrie, L. Lavoie, L. Berger, L. Gilbert, C. Martel and J. Balser (2009c). "Serum steroid levels during 12-week intravaginal dehydroepiandrosterone administration." Menopause 16: 897-906.
Labrie, F., L. Cusan, J. L. Gomez, C. Martel, R. Berube, P. Belanger, A. Belanger, L. Vandenput, D. Mellström and C. Ohlsson (2009). "Comparable amounts of sex steroids are made outside the gonads in men and women: strong lesson for hormone therapy of prostate and breast cancer." J Steroid Biochem Mol Biol 113: 52-56.
Labrie, F. (2010). DHEA, important source of sex steroids in men and even more in women. Neuroendocrinology, the Normal Neuroendocrine System, Progress in Brain Research. L. Martini, Chrousos GP, Labrie F, Pacak K and D. Pfaff, eds., Elsevier. 182: chapter 4, 97-148.
Labrie, F., C. Martel, S. Gauthier, G. Pelletier and J. Y. Sancéau (2010). "Effect of toremifene and ospemifene, compared to acolbifene, on estrogen-sensitive parameters in rat and human uterine tissues." Horm Mol Biol Clin Invest 1: 139-146.
Labrie, F., C. Martel and J. Balser (2011). "Wide distribution of the serum dehydroepiandrosterone and sex steroid levels in postmenopausal women: role of the ovary?" Menopause 18: 30-43.

Labrie, Y., F. Durocher, Y. Lachance, C. Turgeon, J. Simard, C. Labrie and F. Labrie (1995). "Utiliser l'autre ref. The human type II 17 beta-hydroxysteroid dehydrogenase gene encodes two alternatively spliced mRNA species." DNA Cell Biol 14(10): 849-61.
Leiblum S., G. Bachmann, E. Kemmann, D. Colburn and L. Swartzman (1983). "Vaginal atrophy in the postmenopausal women. The importance of sexual activity and hormones." JAMA 249: 2195-2198.
Lemay, A., R. Maheux, N. Faure, C. Jean and A. T. A. Fazekas (1984). "Reversible hypogonadism induced by a luteinizing hormone-releasing, hormone (LHRH) agonist (Buserelin) as a new therapeutic approach for endometriosis." Fertil. Steril. 41: 863-871.
Lemay, A., S. Dodin and S. Dewailly (1989). "Long-term use of the low dose LHRH analogue combined with monthly medroxyprogesterone administration." Horm. Res. 32(Suppl. 1): 141-145.
Li, S., X. Yan, A. Bélanger and F. Labrie (1993). "Prevention by dehydroepiandrosterone of the development of mammary carcinoma induced by 7,12-dimethylbenz(a)anthracene (DMBA) in the rat." Breast Cancer Res. Treat. 29: 203-217.
Luo, S., C. Martel, S. Gauthier, Y. Mérand, A. Bélanger, C. Labrie and F. Labrie (1997a). "Long term inhibitory effects of a novel antiestrogen on the growth of ZR-75-1 and MCF-7 human breast cancer tumors in nude mice." Int. J. Cancer 73: 735-739.
Luo, S., C. Martel, A. Sourla, S. Gauthier, Y. Mérand A. Bélanger, C. Labrie and F. Labrie (1997b). "Comparative effects of 28-day treatment with the new antiestrogen EM-800 and tamoxifen on estrogen-sensitive parameters in the intact mouse." Int. J. Cancer 73: 381-391.
Luo, S., A. Sourla, C. Labrie A. Bélanger and F. Labrie (1997). "Combined effects of dehydroepiandrosterone and EM-800 on bone mass, serum lipids, and the development of dimethylbenz(a)anthracene (DMBA)-induced mammary carcinoma in the rat." Endocnnology 138: 4435-4444.
Luo, S., C. Labrie and F. Labrie (1998), "Prevention of development of dimenthylbenz(a)anthracene (DMBA)-induced mammary carcinoma in the rat by the new nonsteroidal antiestrogen EM-800 (SCH 57050)." Breast Cancer Res. Treat. 49: 1-11.
Luo, S., M. Stojanovic, C. Labrie and F. Labrie (1997). "Inhibitory effect of the novel antiestrogen EM-800 and medroxyprogesterone acetate on estrone-stimulated growth of dimethylbenz(a)anthracene-induced mammary carcinoma in rats." Int. J. Cancer 73: 580-586.
Luu-The, V., I. Dufort, N. Paquet, G. Reimnitz and F. Labrie (1995). "Structural characterization and expression of the human dehydroepiandrosterone sulfotransferase gene." DNA Cell Biol. 14: 511-518.
MacEwen, E. G. and I. D. Kurzman (1991). "Obesity in the dog: role of the adrenal steroid dehydroepiandrosterone (DHEA)." J. Nutr. 121: S51-S55.
Martel, C., A. Sourla, G. Pelletier, C. Labrie, M. Fournier, S. Picard, S. Li, M. Stojanovic and F. Labrie (1998). "Predominant androgenic component in the stimulatory effect of dehydroepiandrosterone on bone mineral density in the rat." J. Endocrinol. 157: 433-442.
Meldrum, D. R., R. J. Chang, J. Lu, W. Vale, J. Rivier and H. L. Judd (1982). "Medical oophorectomy" using a long-acting GNRH agonist—a possible new approach to the treatment of endometriosis. J. Clin. Endocrinol. Metab. 54: 1081-1083.
Michalska, D., J. J. Stepan, B. R. Basson and I. Pavo (2006). "The effect of raloxifene after discontinuation of long-term alendronate treatment of postmenopausal osteoporosis." J Clin Endocrinol Metab 91(3): 870-7.
Moghissi, K. S. and C. R. Boyce (1976). "Management of endometriosis with oral medroxyprogesterone acetate." Obstet. Gynecol. 47: 265-267.
Morales A. J., J. J. Nolan, J. C. Nelson and S. S. Yen (1994). "Effects of replacement dose of dehydroepiandrosterone in men and women of advancing age." J. Clin. Endocrinol. Metab. 78: 1360-1367.
Morales, A. J., R. H. Haubrich, J. Y. Hwang, H. Asakura and S. S. Yen (1998). "The effect of six months treatment with a 100 mg daily dose of dehydroepiandrosterone (DHEA) on circulating sex steroids, body composition and muscle strength in age-advanced men and women." Clin Endocrinol (Oxf) 49(4): 421-32.
Nair K. S., R. A. Rizza, P. O'Brien, K. Dhatariya, K. R. Short, A. Nehra, J. L. Vittone, G. G. Klee, A. Basu, R. Basu, C. Cobelli, G.

(56) References Cited

OTHER PUBLICATIONS

Toffolo, C. Dalla Man, D. J. Tindall, L. J. Melton, 3rd, G. E. Smith, S. Khosla and M. D. Jensen (2006). "DHEA in elderly women and DHEA or testosterone in elderly men." N Engl J Med 355(16): 1647-59.

Need, A. G., M. Horowitz, A. Bridges, H. A. Morris and B. E. Nordin (1989). "Effects of nandrolonSe decanoate and antiresorptive therapy on vertebral density in osteoporotic postmenopausal women." Arch. Intern. Med. 149: 57-60.

Nestler J. E., C. O. Barlascini, J. N. Clore and W. G. Blackard (1988). "Dehydroepiandrosterone reduces serum low density lipoprotein levels and body fat but does not alter insulin sensitivity in normal men." J. Clin. Endocrinol. Metab. 66: 57-61.

Nestor, J. J. J., T. L. Ho, R. Tahilramani, B. L. Horner, R. A. Simpson, G. H. Jones, G. I. McRae and B. H. Vickery (1984). LHRH Agonists and Antagonists Containing Very Hydrophobic Amino Acids. LHRH and its analogs. B. H. Vidcery, J. J. Nestor and E. S. E. Hafez. Lancaster, England, MTP Press: 22-33.

Noble, L. S., E. R. Simpson, A. Johns and S. E. Bulun (1996). "Aromatase expression in endometriosis." J Clin Endocrinol Metab 81(1): 174-9.

Noble, L. S., K. Takayama, K. M. Zeitoun, J. M. Putman, D. A. Johns, M. M. Hinshelwood, V. R. Agarwal, Y. Zhao, B. R. Carr and S. E. Bulun (1997). "Prostaglandin E2 stimulates aromatase expression in endometriosis-derived stromal cells." J Clin Endocrinol Metab 82(2): 600-6.

Notelovitz, M., N. Watts, C. Timmons, A. Addison, B. Wiita and L. Downey (1992). Effects of estrogen plus low dose androgen vs estrogen alone on menopausal symptoms in oophorectomized/hysterectomized women. North Am. Menopause Soc., Cleveland:101.

Pye, J. K., R. E. Mansel and L. E. Hughes (1985). "Clinical experience of drug treatments for mastalgia." Lancet 2: 373-377.

Rasmussen, K. R., M. J. Arrowood and M. C. Healey (1992): "Effectiveness of dehydroepiandrosterone in reduction of cryptosporidia) activity in immunosuppressed rats." Antimicrob. Agents Chemother. 36: 220-222.

Riis, B., C. Christiansen, J. Johansen and J. Jacobson (1990). "Is it possible to prevent bone loss in young women treated with luteinizing hormone-releasing hormone agonists?" J. Clin. Endocnnol. Metab. 70: 920-924.

Riva, H. L., J. H. Wilson and D. M. Kowasaki (1961). "Effect of norethynodrel on endometriosis." Am. J. Obstet. Gynecol. 82: 109-118.

Rivier, C., J. Rivier and W. Vale (1979). "Chronic effects of [D-Tr6_,Pro9-NEt]luteinizing hormone-releasing factor on reproductive processes in the male rat." Endocrinology 105: 1191-1201.

Rivier, J., C. Rivier, M. Perrin, J. Porter and W. Vale (1984). LHRH analogs as antiovulatory agents. LHRH and Its Analogs. B. H. Vickery, J. J. Nestor Jr. and E. S. E. Hafez. Lancaster, MTP Press: 11-22.

Rock, J. A., J. A. Truglia, R. J. Caplan and Z. E. S. Group (1993). "Zoladex (goserelin acetate implant) in the treatment of endometriosis: a randomized comparison with danazol." Obstet. Gynecol. 82: 198-205.

Ruttimann, J. (2008). "The menopause brain effect: Can hormone therapy help?" Endocrine News.: 15-16.

Sampson, J. A. (1921). "Perforating hemorrhagic (chocolate) cysts of the ovary." Archives of Surgery 3: 245-250.

Schriock, E. D., C. K. Buffington, G. D. Hubert, B. R. Kurtz, A. E. Kitabchi, J. E. Buster and J. R. Givens (1988). "Divergent correlations of circulating dehydroepiandrosterone sulfate and testosterone with insulin levels and insulin receptor binding." J. Clin. Endocrinol. Metab. 66: 1329-1331.

Schwartz, A. G., L. Pashko and J. M. Whitcomb (1986). "Inhibition of tumor development by dehydroepiandrosterone and related steroids." Toxicol. Pathol. 14: 357-362.

Sherwin, B. B. and M. M. Gelfand (1984). "Effects of parenteral administration of estrogen and androgen on plasma hormone levels and hot flushes in the surgical menopause." Am. J. Obstet. Gynecol. 148: 552-557.

Sherwin, B. B. and M. M. Gelfand (1985). "Differential symptom response to parenteral estrogen and/or androgen administration in the surgical menopause." Am. J. Obstet. Gynecol. 151: 153-160.

Sherwin, B. B. and M. M. Gelfand (1987). "The role of androgen in the maintenance of sexual functioning in oophorectomized women." Psychosom Med. 49: 397-409.

Sherwin, B. B. (1988). "Affective changes with estrogen and androgen replacement therapy in surgically menopausal women." J. Affect. Disord. 14: 177-187.

Simard, J., C. Labrie, A. Bélanger S. Gauthier, S. M. Singh, Y. Mérand and F. Labrie (1997). "Characterization of the effects of the novel non-steroidal antiestrogen EM-800 on basal and estrogen-induced proliferation of T-47D, ZR-75-1 and MCF-7 human breast cancer cells in vitro." Int. J. Cancer 73: 104-112.

Simard, J., R. Sanchez, D. Poirier, S. Gauthier, S. M. Singh, Y. Mérand, A. Bélanger, C. Labrie and F. Labrie (1997). "Blockade of the stimulatory effect of estrogens, OH-Tamoxifen, OH-Toremifene Droloxifene and Raloxifene on alkaline phosphatase activity by the antiestrogen EM-800 in human endometrial adenocarcinoma Ishikawa cells." Cancer Res. 57: 3494-3497.

Simón, J. A. (2009). "Vulvovaginal atrophy: new and upcoming approaches." Menopause 16(1): 5-7.

Sourla, A., S. Luo, C. Labrie, A. Bélanger and F. Labrie (1997). "Morphological changes induced by six-month treatment of intact and ovariectomized mice with tamoxifen and the pure antiestrogen EM-800." Endocrinology 138: 5605-5617.

Studd, J. W. W., W. P. Collins, S. Chakravarti, J. R. Newton, D. Oram and A. Parsons (1977). "Oestradiol and testosterone implants in the treatment of psychosexual problems in the post-menopausal women." British Journal of Obstetrics and Gynaecology. 84: 314-315.

Sun, H. S., K. Y. Hsiao, C. C. Hsu, M. H. Wu and S. J. Tsai (2003). "Transactivation of steroidogenic acute regulatory protein in human endometriotic stromalcells is mediated by the prostaglandin EP2 receptor." Endocrinology 144(9): 3934-42.

Surrey, E. and H. Judd (1992). "Reduction of vasomotor symptoms and bone mineral density loss with combined norethindrone and long-acting gonadotropin-releasing hormone agonist therapy of symptomatic endometriosis: a prospective randomized trial." J. Clin. Endocrinol. Metab. 75: 558-563.

Surrey, E. (1995). "Steroidal and nonsteroidal "add-back" therapy: extending safety and efficacy of gonadotropin-releasing hormone agonists in the gynecology patients." Fertil. Steril. 64: 673-685.

Suzuki, T., Suzuki, R. A. Daynes and E. G. Engleman (j991). "Dehydroepiandrosterone enhances IL2 production and cytotoxic effector function of human T cells." Clin. Immunol. Immunopathol. 61: 202-211.

Takayama, K., K. Zeitoun, R. T. Gunby, H. Sasano, B. R. Carr and S. E. Bulun (1998). "Treatment of severe postmenopausal endometriosis with an aromatase inhibitor." Fertil Steril 69(4): 709-13.

Tchernof, A., J. P. Després, A. Bélanger, A. Dupont, D. Prud'homme, S. Moorjani, P. J. Lupien and F. Labrie (1995). "Reduced testosterone and adrenal C19 steroid levels in obese men." Metabolism 44: 513-519.

Tremblay, A., G. B. Tremblay, C. Labrie, F. Labrie and V. Giguère (1998a). "EM-800, a novel antiestrogen, acts as a pure antagonist of the transcriptional functions of estrogen receptors α and β." Endocrinology 139: 111-118.

Tremblay, G. B., A. Tremblay, N. G. Copeland, D. J. Gilbert, N. A. Jenkins, F. Labrie and V. Giguere (1997). "Cloning, chromosomal localization and functional analysis of the murine estrogen receptor β." Mol. Endocrinol. 11: 353-365.

Tremblay, G. B., A. Tremblay, F. Labrie and V. Giguere (1998b). "Ligand-independent activation of the estrogen receptor α and β by mutations of a conserved tyrosine can be abolished by antiestrogens." Cancer Res. 58: 877-881.

Tremblay, G. B., A. Tremblay, F. Labrie and V. Giguère (1999). "Dominant activity of activation function-1 (AF-1) and differential

(56) References Cited

OTHER PUBLICATIONS stoichiometrc requirements for AF-1 and -2 in the estrogen receptor α-β heterodimeric complex." Mol. Cell. Biol. 19(3): 1919-1927.
Tsai, S. J., M. H. Wu, C. C. Lin, H. S. Sun and H. M. Chen (2001). "Regulation of steroidogenic acute regulatory protein expression and progesterone production in endometriotic stromal cells." J Clin Endocrinol Metab 86(12): 5765-73.
Villareal, D. T. and J. O. Holloszy (2004). "Effect of DHEA on abdominal fat and insulin action in elderly women and men: a randomized controlled trial." JAMA 292(18): 2243-8.
Willson, T. M., J. D. Norris, B. L. Wagner, I. Asplin, P. Baer, H. R. Brown, S. A. Jones, B. Henke, H. Sauls, S. Wolfe, D. C. Morris and D. P. McDonnell (1997). "Dissection of the molecular mechanism of action of GW5638, a novel estrogen receptor ligand, provides insights into the role of estrogen receptor in bone." Endocrinology 138(9): 3901-3911.
Women's Health Initiative (Jul. 17, 2002). "Risks and benefits of estrogen plus progestin in healthy postmenopausal women." JAMA 288(3): 321-333.
Yang, S., Z. Fang, T. Suzuki, H. Sasano, J. Zhou, B. Gurates, M. Tamura, K. Ferrer and S. Bulun (2002). "Regulation of aromatase P450 expression in endometriotic and endometrial stromal cells by CCAAT/enhancer binding proteins (C/EBPs): decreased C/EBPbeta in endometriosis is associated with overexpression of aromatase." J Clin Endocrinol Metab 87(5): 2336-45.
Zeitoun, K., K. Takayama, M. D. Michael and S. E. Bulun (1999). "Stimulation of aromatase P450 promoter (II) activity in endometriosis and its inhibition in endometrium are regulated by competitive binding of steroidogenic factor-1 and chicken ovalbumin upstream promoter transcription factor to the same cis-acting element." Mol Endocrinol 13(2): 239-53.
Zumoff, B., J. Levin, R. S. Rosenfeld, M. Markham, G. W. Strain and D. K. Fukushima (Sep. 1981). "Abnormal 24-hr mean plasma concentrations of dehydroepiandrosterone and dehydroisoandrosterone sulfate in women with primary operable breast cancer." Cancer Res. 41: 3360-3363.
Céline Martel, et al., "Prevention of Bone Loss by EM-800 and Raloxifene in the Ovariectomized Rat," Journal of Steroid Biochemistry & Molecular Biology 74, pp. 45-56, 2000.
Max Hasmann, et al., "Preclinical Data for Droloxifene," Cancer Letters 84, pp. 101-116, 1994.
Somnath Roy, et al., "Nature of Estrogenic and Anti-Estrogenic Actions of Centchroman on Rat Uteris," Contraception, vol. 13, No. 5, pp. 597-604, May 1976.
Fernand Labrie, et al., Chapter 9, Third- and Fourth-Generation SERMs, in Manni A., et al., "Selective Estrogen Receptor Modulators: Research and Clinical Applications," Totowa, NJ: Humana Press Inc., pp. 167-187, 2002.
Ahalya Premkumar, et al., "Gynecologic and Hormonal Effects of Raloxifene in Premenopausal Women," Fertility and Sterility, vol. 88, No. 6, pp. 1637-1644, Dec. 2007.
O.E. Young et al, "Effects of Fulvestrant 750 mg in Premenopausal Women With Oestrogen-Receptor-Positive Primary Breast Cancer," European Journal of Cancer 44, pp. 391-399, 2008.
Rivier J., et al., "Peptidomimetics of GnRH Antagonists: Present Status," Gynecological Endocrinology 13(Suppl. 1) 1999: see GnRH antagonist (T-98475), p. 8, abst. #015.
C. Koller, et al., "Propriétés et intérêt pharmaceutique des gels thermoréversibles à base de poloxamers et poloxamines," S.T.P. Pharma 3(2), pp. 115-124, 1987, Abst ract only.
B.H. Vickery et al., editors at p. 3-10 (J. J. Nestor Jr.), "Volume tightly bound—1 Development of agonistic LHRH analogs," LHRH and Its Analogs Advances in Reproductive Health Care, (English Abstract) (1984).
Extended European Search Report dated Nov. 7, 2013 in corresponding European Patent Application No. EP 11 79 4993 (English language).
C. Roux et al., "3 Year-Follow-Up of Bone Mineral Density After a Randomised Trial of 12-Month Treatment With a GnRH Agonist (leuprorelin 3.75 mg) Associated With 2 Options of Steroidal "Add Back" Regimens in Patients With Endometriosis," Journal of Bone and Mineral Research, vol. 20, No. 9, Suppl. 1, p. S173, (Sep. 2005), XP002715425 (Abstract).
H. Fernandez, et al., "One Year Comparison Between Two Add-Back Therapies in Patients Treated With a GnRH Agonist for Symptomatic Endometriosis: A Randomized Double-Blind Trial," Human Reproduction, vol. 19, No. 6, pp. 1465-1471 (2004).
Notice of Reasons for Rejection dated Apr. 7, 2014 issued in corresponding Japanese Patent Application No. 2013-514503 (wlth Enghsh language translation).
Karen Liby, et al., "The Combination of the Rexinoid, LG100268, and a Selective Estrogen Receptor Modulator, Either Arzoxifene or Acolbifene, Synergizes in the Prevention and Treatment of Mammary Tumors in an Estrogen Receptor—Negative Model of Breast Cancer," Clin. Cancer Res, 2006: 12(19) Oct. 1, 2006, pp. 5902-5909.
Céline Bouchard, MD, FRCSC, Editorial—"Selective Estrogen Receptor Modulators and Their Effects on Hot Flashes: A Dilemma," Menopause: The Journal of the North American Menopause Society, vol. 18, No. 5, pp. 477-479, 2011.
Notice of Office Action dated Sep. 15, 2014 in corresponding Korean Patent Application No. 10-2014-7014550 (with English language translation).
P. Ammann, et al., "A New Selective Estrogen Receptor Modulator HMR-3339 Fully Corrects Bone Alterations Induced by Ovariectomy in Adult Rats," Bone, 2004, 35, pp. 153-161.
Jörg B. Engel, et al., "Drug Insight: Clinical Use of Agonists and Antagonists of Luteinizing-Hormone-Releasing Hormone," Nature Clinical Practice Ehdocrinology & Metabolism, 2007, 3(2), pp. 157-167.
Hua Zhu Ke et al., "Long-Term Treatment of Lasofoxifene Preserves Bone Mass and Bone Strength and Does Not Adversely Affect the Uterus in Ovariectomized Rats," Endocrinology, 2004, 145(4), pp. 1996-2005.
Barry S. Komm, et al., "Developing a SERM: Stringent Preclinical Selection Criteria Leading to an Acceptable Candidate (WAY-140424) for Clinical Evaluation," Annals of the New York Academy of Sciences, 2006, 949(1), pp. 317-326.
Philipp Y. Maximov, et al., "The Discovery and Development of Selective Estrogen Receptor Modulators (SERMs) for Clinical Practice," Current Clinical Pharmacology, 2013, 8, pp. 135-155.
Masahiko Sato, et al., "LY353381.HC1: A Novel Raloxifene Analog With Improved SERM Potency and Efficacy In Vivo," The Journal of Pharmacology and Experimental Therapeutics, 1998, 287(1), pp. 1-7.
MM Carneiro, et al., "Androgen Receptor and 5α-Reductase Are Expressed in Pelvic Endometriosis," BJOG an International Journal of Obstetrics and Gynaecology, (2008), vol. 115, pp. 113-117.
C. Labrie, et al., "High Bioavailability of Dehydroepiandrosterone Administered Percutaneously in the Rat," Journal of Endocrinology, (1996), 150, pp. S107-S118.
Shouqi Luo, et al., "Effect of Dehydroepiandrosterone on Bone Mass, Serum Lipids, and Dimethylbenz(a)anthracene-Induced Mammary Carcinoma in the Rat*," Endocrinology, (1997), vol. 138, No. 8, pp. 3387-3394.
Louise M. Rasmussen, et al., "A Novel Dual-Target Steroid Sulfatase Inhibitor and Antiestrogen: SR 16157, a Promising Agent for the Therapy of Breast Cancer," Breast Cancer Res. Treat., (2007), vol. 106, pp. 191-203.
F. M. Fioretti, et al., "Revising the Rqle of the Androgen Receptor in Breast Cancer," Review, Journal of MolecularEndocrinology, 2014, vol. 52, No. 3, pp. R257-R265.
Joseph P. Garay, et al. "Androgen Receptor as a Targeted Therapy for Breast Cancer," Review Article, Am. J. Cancer Res., 2012, vol. 2, No. 4, pp. 434-445.
JoAnn V. Pinkerton, MD, et al., "Relief of Vasomotor Symptoms With the Tissue-Selective Estrogen Complex Containing Bazedoxifene/Conjugated Estrogens: A Randomized, Controlled Trial," Menopause: The Journal of the North American Menopause Society, vol. 16, No. 6, 2009, pp. 1116-1124.
Robert Lindsay, Ph.D., et al., "Efficacy of Tissue-Selective Estrogen Complex of Bazedoxifene/Conjugated Estrogens for Osteoporosis

(56) References Cited

OTHER PUBLICATIONS

Prevention in at-Risk Postmenopausal Women," Fertility and Sterility, vol. 92, No. 3, Sep. 2009, pp. 1045-1052.
Hong-Yuan Huang, Medical Treatment of Endometriosis, (2008), Chang Gung Med J, 31(5), pp. 431-440.
N Panay "Advances in the Medical Management of Endometriosis", (2008), BJOG, 115, pp. 814-817.
C. Martel, et al., Poster of presentation from applicant's research group (NAMS, 2000) entitled "Prevention of Bone Loss by Combined Treatment With EM-652.HC1 and DHEA in Female Rats Treated With an LHRH Agonist."
Christian Lemieux, et al., "The Estrogen Antagonist EM-652 and Dehydroepiandrosterone Prevent Diet- and Ovariectomy-Induced Obesity," Obesity Research, vol. 11, No. 3, Mar. 2003, pp. 477-490.
Sex steroid—Wikipedia (3 pages).
Promegestone—Wikipedia (3 pages).
J. E. Farmer, et al., "Gonadotrophin-Releasing Hormone Analogues for Endometriosis: Bone Mineral Density (Review)," Cochrane Database of Systematic Reviews, (2003), Issue 4. Art. No. CD001297, 73 pages.
Kamran S. Moghissi, MD, et al., "Goserelin Acetate (Zoladex)* With or Without Hormone Replacement Therapy for the Treatment of Endometeriosis," Fertility and Sterility, (Jun. 1998), vol. 69, No. 6, pp. 1056-1062.
Decision of Rejection dated May 8, 2017 in corresponding Japanese Patent Application No. 2015-104414 (7 total pages).
Masahiro Adachi, Male Bone and Sex Steroid, Adrenal Androgens (DHEA), The Bone, vol. 20, No. 2, (2006), pp. 67-73.
Endometriosis: Merck Manual Home Edition, May 2007, URL: http://merckmanuals.jp/home/%E5%A5%B3%E6%80%A7%E3%81%AE%E5%81%A5%E5%BA%B7%E4%B8%8A%E3%81%AE%E5%95%8F%E9%A1%8C/%E5%AD%90%E5%AE%AE%E5%86%85%E8%86%9C%E7%97%87/%E5%AD%90%E5%AE%AE%E5%86%85%E8%86%9C%E7%97%87.html#/v803367_ja.
W. M. van Weerden, et al., "Adrenal Glands of Mouse and Rat Do Not Synthesize Androgens," (1992) Life Sciences, vol. 50, No. 12, pp. 857-861.
M. S. Evsen, et al., "Serum Levels of Androgens and Prostate-Specific Antigen in Endometriosis," (2014), Clin. Exp. Obst. & Gyn., 41(4), pp. 432-435.
Pekka Keski-Rahkonen et al., "Fast and Sensitive Liquid Chromatography-Mass Spectrometry Assay for Seven Androgenic and Progestagenic Steroids in Human Serum," (2011), Journal of Steroid Biochemistry & Molecular Biology, 127, pp. 396-404.
Antigone Sourla, et al., "Effect of Dehydroepiandrosterone on Vaginal and Uterine Histomorphology in the Rat," (1998), J. Steroid Biochem. Molec. Biol., 66(3), pp. 137-149.
Peter Frigo, et al., "The Effects of Hormone Substitution in Depot Form on the Uterus in a Group of 50 Perimenopausal Women—A Vaginosonographic Study," (1995) Maturitas, 21, pp. 221-225.
A. M. Padula, "GnRH Analogues-Agonists and Antagonists," Animal Reproduction Science, 88 (2005), pp. 115-126.
Merja R. Häkkinen, et al., "Analysis by LC-MS/MS of Endogenous Steroids From Human Serum, Plasma, Endometrium and Endometriotic Tissue," Journal of Pharmaceutical and Biomedical Analysis, 152 (2018), pp. 165-172.
Georges Pelletier, et al., "Effect of Long-Term Treatment With the Antiestrogen EM-652.HCI on Pituitary Estrogen Receptor Alpha and Prolactin mRNA Expression in Intact, Ovariectomized and Gonadotropin-Releasing Hormone-Treated Female Rats," Neuroendocrinology, 74 (2001), pp. 367-374.
Sponsor: Endorecherche Inc., Testing Facility: Laboratory of Molecular Endocrinology, Research Study Protocol, "Prevention of Bone Loss by Treatment With EM-652.HCI and DHEA, Administered Alone or in Combination, to Intact Female Rats Receiving or Not a LHRH-A," Study No. URMA-r-04-99 (1999).
J.C. Illera et al.: "Measurement of serum and peritoneal fluid LH concentrations as a diagnostic tool lor human endometriosis", Reproduction (2001) 121, pp. 761-769.

First Office Action dated Dec. 23, 2019 in corresponding Chinese Patent Application No. 201710963202.X and Search Report with English translation.
J. Ellmén, et al., "Estrogenic Effects of Toremifene and Tamoxifen in Postmenopausal Breast Cancer Patients," Breast Cancer Research and Treatment, (2003), vol. 82, pp. 103-111.
Stefano Palomba, et al., "Raloxifene Administration in Women Treated with Gonadotropin-Releasing Hormone Agonist for Uterine Leiomyomas: Effects on Bone Metabolism", The Journal of Clinical Endocrinology & Metabolism, (2002), vol. 87, No. 10, pp. 4476-4481.
Young Hwa Cho, et al., Raloxifene Administration in Women Treated with Long Term Gonadotropin-Releasing Hoituone Agonist for Severe Endometriosis: Effects on Bone Mineral Density, J Menopausal Med., (2016), vol. 22, pp. 174-179.
Delyth Clemett, et al., "Raloxifene—A Review of Its Use in Postmenopausal Osteoporosis," ADIS Drug Evaluation, Drugs, (Aug. 2000), vol. 60, No. 2, pp. 379-411.
José Luis Duenas Diez, "Skeletal Effects of Selective Oestrogen Receptor Modulators (SERMs)," Human Reproduction Update, (2000), vol. 6, No. 3, pp. 255-258.
Bruce Ettinger, MD, "Reduction of Vertebral Fracture Risk in Postmenopausal Women With Osteoporosis Treated With Raloxifene, Results From 3-Year Randomized Clinical Trial," JAMA, (Aug. 18, 1999), vol. 282, No. 7, pp. 637-645.
Christine H. Cho, et al., "Therapeutic Potential of Oestrogen Receptor Ligands in Development for Osteoporosis," Expert Opinion, Emerging Drugs, (2001), vol. 6, No. 1, pp. 137-154.
Kiran Preet Malhotra, et al., Case Report "Centchroman: Is Unsupervised Long-Term Use Warranted? Case Report," The European Journal of Contraception and Reproductive Health Care, (Oct. 2011), vol. 16, pp. 403-406.
Peter Licht, M.D., et al., "Evidence for Cycle-Dependent Expiession of Full-Length Human Chorionic Gonadotropin/Luteinizing Hormone Receptor mRNA in Human Endometrium and Decidua," (Mar. 2003), Fertility and Sterility, vol. 79, Suppl. 1, pp. 718-723.
E. Reshef, et al., "The Presence of Gonadotropin Receptors in Nonpregnant Human Uterus, Human Placenta, Fetal Membranes, and Decidua*," (1990), Journal of Clinical Endocrinology and Metabolism, vol. 70, No. 2, pp. 421-430.
Nafis A. Rahman, et al., "Recent Progress in Luteinizing Hormone/Human Chorionic Gonadotrophin Hormone Research," (2009), Molecular Human Reproduction, vol. 15, No. 11, pp. 703-711.
Paolo Vercellini, et al., "Endometriosis, Current Therapies and New Pharmacological Developments," (2009), Drugs, vol. 69, No. 6, pp. 649-675.
Dominique Finas, et al., "Cetrorelix in the Treatment of Female Infertility and Endometriosis," (2006), Expert Opinion on Pharmacotherapy, vol. 7, No. 15, pp. 2155-2168.
Stefano Palomba, et al., "Long-Term Effectiveness and Safety of GnRH Agonist Plus Raloxifene Administration in Women With Uterine Leiomyomas," (2004), Human Reproduction, vol. 19, No. 6, pp. 1308-1314.
Gábor Mezö, et al., "Luteinizing Hormone-Releasing Antagonists," (2009), Expert Opinion on Therapeutic Patents, vol. 19, No. 12, pp. 1771-1785.
G. S. Harrison, et al., "Gonadotropin-Releasing Hormone and its Receptor in Normal and Malignant Cells," (2004), Endocrine-Related Cancer, vol. 11, No. 4, pp. 725-748.
Sophie Dauvois, et al., "Inhibitory Effect of Androgens on DMBA-Induced Mammary Carcinoma in the Rat," (1989), Breast Cancer Research and Treatment, vol. 14, No. 3, pp. 299-306.
Pascale V. Nantermet, et al., "Androgenic Induction of Growth and Differentiation in the Rodent Uterus Involves the Modulation of Estrogen-Regulated Genetic Pathways," (2005), Endocrinology, vol. 146, No. 2, pp. 564-578.
Additional test data received from the Applicant Dec. 18, 2021-r-04-99-Endometrium Uterus Ovaries.
L. Poretsky, et al., Metabolic and Honuonal Effects of Oral DHEA in Premenopausal Women with HIV Infection, Horm. Metab. Res., (Mar. 2009), vol. 41, No. 3, pp. 244-249.
Dale W. Stovall, MD, et al., "The Effects of Combined Raloxifene and Oral Estrogen on Vasomotor Symptoms and Endometrial Safety,"

(56) References Cited

OTHER PUBLICATIONS

Menopause: The Journal of The North American Menopause Society, vol. 14, No. 3, 2007, pp. 510-517.

Pamela Stratton, MD, et al., "Return of Chronic Pelvic Pain From Endometriosis After Raloxifene Treatment," Obstetrics and Gynecology, vol. 111, No. 1, Jan. 2008, pp. 88-96.

Kohzo Aisaka, "Effectiveness of Bisphosphonate Administration During Gn-RH Agonist Therapy for Endometriosis," Nippon Rinsho, (2009), vol. 67, No. 5, pp. 1027-1030.

Étienne Audet-Walsh, et al., "Profiling of Endogenous Estrogens, Their Precursors, and Metabolites in Endometrial Cancer Patients: Association With Risk and Relationship to Clinical Characteristics," J. Clin. Endocrinol. Metab., (Feb. 2011), 96(2):E330-E339.

\* cited by examiner

METHODS OF TREATING OR PREVENTING ESTROGEN-RELATED DISEASES

CROSS REFERENCE TO RELATED APPLICATION(S)

The present application claims priority of U.S. Provisional Application No. 61/355,465 filed Jun. 16, 2010, the contents of which are all incorporated herein by reference.

FIELD OF THE INVENTION

The present invention relates to methods for treating or reducing the likelihood of acquiring estrogen-related (e.g. estrogen-exacerbated) diseases including endometriosis using novel combination therapies in susceptible warm-blooded animals, including humans. In particular, one combination includes administering a selective estrogen receptor modulator (SERM), and inhibiting ovarian secretions, e.g., by administering an LHRH agonist or antagonist. In some embodiments, a precursor of sex steroids, said precursor being selected from the group consisting of dehydroepiandrosterone (DHEA), dehydroepiandrosterone sulfate (DHEA-S), androst-5-ene-3β,17β-diol (5-diol), and androstenedione or a compound transformed into one of these, is also administered.

BACKGROUND OF THE RELATED ART

Endometriosis is a frequent gynecological disease responsible for significant proportion of infertility and for high incidence of dysmenorrhea as well as pelvic, abdominal or vaginal pain. In terms of incidence, endometriosis is the second most frequent gynecological disorder after leiomyoma (Jones and Jones 1981) which are seen in 20% of women over age 35 (Conley and Lacey 1984). Endometriosis is defined as "the presence of ectopic tissue which possesses the histologic structure and function of the uterine mucosa" (Sampson 1921). It is a debilitating disease which can affect women from menarche to menopause. (Kistner 1979) has estimated that 30 to 40% of women with endometriosis are infertile.

Since endometrial tissue requires estrogens for its growth and proliferation, a state of hypoestrogenism results in atrophy and regression of endometriosis as observed following natural or surgical menopause in women as well as in experimental animals (Dizerega, Barber et al. 1980). As will be discussed later, removal of ovarian estrogens does not remove all estrogens in endometriotic tissue, while it removes all estrogens in normal human endometrium which lacks the enzymes to make estradiol, especially aromatase.

Pseudopregnancy and progestin therapy have been reported to improve endometriosis, relieving pelvic pain and dysmenorrhea in more than 80% of patients, but frequently transiently (Kistner 1959; Riva, Wilson et al. 1961; Kistner 1962; Moghissi and Boyce 1976). Similar observations were reported with androgens: methyl testosterone was partially effective in relieving dysmenorrhea and abdominal pain, but if higher dosages were used, important masculinizing signs appeared. In addition, ovulation was not consistently inhibited and treatment with androgens raised the possibility of virilization of the female fetus or genitourinary teratogenicity (Kistner 1979).

Initial studies of GnRH-a (also called LHRH agonist) therapy showed both subjective and objective improvement among patients with endometriosis (Lemay, Maheux et al. 1984; Erickson and Ory 1989), and controlled comparative studies demonstrated similar efficacy and better tolerability for GnRH-a compared with Danazol (Henzl, Corson et al. 1988; Rock, Truglia et al. 1993). It is thus well established that estrogen deficiency induced by LHRH agonists shows clinical benefits in endometriosis (Meldrum, Chang et al. 1982; Lemay, Maheux et al. 1984).

Despite the above-mentioned benefits, wide application of GnRH-a therapy in endometriosis has been limited by the hypoestrogenic side effects, such as vasomotor symptoms, vaginal dryness, emotional instability, insomnia, and loss of bone mineral density (BMD). Concerns about the long-term effect of these side effects, particularly loss of BMD, have limited the duration of treatment with GnRH-a therapy to 6 months for most gynecologic disorders (Surrey 1995).

Following our original observations that chronic administration of an LHRH agonist led to an inhibition of ovarian function characterized by a loss of ovarian LH receptors (Auclair, Kelly et al. 1977a; Auclair, Kelly et al. 1977b; Auclair, Ferland et al. 1978) and blockage of steroidogenesis (Bélanger, Auclair et al. 1979; Rivier, Rivier et al. 1979; Bélanger, Labrie et al. 1980) in male rats, it became of interest to investigate the possibility of a similar loss of ovarian gonadotropin receptors in female animals. In fact, a single injection of 8 ng of an LHRH agonist on diestrus I leads to a significant reduction of ovarian LH receptors (30%) (Kledzik, Cusan et al. 1978). A near maximal inhibition (60%) of ovarian LH receptors is seen at the dose of 40 ng, the inhibitory effect remaining of similar magnitude up to a dose of 25 µg. The decrease in ovarian LH receptors is accompanied by a marked reduction of uterine wet weight, intrauterine fluid, and plasma progesterone concentration as measured on the morning of expected proestrus; serum LH and FSH levels remain unchanged (Kledzik, Cusan et al. 1978).

In fact, estrogen deficiency is known to cause bone loss and osteoporosis, thus limiting the use of otherwise efficient LHRH agonists for the treatment of endometriosis and uterine fibroids. This has led to the suggestion of using a single 6-month course of LHRH agonist for the treatment of endometriosis (Fogelman 1992). Such a treatment schedule is generally accompanied by a return of endometriosis upon cessation of LHRH agonist treatment because of insufficient apoptosis of endometriotic cells.

"Add-back" hormone replacement therapy (HRT), the combining of various agents with GnRH-a, has been recommended as a means of maintaining a therapeutic response and reducing potential adverse events of GnRH therapy. The rationale for this approach derives from the estrogen threshold hypothesis, which stipulates that estrogen within a certain concentration range may partially prevent bone loss while not stimulating growth of endometrial lesions (Barbieri 1992). To prevent the bone loss associated with LHRH-A therapy, the addition of low dose estrogen (add-back therapy) has thus been studied. It is unlikely, however, that maximal effects on endometriosis are achieved with add-back estrogen therapy.

When the progestogen medroxyprogesterone acetate (MPA) was used with an LHRH agonist for 6 months, no significant BMD change was found in the proximal and distal forearm (Friedman 1989). Progestogen therapy in the form of medroxyprogesterone acetate (MPA) (Lemay, Dodin et al. 1989; Cedars, Lu et al. 1990) or norethindrone (Riis, Christiansen et al. 1990; Eldred, Haynes et al. 1992; Surrey and Judd 1992) in combination with GnRH-a therapy has been evaluated in several small studies. Both therapies appear to eliminate vasomotor symptoms and BMD loss associated with GnRH-a therapy, but continuous administration of MPA appears to reverse the beneficial effects of GnRH-a, and norethindrone has adverse effects on the lipid profile (Surrey 1995).

MPA, however, has shown an increased risk of breast cancer (Women's Health Initiative 2002).

Estrogen receptor antagonists can also be useful to block the estrogens responsible for stimulation of endometriotic tissue proliferation. Estrogen receptor antagonists to be used can be Fulvestrant, Raloxifene, Tamoxifen, Toremifene, Arzoxifene, LY 335563 (Desmethylarzoxifene), LY 335124, LY 326315, CHF-4227, Nafoxidine, Lasofoxifene, LY-2066948, LY-2120310, Ospemifene, Sivifene (A-007), TAS-108, Bazedoxifene acetate (1-{4-[2-(Azepan-1-yl) ethoxy]benzyl}-2-(4-hydroxyphenyl)-3-methyl-4H-indol-5-ol acetate), ERA-923, Afimoxifene, (Z)-4-hydroxytamoxifen, Enclomiphene, Fispemifene, Acolbifene, EM-652, EM-800, Droloxifene, Idoxifene, GW 5638, TAT-59, GW-7603, Centchroman, Levormeloxifene, ICI-164384, BL-3040, CH-4893237, SR 16158, SR 16137, Rad-1901, SERM 3471 (PSK-3471), HMR 3339, HMR 3656, CC 8490, 11β-Fluoro-7α-[5-(methyl3-[(4,4,5,5,5-pentafluoropentyl)sulfanyl]propylamino)pentyl]estra-1,3,5(10)-triene-3,17β-diol (SH 646, see WO1998/007740), 11β-Fluoro-17α-methyl-7α-5-[methyl(8,8,9,9,9-pentafluorononyl) amino]pentylestra-1,3,5(10)-triene-3,17β-diol (see WO2003/045972) or (+)-3-(4-Hydroxyphenyl)-2-[4-(2-piperidin-1-yletoxy)phenyl]-4-(trifluoromethyl)-2H-chromen-7-ol (see WO2001/68634).

Steroidal and non-steroidal antiestrogens (Selective Estrogen Receptor Modulators) have been disclosed in the treatment of estrogen-related diseases, including endometriosis in U.S. Pat. Nos. 5,395,842; 5,393,785; and in U.S. Pat. No. 5,204,337. Other Selective Estrogen Receptor Modulators have been also disclosed for the treatment of endometriosis in WO 97/04763; UK 2 303 628 A; WO 96/09040; WO 96/09041; EP 0 652 005 A1; EP 0 731 093 A1; U.S. Pat. No. 5,484,797; EP 0 761 669 A2; U.S. Pat. No. 5,567,828; EP 0 729 951 A1; and EP 0 703 228 A1; WO 2004/009086; US 2004/0259915; WO 2005/073190; WO 2005/073205; WO 2005/073206; and WO 2005/073244. Combination therapy for the treatment of estrogen-sensitive disease has been disclosed in U.S. Pat. No. 5,550,107.

The combination of LHRH agonist or antagonist with a selective estrogen receptor modulator (SERM) or antiestrogen has been disclosed in the treatment of estrogen-related diseases including endometriosis in EP 1424080 A1, U.S. Pat. No. 7,309,691 B2, US 2001/0041672 A1 and WO 02/056903 A2. The use of clomiphene to protect the skeleton during LHRH agonist therapy of endometriosis has been suggested (Goulding and Fisher 1991).

DHEA, DHEA-S, 5-diol and androstenedione can be converted in a cell- and tissue-specific fashion into estrogens and/or androgens by the process of intracrinology (Labrie, Bélanger et al. 1988; Labrie 1991; Labrie, Luu-The et al. 2005 and Labrie 2007).

This invention describes a new method for treating estrogen-related diseases including endometriosis.

SUMMARY OF THE INVENTION

It is accordingly an object of the present invention to provide effective methods of treatment for estrogen-related disease including endometriosis while minimizing undesirable side effects.

It is another object to provide methods of reducing the risk of acquiring the above diseases.

It is another object to provide kits suitable for use in the above methods.

In one embodiment, the invention pertains to a method of treating or reducing the risk of acquiring estrogen-related diseases including endometriosis comprising administering in a patient in need of said treatment or said reduction a therapeutically effective amount of an LHRH agonist or antagonist and further comprising administering to said patient a therapeutically effective amount of a selective estrogen receptor modulator (SERM) as part of a combination therapy.

In another embodiment, the invention pertains to a method of treating or reducing the risk of acquiring estrogen-related diseases including endometriosis comprising administering in a patient in need of said treatment or said reduction a therapeutically effective amount of an LHRH agonist or antagonist and further comprising administering to said patient a therapeutically effective amount of a selective estrogen receptor modulator (SERM) and a therapeutically effective amount of a sex steroid precursor selected from the group consisting of dehydroepiandrosterone (DHEA), dehydroepiandrosterone sulfate (DHEA-S), 4-androstene-3,17-dione, androst-5-ene-3β,17β-diol (5-diol), compounds transformed in vivo into either (prodrugs), and salts thereof.

As used herein, an antiestrogen is a compound which directly or through its active metabolite(s) blocks estrogen receptors, thereby making them unavailable to estrogenic compounds which could otherwise activate these receptors. A selective estrogen receptor modulator (SERM) is a compound that either directly or through its active metabolite(s) functions as an estrogen receptor antagonist ("antiestrogen") in endometrial and breast tissue, yet provides an estrogen-like effect on bone tissue and on serum cholesterol levels (i.e. by reducing serum cholesterol). Non-steroidal compounds that function as estrogen receptor antagonists in vitro, in human breast cancer cell lines or in in vivo models of human breast cancer (especially if the compound acts as an antiestrogen in human breast cancer cells growing as xenografts in nude mice) is likely to function as a SERM. Conversely, steroidal antiestrogens tend not to function as SERMs because they tend not to display any beneficial effect on bone. Non-steroidal antiestrogens found by us or reported in the literature to function as SERMs include EM-800, EM-652.HCl (Acolbifene), Raloxifene, LY 335563, LY 353381 (Arzoxifene), Idoxifene, GW 5638, Tamoxifen, (Z)-4-hydroxytamoxifen, Toremifene, Ospemifene, Droloxifene, Lasofoxifene, Bazedoxifene (TSE-424), and Pipendoxifene (ERA-923), but are not limited to these compounds. SERMs in accordance with the invention may be administered in the same dosage as known in the art when these compounds are used in the breast cancer treatment or for reduction of risk of development of breast cancer or osteoporosis.

As used herein, the term endometriosis includes but is not limited to peritoneal disease, ovarian endometriosis, and rectovaginal disease. It includes growth of endometrial tissue at any site, including the inner layer of the uterus or endometrium.

In another embodiment, the invention pertains to a method of treating or reducing the risk of acquiring other estrogen-related diseases like uterine fibroids, uterine leiomyomas, endometrial cancer, uterine cancer, uterine leiomyosarcomas, ovarian cancer, breast cancer, polycystic ovary syndrome, dysfunctional uterine bleeding, vaginal bleeding, menorrhagia, premenstrual syndrome, migraine headache, cervical intraepithelial neoplasia, adenomyosis, and Alzheimer's disease comprising administering in a patient in need of said treatment or said reduction a therapeutically effective amount of an LHRH agonist or antagonist and further comprising administering to said patient a therapeutically effective amount of a selective estrogen receptor modulator (SERM) and optionally a therapeutically effective amount of a sex steroid precursor selected from the group consisting of dehydroepiandrosterone (DHEA), dehydroepiandrosterone sulfate (DHEA-S), 4-androstene-3,17-dione, androst-5-ene-3β,17β-diol (5-diol), compounds transformed in vivo into either (prodrugs), and salts thereof.

Other features and advantages of the present invention will become apparent from the following non-limiting description of preferred embodiments, which refers to accompanying drawings.

DETAILED DESCRIPTION

Figure 1:
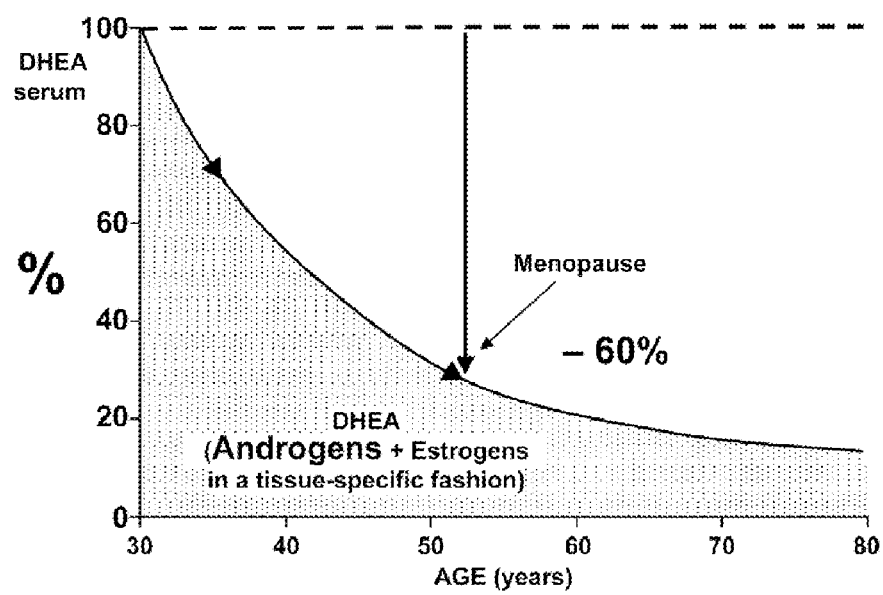
FIG. 1 is a schematic representation of the progressive decrease in serum DHEA with age. At time of menopause, serum DHEA has already decreased by 60% and the decrease continues thereafter. A parallel decrease is observed for total androgen exposure.

A list of complete citations to references cited herein in short-form format is set forth below:

Ailawadi, R. K., S. Jobanputra, M. Kataria, B. Gurates and S. E. Bulun (2004). "Treatment of endometriosis and chronic pelvic pain with letrozole and norethindrone acetate: a pilot study." Fertil Steril 81(2): 290-6.

Allen, L. V. with the contributions by D. B. Worthen and B. Mink (2008). Suppository bases and their characteristics (Chapter 3). Suppositories. Pharmaceutical Press, London, UK: 27-49.

Auclair, C., P. A. Kelly, D. H. Coy, A. V. Schally and F. Labrie (1977a). "Potent inhibitory activity of [D-Leu6, des-Gly-NH210]ethylamide on LH/hCG and PRL testicular receptor levels in the rat." Endocrinology 101: 1890-1893.

Auclair, C., P. A. Kelly, F. Labrie, D. H. Coy and A. V. Schally (1977b). "Inhibition of testicular luteinizing receptor level by treatment with a potent luteinizing hormone-releasing hormone agonist of human chorionic gonadotropin." Biochem. Biophys. Res. Commun. 76: 855-862.

Auclair, C., L. Ferland, L. Cusan, P. A. Kelly, F. Labrie, G. Azadian-Boulanger and J. P. Raynaud (1978). "Effet inhibiteur de la LHRH sur les récepteurs de la LH dans le testicule chez le rat." C. R. Acad. Sci. Paris, Série D 286: 1305-1307.

Barbieri, R. (1992). "Hormone treatment of endometriosis: the estrogen threshold hypothesis." Am. J. Obstet. Gynecol. 166: 740-745.

Bardon, S., F. Vignon, D. Chalbos and H. Rochefort (1985). "RU486, a progestin and glucocorticoid antagonist, inhibits the growth of breast cancer cells via the progesterone receptor." J. Clin. Endocrinol. Metab. 60: 692-697.

Baxendale, P. M., M. J. Reed and V. H. James (1981). "Inability of human endometrium or myometrium to aromatize androstenedione." J Steroid Biochem 14(3): 305-6.

Bélanger, A., C. Auclair, C. Séguin, P. A. Kelly and F. Labrie (1979). "Down-regulation of testicular androgen biosynthesis and LH receptor levels by an LHRH agonist, role of prolactin." Mol. Cell. Endocrinol. 13: 47-53.

Bélanger, A., F. Labrie, A. Lemay, S. Caron and J. P. Raynaud (1980). "Inhibitory effects of a single intranasal administration of [D-Ser(TBU)6, des-Gly-NH210]LHRH agonist, a potent LHRH agonist, on serum steroid levels in normal adult men." J. Steroid Biochem. 13: 123-126.

Black, L. J., M. Sato, E. R. Bowley, D. E. Magee, A. Bekele, D. C. Williams, G. J. Cullinan, R. Bendele, R. F. Kaufman, W. R. Bensch, C. A. Frolik, J. D. Termine and H. U. Bryant (1994). "Raloxifene (LY139481 HCl) prevents bone loss and reduces serum cholesterol without causing uterine hypertrophy in ovariectomized rats." J. Clin. Invest. 93: 63-69.

Bulun, S. E., S. Yang, Z. Fang, B. Gurates, M. Tamura, J. Zhou and S. Sebastian (2001). "Role of aromatase in endometrial disease." J Steroid Biochem Mol Biol 79(1-5): 19-25.

Bulun, S. E., Z. Lin, G. Imir, S. Amin, M. Demura, B. Yilmaz, R. Martin, H. Utsunomiya, S. Thung, B. Gurates, M. Tamura, D. Langoi and S. Deb (2005). "Regulation of aromatase expression in estrogen-responsive breast and uterine disease: from bench to treatment." Pharmacol Rev 57(3): 359-83.

Burger, H. G., J. Hailes, M. Menelaus, J. Nelson, B. Hudson and N. Balazs (1984). "The management of persistent menopausal symptoms with oestradiol-testosterone implants: clinical, lipid and hormonal results." Maturitas 6: 351-358.

Casson, P. R., R. N. Andersen, H. G. Herrod, F. B. Stentz, A. B. Straughn, G. E. Abraham and J. E. Buster (1993). "Oral dehydroepiandrosterone in physiologic doses modulates immune function in postmenopausal women", Am. J. Obstet. Gynecol. 169: 1536-1539.

Cedars, M., J. Lu, D. Meldrum and H. Judd (1990). "Treatment of endometriosis with a long-acting gonadotropin-releasing hormone agonist plus medroxyprogesterone acetate." Obstet. Gynecol. 5: 641-645.

Colditz, G. A., S. E. Hankinson, D. J. Hunter, W. C. Willett, J. E. Manson, M. J. Stampfer, C. Hennekens, B. Rosner and F. E. Speizer (1995). "The use of estrogens and progestins and the risk of breast cancer in postmenopausal women." N. Engl. J. Med. 332: 1589-1593.

Coleman, D. L., E. H. Leiter and R. W. Schwizer (1982). "Therapeutic effects of dehydroepiandrosterone (DHEA) in diabetic mice." Diabetes 31: 830-833.

Conley, G. and M. D. Lacey (1984). Current Obstetric and Gynecologic Diagnosis and Treatment. R. C. Benten. Lange: 258-263.

Corbin, A., F. J. Bex and R. C. Jones (1984). "Comparison of LHRH agonist (AG) and antagonist (ANT): antifertility and therapeutic developments." J. Steroid Biochem. 20(6B)(1369): A9.

Couillard, S., M. Gutman, C. Labrie, A. Bélanger, B. Candas and F. Labrie (1998). "Comparison of the effects of the antiestrogens EM-800 and Tamoxifen on the growth of human breast ZR-75-1 cancer xenografts in nude mice." Cancer Res. 58: 60-64.

Couillard, S., C. Labrie, A. Bélanger, B. Candas, F. Pouliot and F. Labrie (1998). "Effect of dehydroepiandrosterone and the antiestrogen EM-800 on the growth of human ZR-75-1 breast cancer xenografts." J. Natl. Cancer Inst. 90: 772-778.

Coy, D. H., A. Horvath, M. V. Nekola, E. J. Coy, J. Erchegyi and A. V. Schally (1982). "Peptide antagonists of LHRH: large increases in antiovulatory activities produced by basic D-amino acids in the six position." Endocrinology 110: 1445-1447.

Diamond, P., L. Cusan, J. L. Gomez, A. Bélanger and F. Labrie (1996). "Metabolic effects of 12-month percutaneous DHEA replacement therapy in postmenopausal women." J. Endocrinol. 150: S43-S50.

Dizerega, S. G., D. L. Barber and G. D. Hodgen (1980). "Endometriosis: role of ovarian steroids in initiation, maintenance, and suppression." Fertil. Steril. 33: 649-653.

Draper, M. W., D. E. Flowers, J. A. Neild, W. J. fluster and R. L. Zerbe (1995). "Antiestrogenic properties of raloxifene." Pharmacology 50(4): 209-217.

Draper, M. W., D. E. Flowers, W. J. Huster, J. A. Neild, K. D. Harper and C. Arnaud (1996). "A controlled trial of raloxifene (LY139481) HCl: impact on bone turnover and serum lipid profile in healthy postmenopausal women." J. Bone Miner. Res. 11(6): 835-842.

Dutta, A. S., B. J. A. Furr, M. B. Giles and B. Valcaccia (1978). "Synthesis and biological activity of highly active a-aza analogues of luliberin." J. Med. Chem. 21(10): 1018-1024.

Eldred, J., P. Haynes and C. Thomas (1992). "A randomized double-blind placebo controlled trial of the effects of bone metabolism of the combination of nafarelin acetate and norethisterone." Clin. Endocrinol. 37: 354-359.

Erchegyi, J., D. H. Coy, M. V. Nekola, E. J. Coy, A. V. Schally, I. Mezo and I. Teplan (1981). "Luteinizing hormone-releasing hormone analogs with increased activity." Biochem. Biophys. Res. Commun. 100: 915-920.

Erickson, L. D. and S. J. Ory (1989). "GnRH analogues in the treatment of endometriosis." Obstet. Gynecol. Clin. North Am. 16: 23-45.

Fang, Z., S. Yang, B. Gurates, M. Tamura, E. Simpson, D. Evans and S. E. Bulun (2002). "Genetic or enzymatic disruption of aromatase inhibits the growth of ectopic uterine tissue." J Clin Endocrinol Metab 87(7): 3460-6.

Fogelman, I. (1992). "Gonadotropin-releasing hormone agonists and the skeleton." Fertil. Steril. 57: 715-724.

Friedman, A. J. (1989). "Treatment of leiomyomata uteri with short-term leuprolide followed by leuprolide plus estrogen-progestin hormone replacement therapy for 2 years: a pilot study." Fertil. Steril. 51: 526-528.

Gauthier, S., B. Caron, J. Cloutier, Y. L. Dory, A. Favre, D. Larouche, J. Mailhot, C. Ouellet, A. Schwerdtfeger, G. Leblanc, C. Martel, J. Simard, Y. Mérand, A. Bélanger, C. Labrie and F. Labrie (1997). "(S)-(+)-4-[7-(2,2-dimethyl-1-oxopropoxy)-4-methyl-2-[4-[2-(1-piperidinyl)-ethoxy]phenyl]-2H-1-benzopyran-3-yl]-phenyl 2,2-dimethylpropanoate (EM-800): a highly potent, specific, and orally active nonsteroidal antiestrogen." J. Med. Chem. 40: 2117-2122.

Gordon, G. B., L. M. Shantz and P. Talalay (1987). "Modulation of growth, differentiation and carcinogenesis by dehydroepiandrosterone." Adv. Enzyme Regul. 26: 355-382.

Goulding, A. and L. Fisher (1991). "Preventive effects of clomiphene citrate on estrogen-deficiency osteopenia elicited by LHRH agonist administration in the rat." J. Bone Miner. Res. 6(11): 1177-81.

Gurates, B., S. Sebastian, S. Yang, J. Zhou, M. Tamura, Z. Fang, T. Suzuki, H. Sasano and S. E. Bulun (2002). "WT1 and DAX-1 inhibit aromatase P450 expression in human endometrial and endometriotic stromal cells." J Clin Endocrinol Metab 87(9): 4369-77.

Henderson, E., J. Y. Yang and A. Schwartz (1992). "Dehydroepiandrosterone (DHEA) and synthetic DHEA analogs are modest inhibitors of HIV-1 IIIB replication." Aids Res. Hum. Retroviruses 8: 625-631.

Henneman, P. H. and S. Wallach (1957). "The use of androgens and estrogens and their metabolic effects. A review of the prolonged use of estrogens and androgens in postmenopausal and senile osteoporosis." AMA: Arch. Int. Med. 100: 715-723.

Henzl, M. R., S. L. Corson, K. Moghissi, V. C. Buttram, C. Bergvist and J. Jacobson (1988). "Administration of nasal nafarelin as compared with oral danazol for endometriosis: a multicentre double-blind comparative trial." N. Engl. J. Med. 318: 485-489.

Jankowski, C. M., W. S. Gozansky, R. S. Schwartz, D. J. Dahl, J. M. Kittelson, S. M. Scott, R. E. Van Pelt and W. M. Kohrt (2006). "Effects of dehydroepiandrosterone replacement therapy on bone mineral density in older adults: a randomized, controlled trial." J Clin Endocrinol Metab 91(8): 2986-93.

Johnston Jr, C. C. and S. Epstein (1981). "Clinical, biochemical, radiographic, epidemiologic, and economic features of osteoporosis." Orthop. Clin. North. Am. 12: 559-569.

Jones, H. W. and G. S. Jones (1981). Novak's, Textbook of Gynecology, Tenth Edition, Baltimore, Williams and Wilkins: 609-635.

Kauffman, R. F. and H. U. Bryant (1995). "Effective therapeutic management of the postmenopausal state will be a cornerstone in strategies for preserving or improving women's health in the 21st century." Drug News and Perspectives 8: 531-539.

Kistner, R. W. (1959). "The treatment of endometriosis by inducing pseudopregnancy with ovarian hormones: a report of fifty-eight cases." Fertil. Steril. 10: 539-556.

Kistner, R. W. (1962). "Infertility with endometriosis: a plan of therapy." Fertil. Steril. 13: 237-245.

Kistner, R. W. (1979). "Endometriosis and infertility." Clin. Obstet. Gynecol. 22: 101-119.

Kitawaki, J., T. Noguchi, T. Amatsu, K. Maeda, K. Tsukamoto, T. Yamamoto, S. Fushiki, Y. Osawa and H. Honjo (1997). "Expression of aromatase cytochrome P450 protein and messenger ribonucleic acid in human endometriotic and adenomyotic tissues but not in normal endometrium." Biol Reprod 57(3): 514-9.

Kledzik, G. S., L. Cusan, C. Auclair, P. A. Kelly and F. Labrie (1978). "Inhibition of ovarian LH and FSH receptor levels with an LH-releasing hormone agonist during the estrous cycle in the rat." Fertil. Steril. 30: 348-353.

Labrie, C., A. Bélanger and F. Labrie (1988). "Androgenic activity of dehydroepiandrosterone and androstenedione in the rat ventral prostate." Endocrinology 123: 1412-1417.

Labrie, F. (1991). "Intracrinology." Mol. Cell. Endocrinol. 78: C113-C118.)

Labrie, F., J. Simard, V. Luu-The, A. Bélanger and G. Pelletier (1992a). "Structure, function and tissue-specific gene expression of 3b-hydroxysteroid dehydrogenase/5-ene-4-ene isomerase enzymes in classical and peripheral intracrine steroidogenic tissues." J. Steroid Biochem. Mol. Biol. 43: 805-826.

Labrie, F., J. Simard, V. Luu-The, G. Pelletier, A. Bélanger, Y. Lachance, H. F. Zhao, C. Labrie, N. Breton, Y. de Launoit, M. Dumont, E. Dupont, E. Rhéaume, C. Martel, J. Couet and C. Trudel (1992b). "Structure and tissue-specific expression of 3b-hydroxysteroid dehydrogenase/5-ene-4-ene isomerase genes in human and rat classical and peripheral steroidogenic tissues." J. Steroid Biochem. Mol. Biol. 41: 421-435.

Labrie, F., J. Simard, V. Luu-The, A. Bélanger, G. Pelletier, Y. Morel, F. Mebarki, R. Sanchez, F. Durocher, C. Turgeon, Y. Labrie, É. Rhéaume, C. Labrie and Y. Lachance (1996). The 3b-hydroxysteroid dehydrogenase/isomerase gene family: lessons from type II 3b-HSD congenital deficiency. Signal Transduction in Testicular Cells, Ernst Schering Research Foundation Workshop. V. Hansson, F. O. Levy and K. Taskén. Berlin, Heidelberg, Springer-Verlag. Suppl. 2: 185-218.

Labrie, F., A. Bélanger, L. Cusan and B. Candas (1997a). "Physiological changes in dehydroepiandrosterone are not reflected by serum levels of active androgens and estrogens but of their metabolites: intracrinology." J Clin Endocrinol Metab 82(8): 2403-2409.

Labrie, F., A. Bélanger, L. Cusan, J. L. Gomez and B. Candas (1997b). "Marked decline in serum concentrations of adrenal C19 sex steroid precursors and conjugated androgen metabolites during aging." J Clin Endocrinol Metab 82: 2396-2402.

Labrie, F., P. Diamond, L. Cusan, J. L. Gomez, A. Bélanger and B. Candas (1997). "Effect of 12-month dehydroepiandrosterone replacement therapy on bone, vagina, and endometrium in postmenopausal women." J Clin Endocrinol Metab 82(10): 3498-505.

Labrie, F., V. Luu-The, S. X. Lin, C. Labrie, J. Simard, R. Breton and A. Bélanger (1997). "The key role of 17b-HSDs in sex steroid biology." Steroids 62: 148-158.

Labrie, F., C. Labrie, A. Bélanger, J. Simard, V. Giguére, A. Tremblay and G. Tremblay (2001). "EM-652 (SCH 57068), a pure SERM having complete antiestrogenic activity in the mammary gland and endometrium." J. Steroid Biochem. Mol. Biol. 79: 213-225.

Labrie, F., V. Luu-The, C. Labrie, A. Bélanger, J. Simard, S.-X. Lin and G. Pelletier (2003). "Endocrine and intracrine sources of androgens in women: inhibition of breast cancer and other roles of androgens and their precursor dehydroepiandrosterone." Endocrine Reviews 24(2): 152-182.

Labrie, F., V. Luu-The, A. Bélanger, S.-X. Lin, J. Simard and C. Labrie (2005). "Is DHEA a hormone? Starling Review." J Endocrinol 187: 169-196.

Labrie, F. (2006). "Future perspectives of SERMs used alone and in combination with DHEA." Endocr Relat Cancer 13(2): 335-355.

Labrie, F., A. Bélanger, P. Bélanger, R. Bérubé, C. Martel, L. Cusan, J. L. Gomez, B. Candas, I. Castiel, V. Chaussade, C. Deloche and J. Leclaire (2006). "Androgen glucuronides, instead of testosterone, as the new markers of androgenic activity in women." Journal Ster Biochem & Mol Biol 99: 182-188.

Labrie, F. (2007). "Drug Insight: breast cancer prevention and tissue-targeted hormone replacement therapy." Nature Clinical Practice, Endocrinology & Metabolism 3(8): 584-593.

Labrie, F., A. Bélanger, P. Bélanger, R. Berube, C. Martel, L. Cusan, J. Gomez, B. Candas, V. Chaussade, I. Castiel, C. Deloche and J. Leclaire (2007). "Metabolism of DHEA in postmenopausal women following percutaneous administration." J Steroid Biochem Mol Biol 103(2): 178-88.

Labrie, F., L. Cusan, J. L. Gomez, I. Côté, R. Bérubé, P. Bélanger, C. Martel and C. Labrie (2008). "Effect of Intravaginal DHEA on Serum DHEA and Eleven of its Metabolites in Postmenopausal Women." Journal Ster Biochem & Mol Biol 111: 178-94.

Labrie, F., D. Archer, C. Bouchard, M. Fortier, L. Cusan, J. L. Gomez, G. Girard, M. Baron, N. Ayotte, M. Moreau, R. Dubé, I. Côté, C. Labrie, L. Lavoie, L. Berger, L. Gilbert, C. Martel and J. Balser (2009a). "Effect on intravaginal dehydroepiandrosterone (Prasterone) on libido and sexual dysfunction in postmenopausal women." Menopause 16: 923-931.

Labrie, F., D. Archer, C. Bouchard, M. Fortier, L. Cusan, J. L. Gomez, G. Girard, M. Baron, N. Ayotte, M. Moreau, R. Dubé, I. Côté, C. Labrie, L. Lavoie, L. Berger, L. Gilbert, C. Martel and J. Balser (2009b). "Intravaginal dehydroepiandrosterone (Prasterone), a physiological and highly efficient treatment of vaginal atrophy." Menopause 16: 907-922.

Labrie, F., D. Archer, C. Bouchard, M. Fortier, L. Cusan, J. L. Gomez, G. Girard, M. Baron, N. Ayotte, M. Moreau, R. Dubé, I. Côté, C. Labrie, L. Lavoie, L. Berger, L. Gilbert, C. Martel and J. Balser (2009c). "Serum steroid levels during 12-week intravaginal dehydroepiandrosterone administration." Menopause 16: 897-906.

Labrie, F., L. Cusan, J. L. Gomez, C. Martel, R. Berube, P. Bélanger, A. Bélanger, L. Vandenput, D. Mellström and C. Ohlsson (2009). "Comparable amounts of sex steroids are made outside the gonads in men and women: strong lesson for hormone therapy of prostate and breast cancer." J Steroid Biochem Mol Biol 113: 52-56.

Labrie, F. (2010). DHEA, important source of sex steroids in men and even more in women. Neuroendocrinology, The Normal Neuroendocrine System, Progress in Brain Research. L. Martini, Chrousos G P, Labrie F, Pacak K and D. Pfaff, eds., Elsevier. 182: chapter 4, 97-148.

Labrie, F., C. Martel, S. Gauthier, G. Pelletier and J. Y. Sancéau (2010). "Effect of toremifene and ospemifene, compared to acolbifene, on estrogen-sensitive parameters in rat and human uterine tissues." Horm Mol Biol Clin Invest 1: 139-146.

Labrie, F., C. Martel and J. Balser (2011). "Wide distribution of the serum dehydroepiandrosterone and sex steroid levels in postmenopausal women: role of the ovary?" Menopause 18: 30-43.

Labrie, Y., F. Durocher, Y. Lachance, C. Turgeon, J. Simard, C. Labrie and F. Labrie (1995). "Utiliser l'autre réf. The human type II 17 beta-hydroxysteroid dehydrogenase gene encodes two alternatively spliced mRNA species." DNA Cell Biol 14(10): 849-61.

Leiblum, S., G. Bachmann, E. Kemmann, D. Colburn and L. Swartzman (1983). "Vaginal atrophy in the postmenopausal women. The importance of sexual activity and hormones." JAMA 249: 2195-2198.

Lemay, A., R. Maheux, N. Faure, C. Jean and A. T. A. Fazekas (1984). "Reversible hypogonadism induced by a luteinizing hormone-releasing hormone (LHRH) agonist (Buserelin) as a new therapeutic approach for endometriosis." Fertil. Steril. 41: 863-871.

Lemay, A., S. Dodin and S. Dewailly (1989). "Long-term use of the low dose LHRH analogue combined with monthly medroxyprogesterone administration." Horm. Res. 32(Suppl. 1): 141-145.

Li, S., X. Yan, A. Bélanger and F. Labrie (1993). "Prevention by dehydroepiandrosterone of the development of mammary carcinoma induced by 7,12-dimethylbenz(a)anthracene (DMBA) in the rat." Breast Cancer Res. Treat. 29: 203-217.

Luo, S., C. Martel, S. Gauthier, Y. Mérand, A. Bélanger, C. Labrie and F. Labrie (1997a). "Long term inhibitory effects of a novel antiestrogen on the growth of ZR-75-1 and MCF-7 human breast cancer tumors in nude mice." Int. J. Cancer 73: 735-739.

Luo, S., C. Martel, A. Sourla, S. Gauthier, Y. Mérand, A. Bélanger, C. Labrie and F. Labrie (1997b). "Comparative effects of 28-day treatment with the new antiestrogen EM-800 and tamoxifen on estrogen-sensitive parameters in the intact mouse." Int. J. Cancer 73: 381-391.

Luo, S., A. Sourla, C. Labrie, A. Bélanger and F. Labrie (1997). "Combined effects of dehydroepiandrosterone and EM-800 on bone mass, serum lipids, and the development of dimethylbenz(a)anthracene (DMBA)-induced mammary carcinoma in the rat." Endocrinology 138: 4435-4444.

Luo, S., C. Labrie and F. Labrie (1998). "Prevention of development of dimenthylbenz(a)anthracene (DMBA)-induced mammary carcinoma in the rat by the new nonsteroidal antiestrogen EM-800 (SCH 57050)." Breast Cancer Res. Treat. 49: 1-11.

Luo, S., M. Stojanovic, C. Labrie and F. Labrie (1997) "Inhibitory effect of the novel anti-estrogen EM-800 and medroxyprogesterone acetate (MPA) on estrone-stimulated growth of dimethylbenz(a)anthracene induced mammary carcinoma in the rats." Int. J. Cancer 73: 580-586.

Luu-The, V., I. Dufort, N. Paquet, G. Reimnitz and F. Labrie (1995). "Structural characterization and expression of the human dehydroepiandrosterone sulfotransferase gene." DNA Cell Biol. 14: 511-518.

MacEwen, E. G. and I. D. Kurzman (1991). "Obesity in the dog: role of the adrenal steroid dehydroepiandrosterone (DHEA)." J. Nutr. 121: S51-S55.

Martel, C., A. Sourla, G. Pelletier, C. Labrie, M. Fournier, S. Picard, S. Li, M. Stojanovic and F. Labrie (1998). "Predominant androgenic component in the stimulatory effect of dehydroepiandrosterone on bone mineral density in the rat." J. Endocrinol. 157: 433-442.

Meldrum, D. R., R. J. Chang, J. Lu, W. Vale, J. Rivier and H. L. Judd (1982). "Medical oophorectomy" using a long-acting GNRH agonist—a possible new approach to the treatment of endometriosis." J. Clin. Endocrinol. Metab. 54: 1081-1083.

Michalska, D., J. J. Stepan, B. R. Basson and I. Pavo (2006). "The effect of raloxifene after discontinuation of long-term alendronate treatment of postmenopausal osteoporosis." J Clin Endocrinol Metab 91(3): 870-7.

Moghissi, K. S, and C. R. Boyce (1976). "Management of endometriosis with oral medroxyprogesterone acetate." Obstet. Gynecol. 47: 265-267.

Morales, A. J., J. J. Nolan, J. C. Nelson and S. S. Yen (1994). "Effects of replacement dose of dehydroepiandrosterone in men and women of advancing age." J. Clin. Endocrinol. Metab. 78: 1360-1367.

Morales, A. J., R. H. Haubrich, J. Y. Hwang, H. Asakura and S. S. Yen (1998). "The effect of six months treatment with a 100 mg daily dose of dehydroepiandrosterone (DHEA) on circulating sex steroids, body composition and muscle strength in age-advanced men and women." Clin Endocrinol (Oxf) 49(4): 421-32.

Nair, K. S., R. A. Rizza, P. O'Brien, K. Dhatariya, K. R. Short, A. Nehra, J. L. Vittone, G. G. Klee, A. Basu, R. Basu, C. Cobelli, G. Toffolo, C. Dalla Man, D. J. Tindall, L. J. Melton, 3rd, G. E. Smith, S. Khosla and M. D. Jensen (2006). "DHEA in elderly women and DHEA or testosterone in elderly men." N Engl J Med 355(16): 1647-59.

Need, A. G., M. Horowitz, A. Bridges, H. A. Morris and B. E. Nordin (1989). "Effects of nandrolone decanoate and antiresorptive therapy on vertebral density in osteoporotic postmenopausal women." Arch. Intern. Med. 149: 57-60.

Nestler, J. E., C. O. Barlascini, J. N. Clore and W. G. Blackard (1988). "Dehydroepiandrosterone reduces serum low density lipoprotein levels and body fat but does not alter insulin sensitivity in normal men." J. Clin. Endocrinol. Metab. 66: 57-61.

Nestor, J. J. J., T. L. Ho, R. Tahilramani, B. L. Horner, R. A. Simpson, G. H. Jones, G. I. McRae and B. H. Vickery (1984). LHRH Agonists and Antagonists Containing Very Hydrophobic Amino Acids. LHRH and its analogs. B. H.

Vickery, J. J. Nestor and E. S. E. Hafez. Lancaster, England, MTP Press: 22-33.

Noble, L. S., E. R. Simpson, A. Johns and S. E. Bulun (1996). "Aromatase expression in endometriosis." J Clin Endocrinol Metab 81(1): 174-9.

Noble, L. S., K. Takayama, K. M. Zeitoun, J. M. Putman, D. A. Johns, M. M. Hinshelwood, V. R. Agarwal, Y. Zhao, B. R. Carr and S. E. Bulun (1997). "Prostaglandin E2 stimulates aromatase expression in endometriosis-derived stromal cells." J Clin Endocrinol Metab 82(2): 600-6.

Notelovitz, M., N. Watts, C. Timmons, A. Addison, B. Wiita and L. Downey (1992). Effects of estrogen plus low dose androgen vs estrogen alone on menopausal symptoms in oophorectomized/hysterectomized women. North Am. Menopause Soc., Cleveland: 101.

Pye, J. K., R. E. Mansel and L. E. Hughes (1985). "Clinical experience of drug treatments for mastalgia." Lancet 2: 373-377.

Rasmussen, K. R., M. J. Arrowood and M. C. Healey (1992). "Effectiveness of dehydroepiandrosterone in reduction of cryptosporidial activity in immunosuppressed rats." Antimicrob. Agents Chemother. 36: 220-222.

Riis, B., C. Christiansen, J. Johansen and J. Jacobson (1990). "Is it possible to prevent bone loss in young women treated with luteinizing hormone-releasing hormone agonists?" J. Clin. Endocrinol. Metab. 70: 920-924.

Riva, H. L., J. H. Wilson and D. M. Kowasaki (1961). "Effect of norethynodrel on endometriosis." Am. J. Obstet. Gynecol. 82: 109-118.

Rivier, C., J. Rivier and W. Vale (1979). "Chronic effects of [D-Trp6,Pro9-NEt]luteinizing hormone-releasing factor on reproductive processes in the male rat." Endocrinology 105: 1191-1201.

Rivier, J., C. Rivier, M. Perrin, J. Porter and W. Vale (1984). LHRH analogs as antiovulatory agents. LHRH and Its Analogs. B. H. Vickery, J. J. Nestor Jr. and E. S. E. Hafez. Lancaster, MTP Press: 11-22.

Rock, J. A., J. A. Truglia, R. J. Caplan and Z. E. S. Group (1993). "Zoladex (goserelin acetate implant) in the treatment of endometriosis: a randomized comparison with danazol." Obstet. Gynecol. 82: 198-205.

Ruttimann, J. (2008). "The menopause brain effect: Can hormone therapy help?" Endocrine News: 15-16.

Sampson, J. A. (1921). "Perforating hemorrhagic (chocolate) cysts of the ovary." Archives of Surgery 3: 245-250.

Schriock, E. D., C. K. Buffington, G. D. Hubert, B. R. Kurtz, A. E. Kitabchi, J. E. Buster and J. R. Givens (1988). "Divergent correlations of circulating dehydroepiandrosterone sulfate and testosterone with insulin levels and insulin receptor binding." J. Clin. Endocrinol. Metab. 66: 1329-1331.

Schwartz, A. G., L. Pashko and J. M. Whitcomb (1986). "Inhibition of tumor development by dehydroepiandrosterone and related steroids." Toxicol. Pathol. 14: 357-362.

Sherwin, B. B. and M. M. Gelfand (1984). "Effects of parenteral administration of estrogen and androgen on plasma hormone levels and hot flushes in the surgical menopause." Am. J. Obstet. Gynecol. 148: 552-557.

Sherwin, B. B. and M. M. Gelfand (1985). "Differential symptom response to parenteral estrogen and/or androgen administration in the surgical menopause." Am. J. Obstet. Gynecol. 151: 153-160.

Sherwin, B. B. and M. M. Gelfand (1987). "The role of androgen in the maintenance of sexual functioning in oophorectomized women." Psychosom Med. 49: 397-409.

Sherwin, B. B. (1988). "Affective changes with estrogen and androgen replacement therapy in surgically menopausal women." J. Affect. Disord. 14: 177-187.

Simard, J., C. Labrie, A. Bélanger, S. Gauthier, S. M. Singh, Y. Mérand and F. Labrie (1997). "Characterization of the effects of the novel non-steroidal antiestrogen EM-800 on basal and estrogen-induced proliferation of T-47D, ZR-75-1 and MCF-7 human breast cancer cells in vitro." Int. J. Cancer 73: 104-112.

Simard, J., R. Sanchez, D. Poirier, S. Gauthier, S. M. Singh, Y. Mérand, A. Bélanger, C. Labrie and F. Labrie (1997). "Blockade of the stimulatory effect of estrogens, OH-Tamoxifen, OH-Toremifene, Droloxifene and Raloxifene on alkaline phosphatase activity by the antiestrogen EM-800 in human endometrial adenocarcinoma Ishikawa cells." Cancer Res. 57: 3494-3497.

Simon, J. A. (2009). "Vulvovaginal atrophy: new and upcoming approaches." Menopause 16(1): 5-7.

Sourla, A., S. Luo, C. Labrie, A. Bélanger and F. Labrie (1997). "Morphological changes induced by six-month treatment of intact and ovariectomized mice with tamoxifen and the pure antiestrogen EM-800." Endocrinology 138: 5605-5617.

Studd, J. W. W., W. P. Collins, S. Chakravarti, J. R. Newton, D. Oram and A. Parsons (1977). "Oestradiol and testosterone implants in the treatment of psychosexual problems in the post-menopausal women." British Journal of Obstetrics and Gynaecology. 84: 314-315.

Sun, H. S., K. Y. Hsiao, C. C. Hsu, M. H. Wu and S. J. Tsai (2003). "Transactivation of steroidogenic acute regulatory protein in human endometriotic stromalcells is mediated by the prostaglandin EP2 receptor." Endocrinology 144 (9): 3934-42.

Surrey, E. and H. Judd (1992). "Reduction of vasomotor symptoms and bone mineral density loss with combined norethindrone and long-acting gonadotropin-releasing hormone agonist therapy of symptomatic endometriosis: a prospective randomized trial." J. Clin. Endocrinol. Metab. 75: 558-563.

Surrey, E. (1995). "Steroidal and nonsteroidal "add-back" therapy: extending safety and efficacy of gonadotropin-releasing hormone agonists in the gynecology patients." Fertil. Steril. 64: 673-685.

Suzuki, T., N. Suzuki, R. A. Daynes and E. G. Engleman (1991). "Dehydroepiandrosterone enhances IL2 production and cytotoxic effector function of human T cells." Clin. Immunol. Immunopathol. 61: 202-211.

Takayama, K., K. Zeitoun, R. T. Gunby, H. Sasano, B. R. Carr and S. E. Bulun (1998). "Treatment of severe post-menopausal endometriosis with an aromatase inhibitor." Fertil Steril 69(4): 709-13.

Tchernof, A., J. P. Després, A. Bélanger, A. Dupont, D. Prud'homme, S. Moorjani, P. J. Lupien and F. Labrie (1995). "Reduced testosterone and adrenal C19 steroid levels in obese men." Metabolism 44: 513-519.

Tremblay, A., G. B. Tremblay, C. Labrie, F. Labrie and V. Giguère (1998a). "EM-800, a novel antiestrogen, acts as a pure antagonist of the transcriptional functions of estrogen receptors a and b." Endocrinology 139: 111-118.

Tremblay, G. B., A. Tremblay, N. G. Copeland, D. J. Gilbert, N. A. Jenkins, F. Labrie and V. Giguere (1997). "Cloning, chromosomal localization and functional analysis of the murine estrogen receptor b." Mol. Endocrinol. 11: 353-365.

Tremblay, G. B., A. Tremblay, F. Labrie and V. Giguere (1998b). "Ligand-independent activation of the estrogen receptor a and b by mutations of a conserved tyrosine can be abolished by antiestrogens." Cancer Res. 58: 877-881.

Tremblay, G. B., A. Tremblay, F. Labrie and V. Giguère (1999). "Dominant activity of activation function-1 (AF-1) and differential stoichiometric requirements for AF-1 and -2 in the estrogen receptor a-b heterodimeric complex." Mol. Cell. Biol. 19(3): 1919-1927.

Tsai, S. J., M. H. Wu, C. C. Lin, H. S. Sun and H. M. Chen (2001). "Regulation of steroidogenic acute regulatory protein expression and progesterone production in endometriotic stromal cells." J Clin Endocrinol Metab 86(12): 5765-73.

Villareal, D. T. and J. O. Holloszy (2004). "Effect of DHEA on abdominal fat and insulin action in elderly women and men: a randomized controlled trial." JAMA 292(18): 2243-8.

Willson, T. M., J. D. Norris, B. L. Wagner, I. Asplin, P. Baer, H. R. Brown, S. A. Jones, B. Henke, H. Sauls, S. Wolfe, D. C. Morris and D. P. McDonnell (1997). "Dissection of the molecular mechanism of action of GW5638, a novel estrogen receptor ligand, provides insights into the role of estrogen receptor in bone." Endocrinology 138(9): 3901-3911.

Women's Health Initiative (2002). "Risks and benefits of estrogen plus progestin in healthy postmenopausal women." JAMA 288: 321-333.

Yang, S., Z. Fang, T. Suzuki, H. Sasano, J. Zhou, B. Gurates, M. Tamura, K. Ferrer and S. Bulun (2002). "Regulation of aromatase P450 expression in endometriotic and endometrial stromal cells by CCAAT/enhancer binding proteins (C/EBPs): decreased C/EBPbeta in endometriosis is associated with overexpression of aromatase." J Clin Endocrinol Metab 87(5): 2336-45.

Zeitoun, K., K. Takayama, M. D. Michael and S. E. Bulun (1999). "Stimulation of aromatase P450 promoter (II) activity in endometriosis and its inhibition in endometrium are regulated by competitive binding of steroidogenic factor-1 and chicken ovalbumin upstream promoter transcription factor to the same cis-acting element." Mol Endocrinol 13(2): 239-53.

Zumoff, B., J. Levin, R. S. Rosenfeld, M. Markham, G. W. Strain and D. K. Fukushima (1981). "Abnormal 24-hr mean plasma concentrations of dehydroepiandrosterone and dehydroisoandrosterone sulfate in women with primary operable breast cancer." Cancer Res. 41: 3360-3363.

Overview

While there is no aromatase permitting the transformation of DHEA into estradiol in normal endometrium, aromatase is expressed in endometriosis. See Kitawaki, J., T. Noguchi et al, (1997) "Expression of aromatase cytochrome P450 protein and messenger ribonucleic acid in human endometriotic and adenomyotic tissues but not in normal endometrium" Biol. Reprod. 57(3): 514-19; Balun, S. E, S. Yang et al, (2001) Role of aromatase in endometrial disease" J. Steroid Biochem. Mol. Biol. 79(1-5): 19-25; Fang, Z., S. Yang et al (2002) "Genetic or enzymatic disruption of aromatase inhibits growth of ectopic uterine tissue," J. Clin. Endocrin. Metab. 87(7): 3460-6. Applicant here proposes to provide selective estrogen receptor modulator (SERM) to block the action of estrogens made locally in endometriotic tissue as a combination therapy with inhibition of ovarian hormonal secretions. In some embodiments, the presence of the SERM permits the further administration of exogenous sex steroid precursor such as DHEA to obtain the benefits of such precursor noted infra.

Beneficial Effects of SERMs

Acolbifene, a SERM of the present invention, is a benzopyran derivative originally developed as pure antiestrogen for the treatment of breast cancer (Gauthier, Caron et al. 1997; Luo, Martel et al. 1997a; Luo, Martel et al. 1997b; Luo, Sourla et al. 1997; Simard, Labrie et al. 1997; Simard, Sanchez et al. 1997; Tremblay, Tremblay et al. 1997; Couillard, Gutman et al. 1998; Couillard, Labrie et al. 1998; Luo, Labrie et al. 1998; Luo, Stojanovic et al. 1998; Tremblay, Tremblay et al. 1998a; Tremblay, Tremblay et al. 1998b; Tremblay, Tremblay et al. 1999). EM-800 is an inactive precursor quantitatively transformed into EM-652, the active compound, in intact cells as well as in vivo. Acolbifene (EM-1538) is the hydrochloride salt of EM-652.

This orally active antiestrogen shows pure antiestrogenic activity in the mammary gland and endometrial epithelium in the rat, monkey, and mouse (Luo, Martel et al. 1997b; Sourla, Luo et al. 1997) as well as in human breast and endometrial human breast cancer carcinoma cells in vitro (Gauthier, Caron et al. 1997; Simard, Labrie et al. 1997) and xenografts in vivo in nude mice (Couillard, Gutman et al. 1998).

EM-652, the active metabolite of EM-800 and acolbifene, is the compound having the highest known affinity for the human estrogen receptor. EM-652 is thus 1.5 to 3.0 times more potent than 1713-estradiol and diethylstilbestrol to displace [$^3$H]estradiol from the estrogen receptor in human breast cancer and normal uterine tissue. In the binding assay, EM-652 is 5 times more potent than hydroxytamoxifen, the active metabolite of tamoxifen and 200 times more potent than tamoxifen itself. Depending upon the conditions of the binding assay, EM-652 is 10 to 140 times more potent than the steroidal antiestrogen ICI 182 780, 20 to 85 times more potent than ICI 164 384, 100 to 1500 times more potent than toremifene in competing for the human breast cancer estrogen receptor. The Ki value of the affinity of EM-652 for the human estrogen receptor is at the very low value of 0.05 nM, thus showing the highest affinity so far known for any compound for the estrogen receptor.

As mentioned above, EM-800 (EM-652) shows pure antiestrogenic activity in human endometrial Ishikawa carcinoma cells (Simard, Sanchez et al. 1997). It should be mentioned that Raloxifene, Arzoxifene, Droloxifene, Idoxifene, Toremifene, Ospemifene and Tamoxifen stimulate, to various degrees, the estrogen-sensitive parameter alkaline phosphatase in human endometrial Ishikawa carcinoma cells (Gauthier, Caron et al. 1997; Simard, Sanchez et al. 1997; Labrie, Martel et al. 2010).

Raloxifene, a compound derived from a benzothiophene series of antiestrogens (Black, Sato et al. 1994), has been reported to exert a protective effect on bone loss and have beneficial effects on serum lipids (Black, Sato et al. 1994; Draper, Flowers et al. 1996).

EM-652 is unique among SERMs in having pure antiestrogenic activity in both human breast and uterine cells (Gauthier, Caron et al. 1997; Simard, Labrie et al. 1997; Simard, Sanchez et al. 1997; Couillard, Gutman et al. 1998). As mentioned above, EM-652 appears to be the most potent SERM in the prevention of loss of bone mineral density and inhibitor of serum cholesterol in the rat.

Despite being the only compound having pure antiestrogenic activity in the mammary gland and endometrium as summarized above, EM-652, due to its beneficial effects on bone and blood lipids, can be classified as a selective estrogen receptor modulator (SERM), as originally proposed for Raloxifene (Draper, Flowers et al. 1995; Kauffman and Bryant 1995). In fact, EM-800 has been shown to inhibit bone resorption after ovariectomy in the rat, a maximal effect being already achieved at 0.01 mg/kg, compared to 0.1 mg/kg for Raloxifene (Martel, Sourla et al. 1998). A similar high potency of EM-800 (EM-652) on serum cholesterol has been found in the rat (Martel, Sourla et al. 1998). Moreover, at the daily oral dose of 5, 10, 20 and 40 mg, for 2 weeks, in postmenopausal women, EM-800 (EM-652) causes a 10% decrease in total serum cholesterol while a 15% decrease in serum triglyceride levels is already observed at 1 week (Labrie et al., unpublished data).

Beneficial Effects of Sex Steroid Precursors

Humans, with some other primates, are unique among animal species in having adrenals that secrete large amounts of the inactive precursor steroids DHEA and especially DHEA-S, which are converted into potent androgens and/or estrogens in peripheral tissues. Plasma DHEA-S levels are 200-1000 times higher than those of testosterone in adult men and 5000 to 25000 times higher than those of estradiol, in adult women, thus providing a large supply of substrate for the formation of androgens and/or estrogens. As mentioned above, the local synthesis and action of sex steroids in peripheral target tissues has been called intracrinology; the examples chosen included DHEA and androstenedione (Labrie, Bélanger et al. 1988; Labrie 1991).

Changes of Serum DHEA with Age and High Variability

The secretion of DHEA markedly decreases from the age of 30 years, with an average loss of 60% already observed at time of menopause (Labrie, Bélanger et al. 2006; Labrie, Luu-The et al. 2005; Labrie, Luu-The et al. 2003; Labrie, Bélanger et al. 1997b). This marked reduction in the secretion of DHEA by the adrenals during aging (Labrie, Bélanger et al. 1997b) results in a parallel fall in the formation of androgens and estrogens in peripheral target tissues, a situation believed to be associated with a series of medical problems of menopause (insulin resistance (Coleman, Leiter et al. 1982), fat accumulation (Tchernof, Després et al. 1995), bone loss, muscle loss, type 2 diabetes, vaginal atrophy and skin atrophy (Labrie, Luu-The et al. 2005; Simon 2009; Diamond, Cusan et al. 1996; Labrie, Diamond et al. 1997; Labrie 2007), loss of memory and cognition (Ruttimann 2008) and others. Some of these problems which are well recognized after menopause can also become apparent before menopause, bone loss, vaginal dryness and hot flashes being examples. FIG. 1 shows a decrease in DHEA levels with age.

Figure 2:
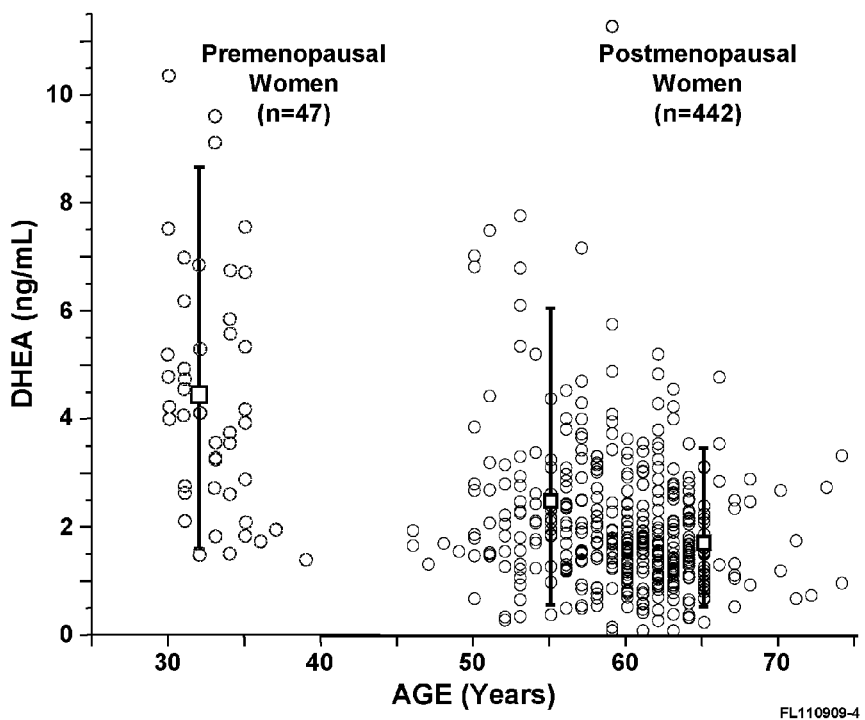
FIG. 2 is an illustration of the wide variability of serum DHEA levels in normal women ages 30 to 40 years and 50 to 75 years. Data are presented individually as well as by means and 5%-95% percentiles (Labrie et al., unpublished data).

In addition to markedly decreasing with age, the serum levels of DHEA are highly variable, with some women having low DHEA levels even during reproductive years. See FIG. 2.

Significant Amounts of DHEA are Secreted by the Human Ovary

A most important recent observation is that the ovary secretes a significant amount of DHEA. Accordingly, a treatment which stops ovarian estrogen secretion as achieved by the use of an LHRH agonist or antagonist as part of this invention, should also decrease the secretion of DHEA from the ovary in the general circulation, thus adding to the lack of sex steroid activity in women older than 30 years (FIG. 1). Moreover, our recent data show that all androgens in women originate from DHEA and that the human ovary does not directly secrete androgens which are important for normal endocrine physiology in women (Labrie, Martel et al. 2011). In fact, women have about 40% as much androgens as men (Labrie 2007).

Since, there is no feedback mechanism to increase the secretion of DHEA when the serum concentration of the steroid is low, women with a low secretion rate of DHEA remain deficient in sex steroids for the rest of their life in the absence of replacement therapy with exogenous DHEA.

Data were obtained from 442 intact postmenopausal women aged 46 to 74 years (mean: 59.9 years; median: 60.5 years), 71 postmenopausal women with previous bilateral ovariectomy aged 42 to 72 years (mean: 60.6 years; median: 62.0 years) and 47 premenopausal normal cycling women aged 30 to 39 years (mean and median: 33 years). Steroid levels were measured in blood samples collected at screening or at Day 1 from women participating to various clinical trials. All samples were collected prior to the administration of any investigational drug. The women participated to clinical trials after IRB approval and having given written informed consent.

Blood samples were processed for serum preparation and kept frozen at −20° C. or lower until measurement of steroids. The serum steroid levels of DHEA, DHEA-S, androst-5-ene-3β,17β-diol (5-diol), androstenedione (4-dione), testosterone (testo), dihydrotestosterone (DHT), estradiol (E2), estrone (E1), estrone sulfate (E1-S), androsterone glucuronide (ADT-G), androstane-3α,17β-diol-3-glucuronide (3α-diol-3G) and 3α-diol-17G were measured by mass spectrometry, as previously described (Labrie, Bélanger et al. 2006; Labrie, Bélanger et al. 2007; Labrie, Cusan et al. 2009). Details about performance of the assays, as well as precision and sensitivity can be found in (Labrie, Bélanger et al. 2006) and (Labrie, Cusan et al. 2008).

Descriptive statistics presented in Table 1 were performed using SAS software. Statistical significance based on a comparison of mean steroid levels between the intact and ovariectomized postmenopausal women was determined using a t-test within SAS software (Table 1).

TABLE 1

Serum steroid levels in intact and ovariectomized postmenopausal women as well as in normal cycling women

| STATUS | VALUE | DHEA (ng/mL) | DHEA-S (µg/mL) | 5-DIOL (ng/mL) | 4-DIONE (ng/mL) | TESTO (ng/mL) | DHT (ng/mL) | ADT-G (ng/mL) |
|---|---|---|---|---|---|---|---|---|
| 46-74 YEAR-OLD | MEAN | 2.03 | 0.63 | 0.27 | 0.39 | 0.14 | 0.037 | 15.89 |
| POSTMENOPAUSAL | SD | 1.33 | 0.41 | 0.15 | 0.20 | 0.08 | 0.026 | 11.88 |
| INTACT WOMEN | SEM | 0.06 | 0.02 | 0.01 | 0.01 | 0.004 | 0.001 | 0.57 |
| (HAVING 2 OVARIES) | Median | 1.73 | 0.56 | 0.25 | 0.35 | 0.13 | 0.03 | 12.99 |
| (n = 442) | $5^{th}$-$95^{th}$ centiles | 0.55-4.34 | 0.15-1.38 | 0.10-0.55 | 0.17-0.68 | 0.06-0.27 | 0.01-0.08 | 3.87-39.67 |
| | (MIN-MAX) | (0.10-11.19) | (0.04-3.43) | (0.03-0.93) | (0.07-2.09) | (0.02-0.83) | (0.01-0.32) | (1.00-91.27) |
| | $95^{th}$centile/$5^{th}$centile | 7.89 | 9.20 | 5.50 | 4.00 | 4.50 | 8.00 | 10.25 |
| 42-72 YEAR-OLD | MEAN | 1.66* | 0.51* | 0.23* | 0.35 | 0.11** | 0.027** | 13.03 |
| POSTMENOPAUSAL | SD | 1.04 | 0.39 | 0.14 | 0.17 | 0.05 | 0.018 | 10.85 |
| OVX WOMEN | SEM | 0.12 | 0.05 | 0.02 | 0.02 | 0.006 | 0.002 | 1.29 |
| (WITHOUT OVARIES) | Median | 1.42 | 0.42 | 0.21 | 0.33 | 0.10 | 0.02 | 10.41 |

TABLE 1-continued

Serum steroid levels in intact and ovariectomized postmenopausal women as well as in normal cycling women

| | | | | | | | | |
|---|---|---|---|---|---|---|---|---|
| (n = 71) | | $5^{th}$-$95^{th}$ centiles | 0.42-3.59 | 0.13-1.00 | 0.10-0.48 | 0.15-0.68 | 0.03-0.19 | 0.01-0.06 | 2.95-35.75 |
| | | (MIN-MAX) | (0.16-4.80) | (0.04-2.10) | (0.05-0.72) | (0.12-0.94) | (0.03-0.29) | (0.01-0.10) | (1.00-59.20) |
| | | $95^{th}$centile/$5^{th}$centile | 8.55 | 7.69 | 4.80 | 4.53 | 6.33 | 6.00 | 12.12 |
| | % Difference of Mean Conc in OVX vs INT [(Mean OVX/Mean INTACT) × 100] − 100 | | −18.2% | −19.0% | −14.8% | −10.3% | −21.4% | −27.0% | −18.0% |
| 42-74 YEAR-OLD POSTMENOPAUSAL WOMEN (n = 513) (INTACT (n = 442) and OVARIECTOMIZED (n = 71)) | | MEAN | 1.98 | 0.62 | 0.26 | 0.39 | 0.13 | 0.035 | 15.50 |
| | | SD | 1.30 | 0.41 | 0.15 | 0.19 | 0.08 | 0.026 | 11.77 |
| | | SEM | 0.06 | 0.02 | 0.01 | 0.01 | 0.003 | 0.001 | 0.52 |
| | | Median | 1.70 | 0.54 | 0.25 | 0.35 | 0.12 | 0.03 | 12.82 |
| | | $5^{th}$-$95^{th}$ centiles | 0.51-4.28 | 0.14-1.38 | 0.10-0.55 | 0.16-0.68 | 0.05-0.27 | 0.01-0.07 | 3.82-39.67 |
| | | (MIN-MAX) | (0.10-11.19) | (0.04-3.43) | (0.03-0.93) | (0.07-2.09) | (0.02-0.83) | (0.01-0.32) | (1.00-91.27) |
| | | $95^{th}$centile/$5^{th}$centile | 8.39 | 9.86 | 5.50 | 4.25 | 5.40 | 7.00 | 10.38 |
| 30-39 YEAR-OLD PREMENOPAUSAL WOMEN (n = 47) | | MEAN | 4.47 | 1.27 | 0.49 | 0.96 | 0.18 | 0.07 | 40.21 |
| | | SD | 2.19 | 0.62 | 0.2 | 0.35 | 0.07 | 0.03 | 29.31 |
| | | SEM | 0.32 | 0.09 | 0.03 | 0.05 | 0.01 | 0.01 | 4.28 |
| | | Median | 4.14 | 1.04 | 0.44 | 0.92 | 0.17 | 0.07 | 31.62 |
| | | $5^{th}$-$95^{th}$ centiles | 1.53-9.14 | 0.56-2.65 | 0.25-0.84 | 0.45-1.64 | 0.06-0.31 | 0.03-0.14 | 12.17-118.20 |
| | | (MIN-MAX) | (1.41-10.37) | (0.45-2.71) | (0.25-0.96) | (0.31-1.77) | (0.05-0.32) | (0.03-0.17) | (6.86-132.60) |
| | | $95^{th}$centile/$5^{th}$centile | 5.97 | 4.73 | 3.36 | 3.64 | 5.17 | 4.67 | 9.71 |

| | STATUS | VALUE | $3G_1$ (ng/mL) | $17G_2$ (ng/mL) | $E_1$ (pg/mL) | $E_2$ (pg/mL) | $E_1$-S (ng/mL) |
|---|---|---|---|---|---|---|---|
| | | | | | (n = 438) | (n = 438) | (n = 438) |
| | 46-74 YEAR-OLD POSTMENOPAUSAL INTACT WOMEN (HAVING 2 OVARIES) (n = 442) | MEAN | 0.72 | 0.62 | 15.73 | 3.32 | 0.19 |
| | | SD | 0.52 | 0.51 | 8.56 | 2.43 | 0.17 |
| | | SEM | 0.02 | 0.02 | 0.41 | 0.12 | 0.01 |
| | | Median | 0.61 | 0.48 | 14.27 | 2.77 | 0.15 |
| | | $5^{th}$-$95^{th}$ centiles | 0.25-1.70 | 0.25-1.66 | 5.28-29.10 | 1.00-7.79 | 0.04-0.47 |
| | | (MIN-MAX) | (0.14-3.29) | (0.11-3.51) | (2.86-83.49) | (0.40-22.59) | (0.02-1.58) |
| | | $95^{th}$centile/$5^{th}$centile | 6.80 | 6.64 | 5.51 | 7.79 | 11.75 |
| | 42-72 YEAR-OLD POSTMENOPAUSAL OVX WOMEN (WITHOUT OVARIES) (n = 71) | MEAN | 0.64 | 0.52 | 15.37 | 2.77* | 0.16* |
| | | SD | 0.60 | 0.39 | 7.19 | 1.70 | 0.14 |
| | | SEM | 0.07 | 0.05 | 0.85 | 0.20 | 0.02 |
| | | Median | 0.47 | 0.31 | 13.80 | 2.22 | 0.11 |
| | | $5^{th}$-$95^{th}$ centiles | 0.25-1.96 | 0.25-1.32 | 8.18-28.82 | 1.00-6.58 | 0.04-0.42 |
| | | (MIN-MAX) | (0.19-3.81) | (0.19-2.15) | (4.00-48.36) | (0.47-8.17) | (0.01-0.63) |
| | | $95^{th}$centile/$5^{th}$centile | 7.84 | 5.28 | 3.52 | 6.58 | 10.50 |
| | % Difference of Mean Conc in OVX vs INT [(Mean OVX/Mean INTACT) × 100] − 100 | | −11.1% | −16.1% | −2.3% | −16.6% | −15.8% |
| | | | | | (n = 509) | (n = 509) | (n = 509) |
| | 42-74 YEAR-OLD POSTMENOPAUSAL WOMEN (n = 513) (INTACT (n = 442) and OVARIECTOMIZED (n = 71)) | MEAN | 0.71 | 0.61 | 15.68 | 3.24 | 0.19 |
| | | SD | 0.53 | 0.50 | 8.38 | 2.35 | 0.17 |
| | | SEM | 0.02 | 0.02 | 0.37 | 0.10 | 0.01 |
| | | Median | 0.59 | 0.45 | 14.19 | 2.70 | 0.14 |
| | | $5^{th}$-$95^{th}$ centiles | 0.25-1.70 | 0.25-1.60 | 5.94-28.98 | 1.00-7.55 | 0.04-0.47 |
| | | (MIN-MAX) | (0.14-3.81) | (0.11-3.51) | (2.86-83.49) | (0.40-22.59) | (0.01-1.58) |
| | | $95^{th}$centile/$5^{th}$centile | 6.80 | 6.40 | 4.88 | 7.55 | 11.75 |
| | 30-39 YEAR-OLD PREMENOPAUSAL WOMEN (n = 47) | MEAN | 1.21 | 1.43 | 53.96 | 82.05 | 1.19 |
| | | SD | 0.83 | 0.93 | 23.28 | 42.19 | 0.93 |
| | | SEM | 0.12 | 0.14 | 3.40 | 6.15 | 0.14 |
| | | Median | 1.06 | 1.35 | 49.47 | 71.38 | 0.87 |
| | | $5^{th}$-$95^{th}$ centiles | 0.25-2.78 | 0.25-2.56 | 23.74-87.46 | 22.00-159.97 | 0.31-3.50 |
| | | (MIN-MAX) | (0.25-4.33) | (0.25-5.71) | (18.27-123.50) | (17.71-181.14) | (0.21-4.40) |
| | | $95^{th}$centile/$5^{th}$centile | 11.12 | 10.24 | 3.68 | 7.27 | 11.29 |

[1]Androstane-3α,17β-diol-3G
[2]Androstane-3α,17β-diol-17G
*$p < 0.05$;
**$p < 0.01$; OVX vs INTACT As shown in Table 1, the present data show that the postmenopausal ovary secretes approximately 18% of total DHEA in this age group. The lower serum levels of DHEA in OVX compared to intact postmenopausal women observed in the present study can be best explained by secretion of the corresponding amount of DHEA by the ovary into the circulation. This DHEA of ovarian origin is then submitted to the same intracrine mechanisms as the DHEA of adrenal origin.

Figure 3:
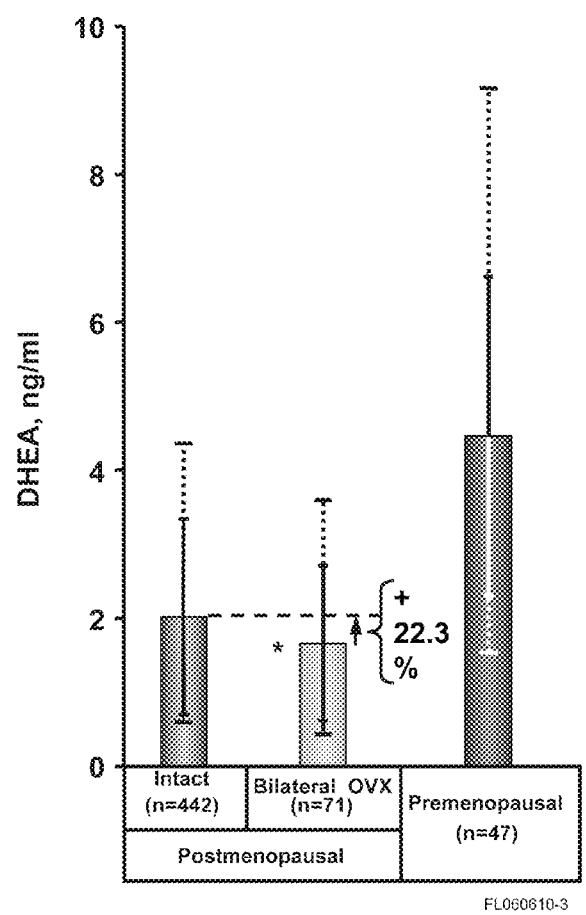
FIG. 3 is a bar chart showing serum DHEA is 22.3% higher in intact compared to oophorectomized postmenopausal women aged 42 to 74 years in a sampler whose number is shown on the X axis.
Figure 4:
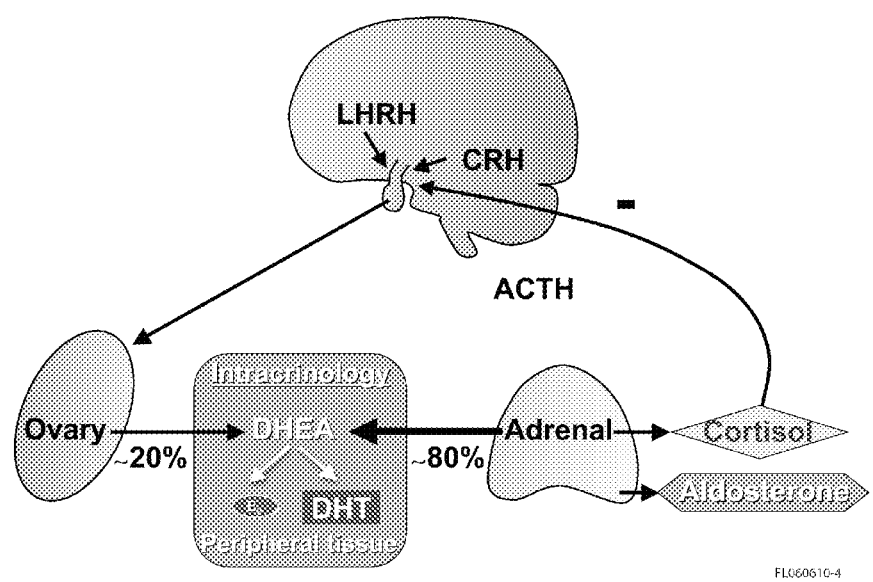
FIG. 4 is a schematic representation of the unique source of sex steroids in postmenopausal women, namely DHEA. After menopause, all estrogens and androgens are made locally in peripheral target intracrine tissues from adrenal (80%) or ovarian (20%) DHEA. During the whole lifetime, androgens are exclusively derived from adrenal and ovarian DHEA. The amount of sex steroids made in peripheral target tissues depends upon the level of the steroid-forming enzymes specifically expressed in each tissue.
Figure 5:
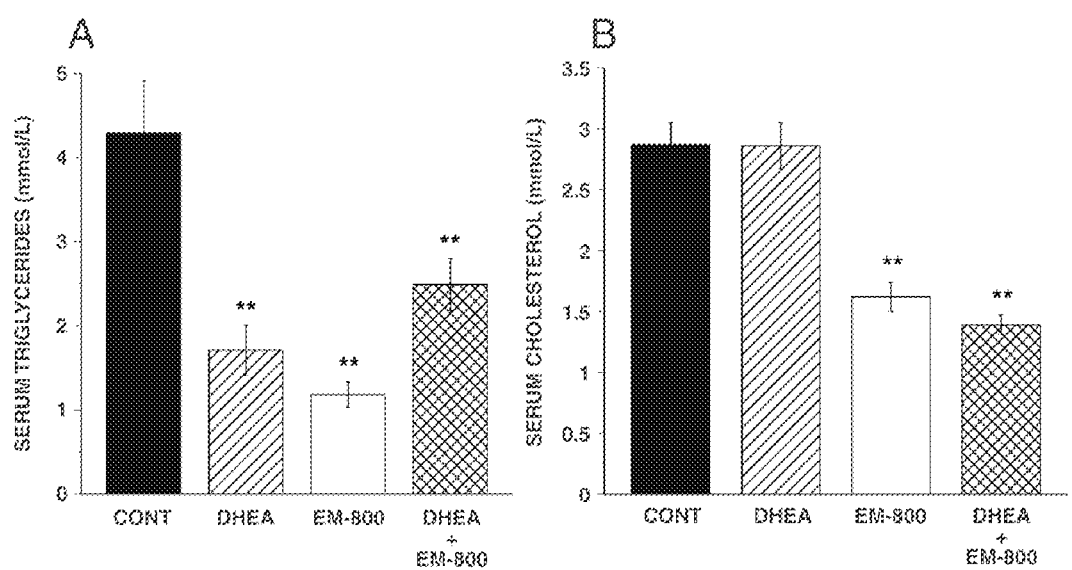
FIG. 5 is a bar graph comparing the effect of treatment with DHEA (10 mg, percutaneously, once daily) or EM-800 (precursor of EM-652 which also derives from EM-652.HCl (Acolbifene)) (75 μg, orally, once daily) alone or in combination for 9 months on serum triglyceride (A) and cholesterol (B) levels in the rat. Data are expressed as the means±SEM. **: P<0.01 experimental versus respective control.

Because there is no regulatory mechanism to increase DHEA secretion when serum DHEA is low, it seems that the only means of correcting this deficiency is to supply exogenous DHEA to compensate for the absence of feedback control of DHEA secretion. The 18% but parallel lower serum levels of DHEA and all its metabolites found in OVX women (FIG. 3), including $E_2$ and testosterone, suggest that the postmenopausal ovary secretes 18% of total DHEA in the 42- to 74-year-old age group with no significant amounts of $E_2$ or testosterone secreted directly by the ovary (FIG. 4).

There is no reason to believe that the situation of a significant contribution (~18%) of the postmenopausal ovary to the total pool of circulating DHEA would be lower at premenopause.

We feel that the increased understanding of androgen and estrogen formation and action in peripheral target tissues called intracrinology (Labrie 1991; Labrie, Simard et al. 1992a; Labrie, Simard et al. 1992b; Labrie, Durocher et al. 1995; Luu-The, Dufort et al. 1995; Labrie, Simard et al. 1996; Labrie, Bélanger et al. 1997a; Labrie, Bélanger et al. 1997b; Labrie, Diamond et al. 1997; Labrie, Luu-The et al. 1997) as well as our recent observations indicating the predominant role of androgens over that of estrogens in the prevention of bone loss after ovariectomy in the rat (Martel, Sourla et al. 1998) and the observation of a similar situation in post-menopausal women (Labrie, Diamond et al. 1997) have paved the way for a timely and potentially highly significant progress in the field of sex steroid replacement therapy. Such a possibility is well supported by our observations and that of others of a series of beneficial effects of DHEA observed in postmenopausal women (Morales, Nolan et al. 1994; Diamond, Cusan et al. 1996; Labrie, Diamond et al. 1997; Labrie 2007, 2010; Labrie, Archer et al. 2009a, 2009b, 2009c), a situation analogous to medical castration induced by LHRH agonists or antagonists for the treatment of endometriosis.

A very compelling demonstration of the efficacy and safety of DHEA has recently been obtained in a pivotal phase III, placebo-controlled, randomized clinical trial in which postmenopausal women suffering from vaginal atrophy received daily DHEA or placebo intravaginally for 3 months. A rapid and very marked improvement of all the symptoms and signs of vaginal atrophy was observed, with no change in circulating estradiol or testosterone. An additional benefit not seen with estrogens was the finding of a significant improvement of all domains of sexual dysfunction, namely desire, arousal, orgasm and pleasure (Labrie, Archer et al. 2009a, 2009b).

Estrogen Formation in Endometriosis

While the enzymes required for estrogen formation, especially aromatase, are absent in the normal human endometrium (Bulun, Lin et al. 2005; Baxendale, Reed et al. 1981), aromatase is highly expressed and local estrogen production is present in endometriotic tissue ((Kitawaki, Noguchi et al. 1997; Zeitoun, Takayama et al. 1999; Bulun, Yang et al. 2001; Fang, Yang et al. 2002; Gurates, Sebastian et al. 2002; Yang, Fang et al. 2002). The subsequent introduction of aromatase inhibitors in the treatment of endometriosis successfully) underscored the presence of aromatase in endometriotic tissue(Takayama, Zeitoun et al. 1998; Ailawadi, Jobanputra et al. 2004).

In endometriosis, the prototype abnormality is the presence of significant levels of StAR and aromatase activity and expression of protein and mRNA in the stromal cell component of endometriosis, whereas StAR or aromatase expression was either absent or barely detectable in the eutopic endometrium of disease-free women (Noble, Simpson et al. 1996; Noble, Takayama et al. 1997; Tsai, Wu et al. 2001; Gurates, Sebastian et al. 2002; Sun, Hsiao et al. 2003). The eutopic endometrium of women with endometriosis contains low but significant levels of aromatase mRNA and enzyme activity and represents an intermediate state of this disease. It seems that upon retrograde menstruation and implantation of this inherently abnormal tissue on pelvic peritoneal surfaces, aromatase expression and enzyme activity are amplified by up to 400 times (Noble, Simpson et al. 1996; Noble, Takayama et al. 1997).

What separates normal endometrium from endometriosis, however, is the in vivo lack of StAR and aromatase. Physiologically significant levels of these gene products are not detected in normal endometrial tissue or $PGE_2$-stimulated endometrial stromal cells (Bulun, Lin et al. 2005). Aromatase activity or mRNA could not be induced by $PGE_2$ or cAMP analogs in stromal cells from disease-free women (Noble, Takayama et al. 1997).

Beneficial Effects of Combination of SERM+Sex Steroid Precursor

DHEA is known to prevent the development and to inhibit the growth of dimethylbenz(a)anthracene-induced mammary tumors in the rat (Labrie, Luu-The et al. 2003). DHEA, in addition, inhibits the growth of human breast cancer xenografts in nude mice (Labrie, Luu-The et al. 2003). Thus, in contrast to estrogens and progestins, which exert stimulatory effects, DHEA is expected—as demonstrated in the majority of human breast cancer cell lines—to inhibit both the development and growth of breast cancer in women (Labrie, Luu-The et al. 2003; Labrie 2010, 2006; Labrie, Bélanger et al. 2006).

To avoid the problems illustrated by the WHI study (Women's Health Initiative, JAMA 288: 321-333, 2002) using traditional HRT, it seems logical to use a tissue-specific antiestrogenic/estrogenic (depending on the tissue) compound (SERM) combined with a tissue-targeted androgenic and/or estrogenic replacement therapy at perimenopause and postmenopause. This strategy could be the best or possibly the only way to maintain a physiological balance between androgens and estrogens in each cell of each tissue and simultaneously prevent breast and uterine cancer. Such an objective can potentially be met by combining a SERM with DHEA (Labrie, Luu-The et al. 2005; Labrie, Luu-The et al. 2003; Labrie 2007).

Whereas SERMs have effects in the bone limited to inhibition of bone resorption, DHEA stimulates bone formation through its androgenic or anabolic component (Michalska, Stepan et al. 2006; Martel, Sourla et al. 1998). Such an anabolic or bone-forming effect cannot be achieved with SERMs, bisphosphonates, estrogens or calcitonin, which only decrease the rate of bone resorption. In fact, these antiresorptive therapies do not improve all the characteristics of the normal bone loss, especially the microarchitecture. Whereas the high potency of acolbifene (10-fold higher than raloxifene) on bone has been demonstrated at the preclinical level (Labrie, Labrie et al. 2001), treatment with DHEA has already been observed to increase bone formation in postmenopausal women through an anabolic action (Labrie, Diamond et al. 1997).

In addition to an increase in bone formation, DHEA has also been shown in postmenopausal women to stimulate vaginal maturation, decrease adiposity as well as serum glucose and insulin levels. The effect of DHEA on fat and glucose metabolism described in some studies (Diamond, Cusan et al. 1996; Villareal and Holloszy 2004; Morales, Haubrich et al. 1998) has not been found in other studies (Jankowski, Gozansky et al. 2006; Nair, Rizza et al. 2006). It is also possible that SERMs could exert additional beneficial effects in postmenopausal women. In fact, preclinical data obtained with acolbifene include the following beneficial effects: lowered cholesterol and triglyceride levels, reduced fat accumulation and improved insulin sensitivity (Labrie, Labrie et al. 2001; Labrie 2007).

The combination of a SERM plus DHEA (FIG. 7) could also help controlling hot flashes, through the androgenic effect of DHEA, while preventing breast cancer, uterine cancer, ovarian cancer, bone and muscle loss as well as decreasing fat accumulation, type 2 diabetes and serum cholesterol (Table 2).

TABLE 2

| | URINE | | | SERUM |
|---|---|---|---|---|
| GROUP | CALCIUM (µmol/24 h/100 g) | PHOSPHORUS (µmol/24 h/100 g) | HP/Cr (µmol/mmol) | TALP (IU/L) |
| CONTROL | 23.17 ± 1.55 | 132.72 ± 6.08 | 13.04 ± 2.19 | 114.25 ± 14.04 |
| DHEA (10 mg) | 25.87 ± 3.54 | 151.41 ± 14.57 | 14.02 ± 1.59 | 198.38 ± 30.76* |
| EM-800 (75 µg) | 17.44 ± 4.5 | 102.03 ± 25.13 | 6.81 ± 0.84** | 114.11 ± 11.26 |
| DHEA + EM-800 | 3.71 ± 0.75** | 59.06 ± 4.76** | 4.06 ± 0.28** | 204.38 ± 14.20** |

In this context, it is important to indicate that the absence of a stimulatory effect of DHEA on the normal human endometrium (Labrie, Diamond et al. 1997) eliminates the need to administer a progestin to neutralize the potential effect of estrogens on the endometrium. Concerning the breast, DHEA is known to prevent the development (Luo, Sourla et al. 1997) and to inhibit the growth (Li, Yan et al. 1993) of dimethylbenz(a)anthracene mammary tumors in the rat. DHEA, in addition, inhibits the growth of human breast cancer xenografts in nude mice (Couillard, Labrie et al. 1998). Thus, contrary to estrogens and progestins which exert stimulatory effects, DHEA is expected to inhibit both the development and the growth of breast cancer in women.

Role of Androgens in Bone Physiology

In established osteoporosis, anabolic steroids have been reported to help prevent bone loss (Hennernan and Wallach 1957). Androgen therapy, as observed with nandrolone decanoate, has been found to increase vertebral bone mineral density in postmenopausal women (Need, Horowitz et al. 1989). Although androgens are gaining increasing support due to their unique actions in postmenopausal women, virilizing effects are observed with the use of testosterone (Burger, Hailes et al. 1984; Studd, Collins et al. 1977).

Other Roles of Androgens in Women

It is more and more recognized that the androgens produced from DHEA have multiple beneficial effects in postmenopausal women. The detailed benefits of androgens added to ERT or HRT have been described on general well-being, energy, mood, and general quality of life (Sherwin and Gelfand 1985; Sherwin 1988). Improvements in the major psychologic and psychomatic symptoms, namely irritability, nervousness, memory, and insomnia have been observed following addition of androgens to estrogen replacement therapy (ERT) (Notelovitz, Watts et al. 1991).

Loss of libido and/or sexual satisfaction are common in early postmenopause. The addition of androgens to hormone replacement therapy (HRT) is known to have beneficial effects on these problems (Leiblum, Bachmann et al. 1983; Sherwin and Gelfand 1987; Sherwin 1988). Moreover, a positive correlation has been found in postmenopausal women between sexual behavior and circulating levels of androgens. In addition, androgenic compounds have been found to be beneficial for the treatment of the mastalgia frequently caused by HRT (Pye, Mansel et al. 1985). In fact, estrogen replacement therapy may result in severe breast pain which may lead to discontinuation of therapy. The addition of androgens has been found to be effective in relieving hot flushes in women who had unsatisfactory results with estrogen alone (Sherwin and Gelfand 1984).

Other Benefits of DHEA

The 70 to 95% reduction in the formation of DHEA and DHEA-S by the adrenals during aging results in a dramatic reduction in the formation of androgens and estrogens in peripheral target tissues, which could well be involved in the pathogenesis of age-related diseases such as insulin resistance (Coleman, Leiter et al. 1982; Schriock, Buffington et al. 1988) and obesity (Nestler, Barlascini et al. 1988; MacEwen and Kurzman 1991; Tchernof, Després et al. 1995). Low circulating levels of DHEA-S and DHEA have, in fact, been found in patients with breast cancer (Zumoff, Levin et al. 1981) and DHEA has been found to exert antioncogenic activity in a series of animal models (Schwartz, Pashko et al. 1986; Gordon, Shantz et al. 1987; Li, Yan et al. 1993). DHEA has also been shown to have immuno modulatory effects in vitro (Suzuki, Suzuki et al. 1991) and in vivo in fungal and viral diseases (Rasmussen, Arrowood et al. 1992), including HIV (Henderson, Yang et al. 1992). On the other hand, a stimulatory effect of DHEA on the immune system has been described in postmenopausal women (Casson, Andersen et al. 1993).

Previous Data Obtained with DHEA in Women

As mentioned above, osteoporosis is a major problem among aging women, causing morbidity and mortality, mainly through increased fracture rates (Johnston Jr and Epstein 1981). The use of estrogen replacement therapy requires the addition of progestins to counteract the endometrial proliferation induced by estrogens while both estrogens and progestins could increase the risk of breast cancer (Bardon, Vignon et al. 1985; Colditz, Hankinson et al. 1995). In order to avoid the limitations of standard estrogen (ERT) or hormonal replacement therapy (HRT), we have studied the effect of DHEA administration to 60- to 70-year old women for 12 months on bone mineral density, parameters of bone formation and turnover, serum lipids, glucose and insulin, adipose tissue mass, muscular mass, energy, well-being as well as on vaginal and endometrial histology (Diamond, Cusan et al. 1996; Labrie, Diamond et al. 1997). DHEA was administered percutaneously to avoid first passage of the steroid precursor through the liver.

We have thus evaluated the effect of chronic replacement therapy with a 10% DHEA cream applied once daily for 12 months in 60- to 70-year-old women (N=15). Anthropometric measurements showed no change in body weight but a 9.8% decrease in subcutaneous skin fold thickness at 12 months (p<0.05) (Diamond, Cusan et al. 1996). Bone mass density was increased by 2.3% at the hip, 3.75% at the hip Ward's triangle, and 2.2% at the lumbar spine level (all p<0.05) (Labrie, Diamond et al. 1997). These changes in bone mineral density were accompanied by significant decreases at 12 months of 38% and 22% in urinary hydroxyproline and in plasma bone alkaline phosphatase, respectively (all p<0.05). An increase of 135% over control (p<0.05) in plasma osteocalcin was concomitantly observed.

Measurements of midthigh fat and muscle areas by computed tomography have shown a 3.8% decrease (p<0.05) of femoral fat and a 3.5% increase (p<0.05) in femoral muscular area at 12 months (Diamond, Cusan et al. 1996). There was no significant change in abdominal fat measurements. These changes in body fat and muscular surface areas were associated with a 12% decrease (p<0.05) of fasting plasma glucose and a 17% decrease (p<0.05) in fasting plasma insulin levels. Treatment with DHEA had no undesirable effect on the lipid or lipoprotein profile. In fact, there was an overall trend for a 3% to 10% decrease in total cholesterol and its lipoprotein fractions. Plasma triglycerides were not affected.

The index of sebum secretion was 79% increased after 12 months of DHEA therapy with a return to pretreatment values 3 months after cessation of treatment. DHEA administration stimulated vaginal epithelium maturation in 8 out of 10 women who had a maturation value of zero at the onset of therapy while a stimulation was also seen in the three women who had an intermediate vaginal maturation before therapy. Most importantly, the estrogenic stimulatory effect observed in the vagina was not found in the endometrium which remained completely atrophic in all women after 12 months of DHEA treatment (Labrie, Diamond et al. 1997).

The present data clearly indicate the beneficial effects of DHEA therapy in postmenopausal women through its transformation into androgens and/or estrogens in specific intracrine target tissues without significant side effects. The absence of stimulation of the endometrium by DHEA eliminates the need for progestin replacement therapy, thus avoiding the fear of progestin-induced breast cancer. The observed stimulatory effect of DHEA on bone mineral density and the increase in serum osteocalcin, a marker of bone formation, are of particular interest for the prevention and treatment of osteoporosis and indicate a unique activity of DHEA on bone physiology, namely on bone formation while, ERT and HRT can only reduce the rate of bone loss.

Benefits of Combination of a SERM and DHEA in Women Treated with an LHRH Agonist or Antagonist We have shown that DHEA has beneficial effects on bone in both the female rat (Luo et al., Endocrinology 138: 4435-4444, 1997), and postmenopausal women (Labrie et al., J. Clin. Endocrinol. Metab. 82: 3498-3505, 1997). Thus, in intact female rats, treatment with DHEA increases bone mineral density (BMD) of total skeleton, lumbar spine and femur (Luo et al., Endocrinology 138: 4435-4444, 1997).

Moreover, as illustrated in FIG. 5 to FIG. 8, we have found that the combination of a sex steroid precursor (DHEA) and a SERM (EM-800) not only maintained the stimulatory effect of DHEA on bone formation, but potentiated the inhibitory effect of the SERM (EM-800) alone on bone turnover and resorption as demonstrated by the further decreases in urinary hydroxyproline and calcium excretion when both compounds were combined (Luo, Sourla et al. 1997).

In brief, the above-described data clearly demonstrate the beneficial effects of the combination of a SERM (EM-800) and a sex steroid precursor (DHEA) on the development of mammary carcinoma induced by DMBA as well as the protective effects of such a combination on bone mass and serum lipids. Such data clearly suggest the additional beneficial effects of such a combination for the treatment and prevention of osteoporosis while improving the lipid profile and preventing breast and endometrial cancer.

It is particularly important to indicate that the combination of DHEA and EM-800 exerts unexpected beneficial effects on important biochemical parameters of bone metabolism. In fact, DHEA alone did not affect the urinary hydroxyproline/creatinine ratio, a marker of bone resorption. Moreover, no effect of DHEA alone could be detected on daily urinary calcium or phosphorus excretion (Luo, Sourla et al. 1997). EM-800, on the other hand, decreased the urinary hydroxyproline/creatinine ratio by 48% while, similarly to DHEA, no effect of EM-800 was seen on urinary calcium or phosphorus excretion. EM-800, moreover, had no effect on serum alkaline phosphatase activity, a marker of bone formation while DHEA increased the value of the parameter by about 75% (Luo, Sourla et al. 1997) (Table 2).

One of the unexpected effects of the combination of DHEA and EM-800, thus relates to the urinary hydroxyproline/creatinine ratio, a marker of bone resorption, which was reduced by 69% when both DHEA and EM-800 were combined, this value being statistically different (p<0.01) from the 48% inhibition achieved by EM-800 alone while DHEA alone did not show any effect. Thus, the addition of DHEA to EM-800 increases by 50% of the inhibitory effect of EM-800 on bone reabsorption. Most importantly, another unexpected effect of the addition of DHEA to EM-800 was the approximately 84% decrease in urinary calcium (from 23.17±1.55 to 3.71±0.75 µmol/24 h/100 g (p<0.01) and the 55% decrease in urinary phosphorus (from 132.72±6.08 to 59.06±4.76 µmol/24 h/100 g (p<0.01) respectively (Luo, Sourla et al. 1997) (Table 2).

The present results obtained in the rat clearly demonstrate that DHEA can provide the beneficial effects which are lacking with the use of a selective estrogen receptor modulator (SERM) alone such as EM-800, Raloxifene, etc. While a SERM has effects limited to inhibition of bone resorption, the addition of DHEA is believed to stimulate bone formation (an effect not achieved with a SERM, estrogen, bisphosphonate or calcitonin) and further reduce bone resorption above the effect achieved with EM-652 alone.

Importantly, the combination of EM-800 and DHEA in ovariectomized rats treated for 12 months had beneficial effects on bone morphometry. Trabecular bone volume is particularly important for bone strength and to prevent bone fractures. Thus, in the above-mentioned study, trabecular bone volume of the tibia increased from 4.1±0.7% in ovariectomized rats to 11.9±0.6% (p<0.01) with DHEA alone while the addition of EM-800 to DHEA further increased trabecular bone volume to 14.7±1.4%, a value similar to that found in intact controls (FIG. 6).

Figure 7:
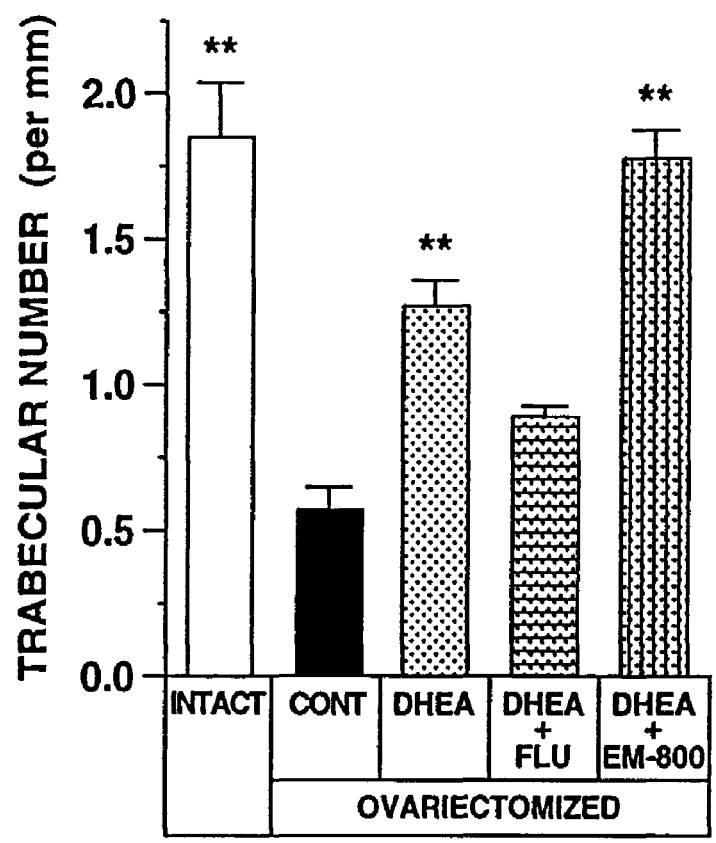
FIG. 7 is a bar graph comparing the effect of 12-month treatment with dehydroepiandrosterone (DHEA) alone or in combination with Flutamide or EM-800 on trabecular number of ovariectomized rats. Intact animals are added as additional controls. Data are presented as mean±SEM **p<0.01 versus OVX Control.

From a value of 0.57±0.08 per mm in ovariectomized rats, treatment with DHEA resulted in a 137% increase in trabecular bone number compared to ovariectomized controls. The stimulatory effect of DHEA thus reached 1.27±0.1 per mm while simultaneous treatment with EM-800 and DHEA resulted in an additional 28% increase in trabecular bone number (p<0.01) compared to that achieved by DHEA alone (FIG. 7). Similarly, the addition of EM-800 to DHEA treatment, resulted in an additional 15% (p<0.05) decrease in trabecular bone separation, compared to that achieved with DHEA alone, thus leading to values not different from those seen in intact controls.

Figure 6:
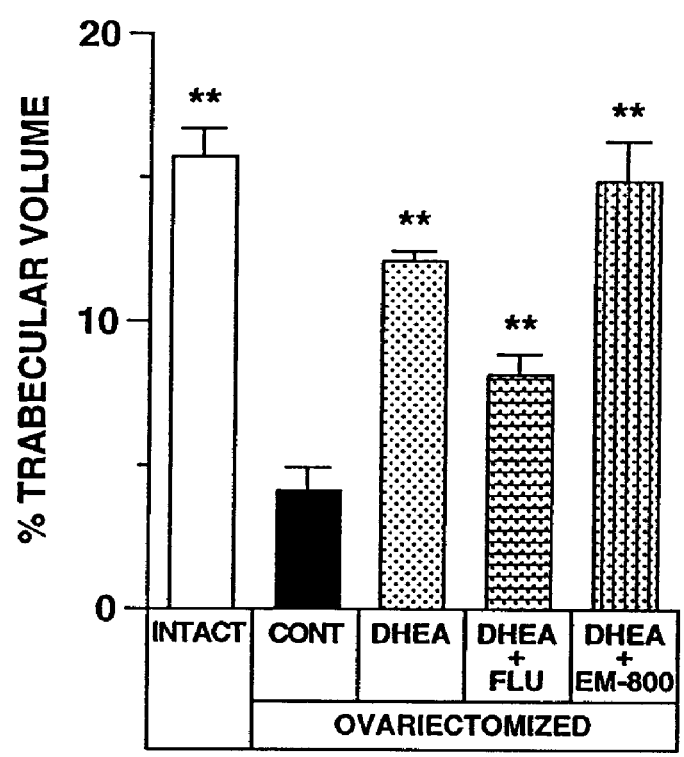
FIG. 6 is a bar graph comparing the effect of 12-month treatment with dehydroepiandrosterone (DHEA) alone or in combination with Flutamide or EM-800 on trabecular bone volume in ovariectomized rats. Intact animals are added as additional controls. Data are presented as mean±SEM **p<0.01 versus OVX Control.
Figure 8:
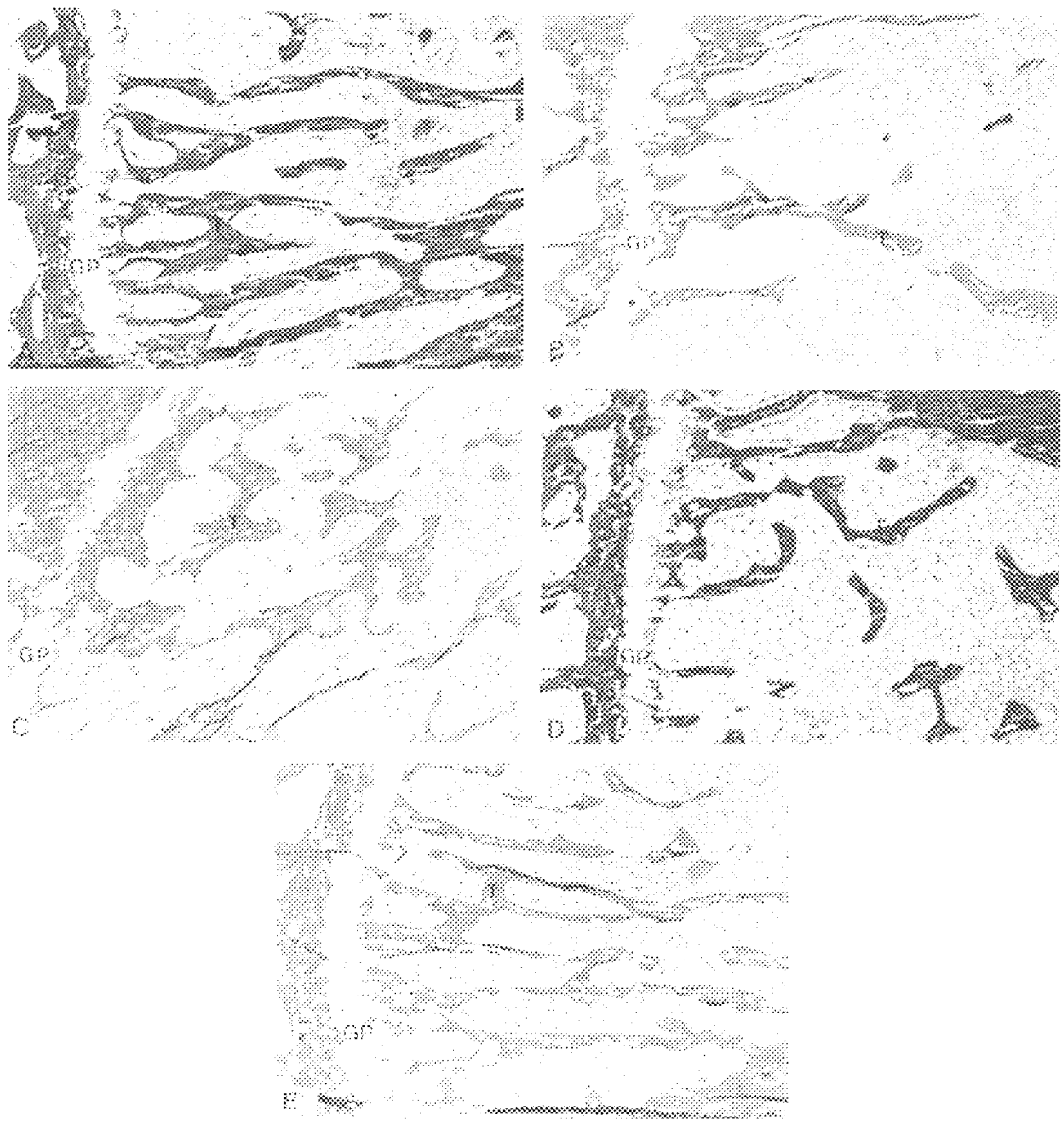
FIG. 8 shows proximal tibia metaphyses from intact control (A), ovariectomized control (B), and ovariectomized rats treated with DHEA alone (C) or in combination with Flutamide (D) or EM-800 (E). Note the reduced amount of trabecular bone (T) in ovariectomized control animals (B), and the significant increase in trabecular bone volume (T) induced after DHEA administration (C). The addition of Flutamide to DHEA partially blocked the effect of DHEA on the trabecular bone volume (D), whereas the combination of DHEA and EM-800 provided complete protection against the ovariectomy-associated bone loss. Modified trichrome Masson-Goldner, magn.×80. T: Trabeculae, GP: Growth Plate.

As complement to the numerical data presented in FIG. 6 and FIG. 7, FIG. 8 illustrates the increase in trabecular bone volume in the proximal tibia metaphysis induced by DHEA in ovariectomized treated animals (C) compared to ovariectomized controls (B), as well as the partial inhibition of the stimulatory effect of DHEA after the addition of Flutamide to DHEA treatment (D). On the other hand, administration of DHEA in combination with EM-800 resulted in a complete prevention of the ovariectomy-induced osteopenia (E), the trabecular bone volume being comparable to that seen in intact controls (A).

In the mentioned study (FIGS. 5-8), the androgenic stimulatory effect of DHEA was observed on almost all the bone histomorphometric parameters studied. DHEA thus resulted in a significant increase in trabecular bone volume as well as trabecular number, while it decreased the intertrabecular area.

In order to achieve more complete estrogen deprivation, a pure antiestrogen is added in the present study to the LHRH agonist or antagonist in order to neutralize the "flare" of ovarian estrogen secretion during the first 2 weeks of treatment with the LHRH agonist and also to neutralize the action of estrogens derived from ovarian androstenedione as well as adrenal and ovarian DHEA (Labrie, Martel et al. 2011). In fact, adrenal and ovarian DHEA are converted to estrogens in endometriotic but not normal endometrial tissue. Accordingly, the estrogens of adrenal and ovarian origins made from DHEA can continue to stimulate endometriotic cells after cessation of ovarian estrogen secretion by the LHRH agonist or antagonist.

It is important to mention that while the normal endometrium cannot synthesize estrogens from DHEA because of the absence of aromatase, the endometriotic tissue possesses the enzyme able to transform DHEA into estrogens (Bulun, Lin et al. 2005). Such data indicate that blockade of ovarian estrogen secretion by an LHRH agonist or antagonist is only a partial treatment for endometriosis since estrogens are made locally in endometriotic tissue from DHEA, thus stimulating the proliferation of endometriotic cells while the normal endometrium is not stimulated by DHEA due to the absence of local formation of estrogens. The particularly high potency of a SERM having pure and potent estrogen antagonistic activity in the endometrial tissue will block any activity of any estrogen made from DHEA in the endometriotic tissue. Such complete estrogen blockade should lead to more complete and more rapid apoptosis and thus decrease the incidence of recurring endometriosis after cessation of therapy.

Figure 9:
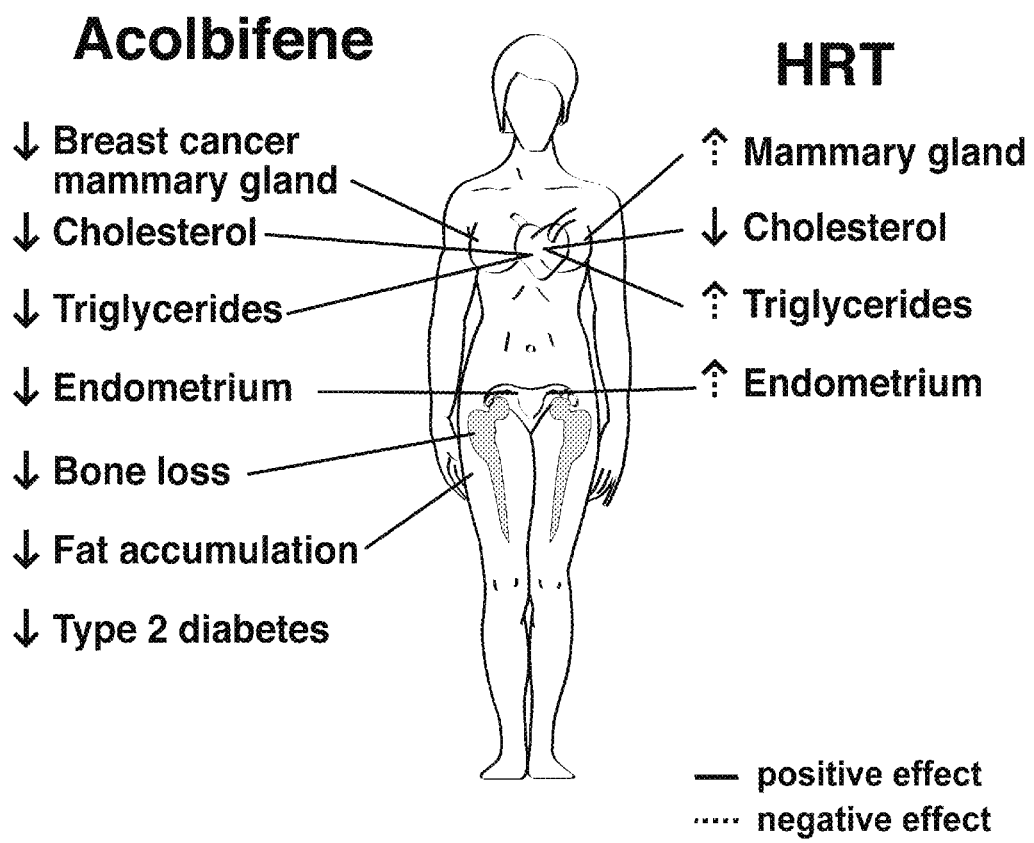
FIG. 9 shows comparison of the effects of standard HRT (estrogen) and a selective estrogen receptor modulator (SERM) on parameters of menopause.
Figure 10:
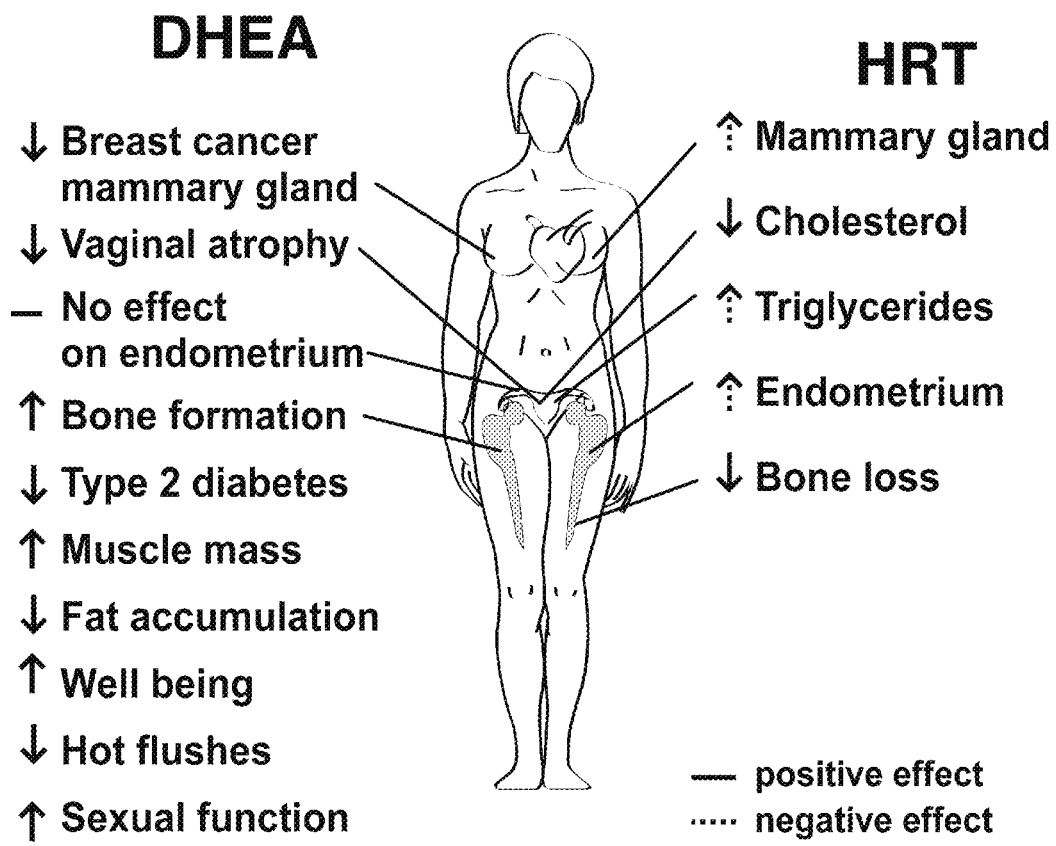
FIG. 10 shows comparison of the effects of standard HRT (estrogen) and dehydroepiandrosterone on parameters of menopause.
Figure 11:
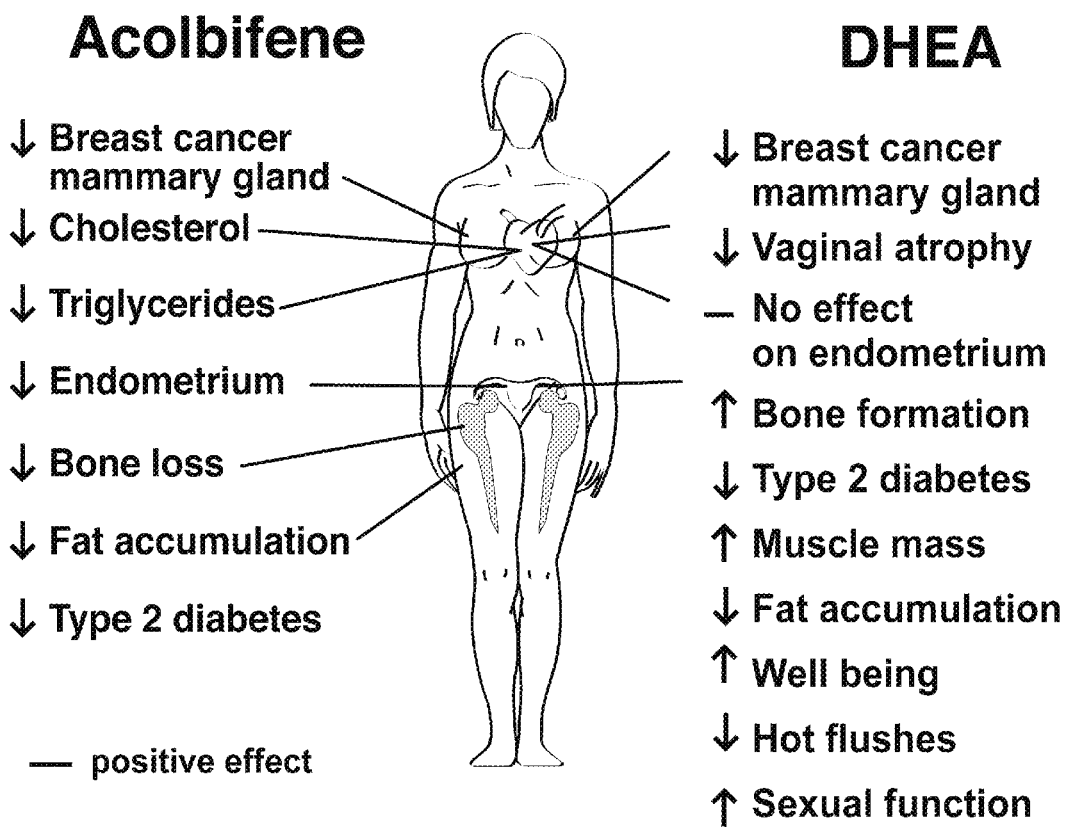
FIG. 11 shows the combined effects of SERM (acolbifene) and DHEA on parameters of menopause. No negative effect is expected.

On the other hand, while EM-652.HCl reduces bone loss and DHEA stimulates bone formation, thus more efficiently protecting bone function, the addition of DHEA should prevent hot flushes, a major limitation of LHRH agonist treatment alone. Comparison of the expected effects of the proposed combination versus add-back therapy in the HRT is illustrated in FIGS. 9, 10 and 11.

In order to facilitate the combination therapy aspect of the invention, for any indication discussed herein, the invention provides kits which include one or more SERM(s) and sex steroid precursors in separate or in one container and in another container an inhibitor of ovarian hormonal secretion. The kit may include appropriate materials for oral administration, e.g. tablets, capsules, syrups and the like and for transdermal administration, e.g., ointments, lotions, gels, creams, sustained release patches, and the like for intravaginal administration, e.g., suppositories, creams, ointments, tablets, gels and the like and for subcutaneous injection and intramuscular injection. Acolbifene and DHEA could be administered intravaginally.

Applicants believe that administration of SERM and inhibitor of ovarian hormonal secretion with or without administration of sex steroid precursor has utility in the treatment and/or prevention of the development of endometriosis and other estrogen-related diseases.

A selective estrogen receptor modulator of the invention has a molecular formula with the following features: a) two aromatic rings spaced by 1 to 2 intervening carbon atoms, both aromatic rings being either unsubstituted or substituted by a hydroxyl group or a group converted in vivo to hydroxyl or halogen or $C_1$-$C_6$ alkyl or $C_1$-$C_6$ alkylsulfone; and b) a side chain possessing an aromatic ring and a tertiary amine, carboxylic acid or alcohol function or salt thereof.

A preferred side chain of the selective estrogen receptor modulator of the invention is selected from the group consisting of:

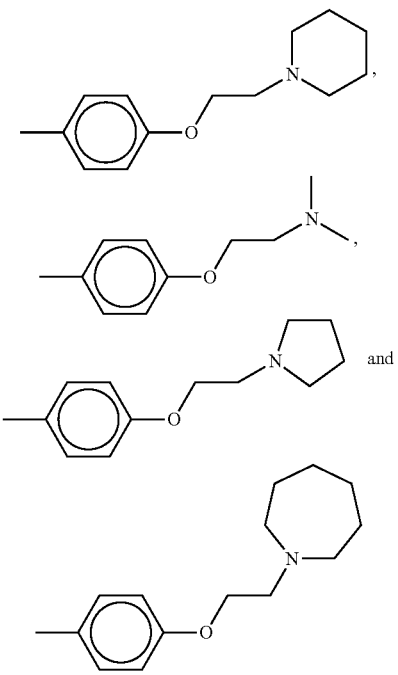

and

A preferred selective estrogen receptor modulator of the invention is selected from the group consisting of a benzothiophene derivative, triphenylethylene derivative, indole derivative, benzopyran derivative, chroman derivative, naphthalene derivative, dihydronaphthalene derivative, tetrahydronaphthalene derivative, benzothiopyran derivative, thiochroman derivative, quinoline derivative, dihydroquinoline derivative, and tetrahydroquinoline derivative.

A preferred selective estrogen receptor modulator of the invention has one of the following formulae selected from the group consisting of:

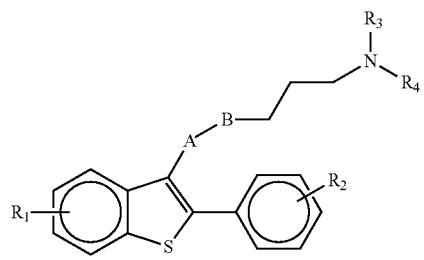

wherein $R_1$ and $R_2$ are independently selected from the group consisting of hydrogen, hydroxyl, a moiety converted in vivo in hydroxyl, halogen, $C_1$-$C_6$ alkyl and $C_1$-$C_6$ alkylsulfone;

wherein $R_3$ and $R_4$ are either independently selected from the group consisting of $C_1$-$C_4$ alkyl, or a moiety which in combination with the nitrogen atom to which they are bound, is selected from the group consisting of pyrrolidinyl, 2,2-dimethylpyrrolidinyl, 2-methylpyrrolidinyl, piperidino, hexamethyleneimino and morpholino;

wherein A is selected from the group consisting of —CO—, —CHOH—, —O—, and —CH$_2$—;

wherein B is selected from the group consisting of phenylene, pyridylidene, and -cycloC$_4$H$_2$N$_2$—;

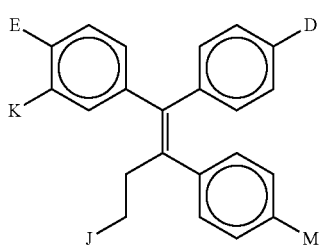

wherein D is —OCH$_2$CH$_2$N(R$_3$)R$_4$, —OCH$_2$CH$_2$OH, —OCH$_2$CH$_2$OCH$_2$CH$_2$OH or —CH═CH—COOH(R$_3$ and R$_4$ either being independently selected from the group consisting of C$_1$-C$_4$ alkyl, or a moiety which in combination with the nitrogen atom to which they are bound, is selected from the group consisting of pyrrolidinyl, 2,2-dimethylpyrrolidinyl, 2-methylpyrrolidinyl, piperidino, hexamethyleneimino and morpholino);
wherein E and K are independently hydrogen, hydroxyl, a moiety converted in vivo in hydroxyl or halogen;
wherein J is hydrogen or halogen;
wherein M is hydrogen or C$_1$-C$_6$ alkyl;

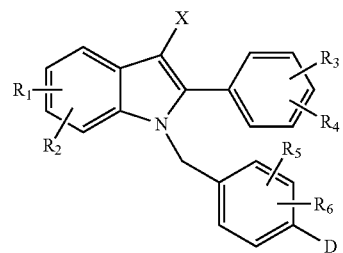

wherein D is selected from the groups consisting of —OCH$_2$CH$_2$N(R$_7$)R$_8$, —CH═CH—CO N(R$_7$)R$_8$, —CC—(CH$_2$)$_n$—N(R$_7$)R$_8$ (R$_7$ and R$_8$ either being independently selected from the group consisting of C$_1$-C$_4$ alkyl, or a moiety which in combination with the nitrogen atom to which they are bound, is selected from the group consisting of pyrrolidinyl, 2,2-dimethylpyrrolidinyl, 2-methylpyrrolidinyl, piperidino, hexamethyleneimino and morpholino);
wherein X is selected from the group consisting of hydrogen and C$_1$-C$_6$ alkyl;
wherein R$_1$, R$_2$, R$_3$, R$_4$, R$_5$, and R$_6$ are independently selected from the group consisting of hydrogen, hydroxyl, C$_1$-C$_6$ alkyl, halogen, and a moiety converted in vivo in hydroxyl;

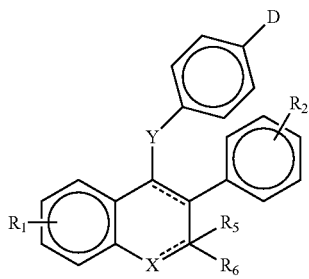

wherein R$_1$ and R$_2$ are independently selected from the group consisting of hydrogen, hydroxyl, halogen, C$_1$-C$_6$ alkyl and C$_1$-C$_6$ alkylsulfone, and a moiety converted in vivo in hydroxyl;

wherein R$_5$ and R$_6$ are independently hydrogen or C$_1$-C$_6$ alkyl;
wherein D is —OCH$_2$CH$_2$N(R$_3$)R$_4$ (R$_3$ and R$_4$ either being independently selected from the group consisting of C$_1$-C$_4$ alkyl, or a moiety which in combination with the nitrogen atom to which they are bound, is selected from the group consisting of pyrrolidinyl, 2,2-dimethylpyrrolidinyl, 2-methylpyrrolidinyl, piperidino, hexamethyleneimino and morpholino);
wherein X is selected from the group consisting of —O—, —CH$_2$—, —S—, —CH═, —N═, and —NR$_7$— (R$_7$ being hydrogen or C$_1$-C$_6$ alkyl);
wherein Y is selected from the group consisting of —O— and —CH$_2$— or direct bond;

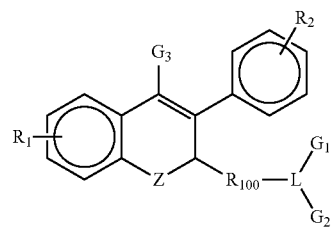

wherein R$_1$ and R$_2$ are independently hydrogen, hydroxyl, halogen, C$_1$-C$_6$ alkyl, and a moiety which is converted to hydroxyl in vivo;
wherein Z is selected from the group consisting of —O—, —CH$_2$—, —S—, and —NR$_7$— (R$_7$ being hydrogen or C$_1$-C$_6$ alkyl);
wherein the R$_{100}$ is a bivalent moiety which distances L from the B-ring by 4-10 intervening atoms;
wherein L is a bivalent or trivalent polar moiety selected from the group of —SO—, —CON<, —N<, and —SON<;
wherein G$_1$ is selected from the group consisting of hydrogen, a C$_1$ to C$_5$ hydrocarbon, a bivalent moiety which in combination with G$_2$ and L is a 5- to 7-membered heterocyclic ring, and halo or unsaturated derivatives of the foregoing;
wherein G$_2$ is either absent or selected from the group consisting of hydrogen, a C$_1$ to C$_5$ hydrocarbon, a bivalent moiety which in combination with G$_1$ and L is a 5- to 7-membered heterocyclic ring, and halo or unsaturated derivatives of the foregoing;
wherein G$_3$ is selected from the group consisting of hydrogen, methyl, ethyl and trifluoromethyl;

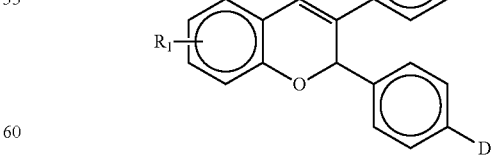

or a pharmaceutically acceptable salt thereof;
wherein D is —OCH$_2$CH$_2$N(R$_3$)R$_4$ (R$_3$ and R$_4$ either being independently selected from the group consisting of C$_1$-C$_4$ alkyl, or a moiety which in combination with the nitrogen atom to which they are bound, is selected from the group consisting of pyrrolidinyl, 2,2-dimethylpyrrolidinyl, 2-methylpyrrolidinyl, piperidino, hexamethyleneimino and morpholino);
wherein $R_1$ and $R_2$ are independently selected from the group consisting of hydrogen, hydroxyl, halogen, $C_1$-$C_6$ alkyl, and a moiety converted in vivo in hydroxyl;
wherein $G_3$ is selected from the group consisting of hydrogen, methyl, ethyl and trifluoromethyl;

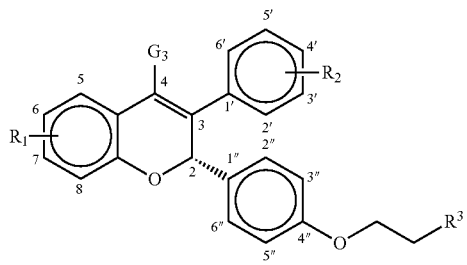

or pharmaceutically acceptable salt thereof;
wherein a benzopyran derivative is optically active due to a majority of its stereoisomer having an absolute configuration S on carbon 2 and substantially lacks (2R)-enantiomer;
wherein $R_1$ and $R_2$ are independently selected from the group consisting of hydroxyl, halogen, $C_1$-$C_6$ alkyl, and a moiety convertible in vivo to hydroxyl;
wherein $R^3$ is a species selected from the group consisting of saturated, unsaturated or substituted pyrrolidinyl, saturated, unsaturated or substituted piperidino, saturated, unsaturated or substituted piperidinyl, saturated, unsaturated or substituted morpholino, nitrogen-containing cyclic moiety, nitrogen-containing polycyclic moiety, and NRaRb (Ra and Rb being independently hydrogen, straight or branched $C_1$-$C_6$ alkyl, straight or branched $C_2$-$C_6$ alkenyl, and straight or branched $C_2$-$C_6$ alkynyl);
wherein $G_3$ is selected from the group consisting of methyl and trifluoromethyl;
wherein an optional salt of an acid selected from the group consisting of acetic acid, adipic acid, benzenesulfonic acid, benzoic acid, camphorsulfonic acid, citric acid, fumaric acid, hydroiodic acid, hydrobromic acid, hydrochloric acid, hydrochlorothiazide acid, hydroxy-naphthoic acid, lactic acid, maleic acid, methanesulfonic acid, methylsulfuric acid, 1,5-naphthalenedisulfonic acid, nitric acid, palmitic acid, pivalic acid, phosphoric acid, propionic acid, succinic acid, sulfuric acid, tartaric acid, terephthalic acid, p-toluenesulfonic acid, and valeric acid.

One preferred SERM of the invention is EM-800 reported in PCT/CA96/00097 (WO 96/26201). The molecular structure of EM-800 is:

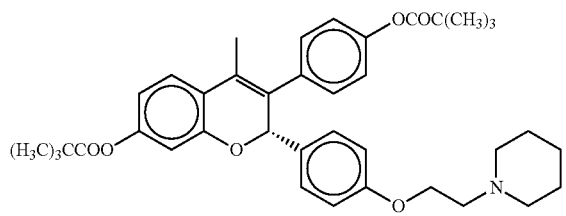

Another preferred SERM of the invention is EM-652.HCl reported in U.S. Pat. No. 6,710,059 B1:

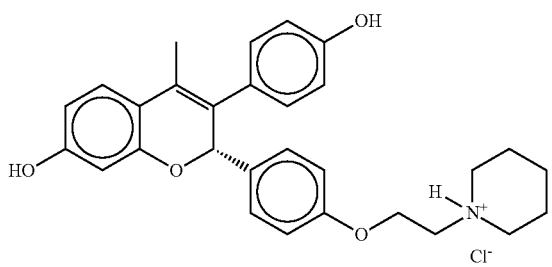

EM-652.HCl, (also called EM-1538 or acolbifene) is the hydrochloride salt of the potent antiestrogen EM-652. Compared to EM-800, EM-652.HCl is a simpler and easier salt to synthesize. It is also easy to isolate, purify, crystallize and displays good solid state stability. In administering either EM-800 or EM-652.HCl, it results in the same active compound having the same activity in vivo. Since both precursors lead to similar blood levels of the active compound EM-652.

Another preferred SERM is Bazedoxifene (TSE-424; WAY-TSE 424; WAY 140424; 1-[[4-[2-(hexahydro-1H-azepin-1-yl)ethoxy]phenyl]methyl]-2-(4-hydroxyphenyl)-3-methyl-1H-indol-5-ol, acetate) developed by Wyeth Ayers (USA) and disclosed in JP10036347 (American home products corporation) and approved in USA for the prevention of postmenopausal osteoporosis and non-steroidal estrogen derivatives described in WO 97/32837. Other preferred SERMs of the invention include Tamoxifen ((Z)-2-[4-(1,2-diphenyl-1-butenyl)phenoxy]-N,N-dimethylethanamine) (available from Zeneca, UK), Toremifene ((Z)-2-[4-(4-Chloro-1,2-diphenyl-1-butenyl)phenoxy]-N,N-dimethylethanamine) available from Orion, Finland, under the trademark Fareston or Schering-Plough), Droloxifene ((E)-3-[1-[4-[2-(Dimethylamino) ethoxy]phenyl]-2-phenyl-1-butenyl] phenol) and, from Eli Lilly and Co., USA: Raloxifene ([2-(4-hydroxyphenyl)-6-hydroxybenzo[b]thien-3-yl][4-[2-(1-piperidinyl)ethoxy]phenyl]-methanone hydrochloride), LY 335124, LY 326315, LY 335563 (Desmethylarzoxifene) (6-hydroxy-3-[4-[2-(1-piperidinyl)ethoxy]phenoxyl]-2-(4-hydroxyphenyl)benzo[b]thiopene hydrochloride) and Arzoxifene (LY 353381, 6-hydroxy-3-[4-[2-(1-piperidinyl) ethoxy]phenoxyl]-2-(4-methoxyphenyl)benzo[b]thiophene hydrochloride). Other preferred SERMs are Lasofoxifene (CP-336,156) (cis-1R-[4'-pyrrolidinoethoxyphenyl]-2S-phenyl-6-hydroxy-1,2,3,4-tetrahydronaphthalene D-(−)-tartrate salt) (Pfizer Inc., USA described in U.S. Pat. No. 5,889,042), Idoxifene ((E)-1-[2-[4-[1-(4-Iodophenyl)-2-phenyl-1-butenyl]phenoxy]ethyl]pyrrolidine) (SmithKline Beecham, USA), Levormeloxifene (3,4-trans-2,2-dimethyl-3-phenyl-4-[4-(2-(2-(pyrrolidin-1-yl)ethoxy)phenyl]-7-methoxychroman) (Novo Nordisk, A/S, Denmark) which is disclosed in Shalmi et al. WO 97/25034, WO 97/25035, WO 97/25037, WO 97/25038; and Korsgaard et al. WO 97/25036), GW 5638 (described by Willson et al., 1997) and indole derivatives (disclosed by Miller et al., EP 0802183A1) Are also included, Iproxifen (TAT 59; (E)-4-[1-[4-[2-(dimethylamino)ethoxy]phenyl]-2-[4-(1-methylethyl)phenyl]-1-butenyl]phenol dihydrogen phosphate) from Taiho (Japan), Ospemifene (FC 1271; ((Z)-2-[4-(4-chloro-1,2-diphenyl-1-butenyl)phenoxyl]ethanol) from available from Orion-Farmos Pharmaceutica, Finland, SERM 3471, HMR 3339 and HMR 3656 from Sanofi-Aventis (France), Pipendoxifene (ERA-923) developed by Wyeth-Ayers, nonsteroidal estrogen derivatives described in WO 97/32837, Fispemifene developed by QuatRx (USA) and CC 8490 developed by Celgene in USA.

Any SERM used as required for efficacy, as recommended by the manufacturer, can be used. Appropriate dosages are known in the art. Any other non steroidal antiestrogen commercially available can be used according to the invention. Any compound having activity similar to SERMs (example: Raloxifene can be used).

SERMs administered in accordance with the invention are preferably administered in a dosage range between 0.01 to 10 mg/kg of body weight per day (preferably 0.05 to 1.0 mg/kg), with 60 mg per day, especially 20 mg per day, in one or two equally divided doses being preferred for a person of average body weight when orally administered, or in a dosage range between 0.003 to 3.0 mg/kg of body weight per day (preferably 0.015 to 0.3 mg/kg of body weight), with 20 mg per day, especially 10 mg per day, in two equally divided doses being preferred for a person of average body weight when parenterally administered (i.e. intramuscular, subcutaneous or percutaneous or intravaginal administration). Preferably the SERMs are administered together with a pharmaceutically acceptable diluent or carrier as described below.

With respect to all of the dosages recommended herein, the attending clinician should monitor individual patient response and adjust dosage accordingly.

Preferred sex steroid precursors are dehydroepiandrosterone (DHEA) (available from Proquina, Mexico), its prodrugs (available from Steraloids, Wilton, N.H., USA), 5-androsten-3β,17β-diol and its prodrugs androst-5-ene-3β,17β-diol 3-acetate and androst-5-ene-3β,17β-diol dihemisuccinate (available from Steraloids, Wilton, N.H. USA).

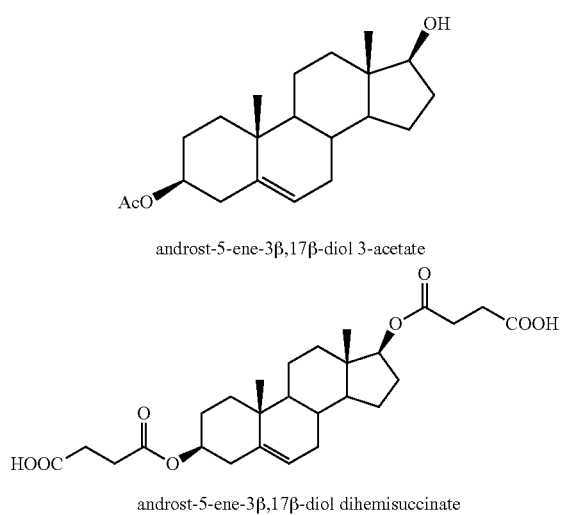

androst-5-ene-3β,17β-diol 3-acetate androst-5-ene-3β,17β-diol dihemisuccinate

The active ingredients of the invention (whether SERM or precursor or inhibitor of ovarian hormonal secretion otherwise) may be formulated and administered in a variety of manner.

Sex steroid precursors administered in accordance with the invention are preferably administered in a dosage range (1) between 0.5 to 100 mg per day, (preferably 3 to 50 mg per day), when intravaginally administered; (2) in a dosage range between 15 to 200 mg per day (preferably 30 mg to 100 mg per day), when administered on the skin; (3) in a dosage range between 10 to 200 mg per day (preferably 25 mg to 100 mg per day), e.g., 75 mg per day, when orally administered; or (4) in a dosage range between 1.0 to 25 mg per day (preferably 3.25 to 20 mg per day), when parentally administered (i.e. intramuscular, or subcutaneous).

Active ingredient for transdermal or transmucosal is preferably present at from 0.5% to 20% by weight relative to the total weight of the pharmaceutical composition more preferably between 0.1 to 10%. Alternatively, the active ingredient may be placed into a transdermal patch having structures known in the art, for example, structures such as those set forth in E.P. Patent No. 0279982.

When formulated as an ointment, lotion, gel or cream or the like, the active compound is admixed with a suitable carrier which is compatible with human skin or mucosa and which enhances transdermal penetration of the compound through the skin or mucosa. Suitable carriers are known in the art and include but are not limited to Klucel HF and Glaxal base. Some are commercially available, e.g., Glaxal base available from Glaxal Canada Limited Company. Other suitable vehicles can be found in Koller and Buri, S.T.P. Pharma 3(2), 115-124, 1987. The carrier is preferably one in which the active ingredient(s) is (are) soluble at ambient temperature at the concentration of active ingredient that is used. The carrier should have sufficient viscosity to maintain the inhibitor on a localized area of skin or mucosa to which the composition has been applied, without running or evaporating for a time period sufficient to permit substantial penetration of the precursor through the localized area of skin or mucosa and into the bloodstream where it will cause a desirable clinical effect. The carrier is typically a mixture of several components, e.g. pharmaceutically acceptable solvents and a thickening agent. A mixture of organic and inorganic solvents can aid hydrophylic and lipophylic solubility, e.g. water and an alcohol such as ethanol.

In another aspect, the invention provides a pharmaceutical composition comprising a sex steroid precursor selected from the group consisting of dehydroepiandrosterone, dehydroepiandrosterone-sulfate, androst-5-ene-3β, 17β-diol, and 4-androstene-3,17-dione and further comprising a pharmaceutically acceptable excipient, diluent or carrier selected from the group consisting of triglycerides of saturated fatty acids C12-C18 with varied portions of the corresponding partial glycerides (hard fat, Witepsol), butter, mixed triglycerides of oleic, palmitic, and stearic acids (cocoa butter), partially hydrogenated cottonseed oil (Cotomar), hydrogenated fatty alcohols and esters (Dehydag Base I, Base II or Base III, may also contains glycerides of saturated fatty acids C12-C16), triglycerides from palm, palm kernel, and coconut oils with self-emulsifying glyceryl monostearate and polyoxyl stearate (Fattibase), Hexaride Base 95, higher melting fractions of coconut and palm kernel oil (Hydrokote), Rearranged hydrogenated vegetable oils (S-70-XX95 and S-070-XXA), eutectic mixtures of mono-, di-, triglycerides derived from natural vegetable oils (Suppocire), Tegester Triglycerides, Tween 61, triglycerides derived from coconut oil (Wecobee), theobroma oil, semisynthetic glycerides (Japocire, Ovucire), mixture of tri- di- and monoglycerides of saturated fatty acids (Massa Estarinum) and a combination of the foregoing (see Allen et al. 2008). Any vehicle including liquid in which DHEA and other precursors are soluble covers by this invention.

It is preferred that the sex steroid precursor is formulated as an alcoholic gel containing 2.0 to 10% of caprylic-capric triglyceride (Neobee M-5); 10 to 20% of hexylene glycol; 2.0 to 10% of diethyleneglycol monomethyl ether (Transutol); 2.0 to 10% of Cyclomethicone (Dow Corning 345); 1.0 to 2% of benzyl alcohol and 1.0 to 5.0% of hydroxypropylcellulose (Klucel HF).

The carrier may also include various additives commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present. When used to treat systemic diseases, the site of application on the skin should be changed in order to avoid excess local concentration of active ingredient and possible overstimulation of the skin and sebaceous glands by androgenic metabolites of sex steroid precursor.

In a pharmaceutical composition for oral administration, DHEA or other precursor is preferably present in a concentration between 5 and 98% by weight relative to total weight of the composition more preferably between 50 and 98 percent, especially between 80 and 98 percent. A single precursor such as DHEA may be the only active ingredient, or alternatively, a plurality of precursors and/or their analogues may be used (e.g., a combination of DHEA, DHEA-S, 5-diol, or a combination of two or more compounds converted in vivo to DHEA, DHEA-S or 5-diol or a combination of DHEA or 5-diol and one or more analogues thereof which are converted to DHEA or 5-diol in vivo, etc. The blood level of DHEA is the final criteria of adequate dosage which takes into account individual variation in absorption and metabolism.

Preferably, the attending clinician will, especially at the beginning of treatment, monitor an individual patient's overall response and serum levels of DHEA (in comparison to the preferred serum concentrations discussed above), and monitor the patient's overall response to treatment, adjusting dosages as necessary where a given patients' metabolism or reaction to treatment is atypical.

Treatment in accordance with the invention is suitable for indefinite continuation. It is expected that DHEA and/or 5-diol treatment will simply maintain DHEA levels within a range similar to that which occurs naturally in women before menopause (serum concentration between 4 and 10 micrograms per liter).

The SERM compound or the sex steroid precursor can also be administered, by the oral route, and may be formulated with conventional pharmaceutical excipients, e.g. spray dried lactose, microcrystalline cellulose, and magnesium stearate into tablets or capsules for oral administration.

The active substance (SERM compound or the sex steroid precursor) can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol. Of course, taste-improving substances can be added in the case of oral administration forms.

As further forms, one can use plug capsules, e.g. of hard gelatin, as well as closed soft-gelatin capsules comprising a softner or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

The lotion, ointment, gel or cream should be thoroughly rubbed into the skin so that no excess is plainly visible, and the skin should not be washed in that region until most of the transdermal penetration has occurred preferably at least 4 hours and, more preferably, at least 6 hours.

A transdermal patch may be used to deliver precursor or LHRH agonist or antagonist in accordance with known techniques. It is typically applied for a much longer period, e.g., 1 to 4 days, but typically contacts active ingredient to a smaller surface area, allowing a slow and constant delivery of active ingredient.

A number of transdermal drug delivery systems that have been developed, and are in use, are suitable for delivering active ingredients (SERM, sex steroid precursor, and LHRH agonist or antagonist) of the present invention. The rate of release is typically controlled by a matrix diffusion, or by passage of the active ingredient through a controlling membrane.

Mechanical aspects of transdermal devices are well known in the rat, and are explained, for example, in U.S. Pat. Nos. 5,162,037, 5,154,922, 5,135,480, 4,666,441, 4,624,665, 3,742,951, 3,797,444, 4,568,343, 5,064,654, 5,071,644, 5,071,657 the disclosures of which are incorporated herein by reference. Additional background is provided by European Patent 0279982 and British Patent Application 2185187.

The device may be any of the general types known in the art including adhesive matrix and reservoir-type transdermal delivery devices. The device may include drug-containing matrixes incorporating fibers which absorb the active ingredient and/or carrier. In a reservoir-type device, the reservoir may be defined by a polymer membrane impermeable to the carrier and to the active ingredient.

In a transdermal device, the device itself maintains active ingredient in contact with the desired localized skin surface. In such a device, the viscosity of the carrier for active ingredient is of less concern than with a cream or gel. A solvent system for a transdermal device may include, for example, oleic acid, linear alcohol lactate and dipropylene glycol, or other solvent systems known in the art. The active ingredient may be dissolved or suspended in the carrier.

For attachment to the skin, a transdermal patch may be mounted on a surgical adhesive tape having a hole punched in the middle. The adhesive is preferably covered by a release liner to protect it prior to use. Typical material suitable for release includes polyethylene and polyethylene-coated paper, and preferably silicone-coated for ease of removal. For applying the device, the release liner is simply peeled away and the adhesive attached to the patient's skin. In U.S. Pat. No. 5,135,480, the disclosure of which is incorporated by reference, Bannon et al. describe an alternative device having a non-adhesive means for securing the device to the skin.

The percutaneous or transmucosal delivery system of the invention may also be used as a novel and improved delivery system for the prevention and/or treatment of endometriosis or other diseases which respond favorably to treatment with androgens and/or estrogens.

The LHRH agonist or antagonist is administered parenterally, i.e., intramuscularly, subcutaneously or intravenously by injection or infusion by nasal drops or by suppository. The LHRH agonist or antagonist may also be microencapsulated in or attached to a biocompatible, biodegradable polymer, e.g., poly(d,1-lactide-co-glycolide) and subcutaneously or intramuscularly injected by a technique called subcutaneously or intramuscular depot to provide continuous, slow release of the LHRH agonist or antagonist over a period of 30 days or longer. The most preferred route of administration of the LHRH agonist or antagonist is subcutaneous or intramuscular de pot injection.

The LHRH agonist or antagonist may be administered at from about 10 to 1500 μg per day and about 250 (preferably 50 μg to 500 μg per day) for the LHRH agonist and to about 100 to 2000 μg per day for the LHRH antagonist being preferred.

The LHRH agonist or antagonist may be administered subcutaneously in a daily dose of 500 μg for the first 30 days and thereafter subcutaneously in a daily dose of 250 μg regardless of the patients' body weight. When the LHRH agonist or antagonist is administered, once every 30-day period is used, with a dose of 750 to 15,000 μg per 30-day period being preferred. Similar daily delivery doses are used for longer-term controlled release formulations.

Preferred LHRH agonists are leuprolide acetate available under the trademark "Lupron" from Abbott Laboratories Ltd., "Viadur" from Bayer AG, "Eligard" from Sanofi-Aventis, and "Prostap SR" and "Prostap 3" from Takeda UK, Goserelin acetate available under the trademark "Zoladex" and "Zoladex LA" from AstraZeneca, Nafarelin available under the trademark "Synarel" from Searle (now part of Pfizer), Buserelin acetate available under the trademark "Suprefact" or "Suprefact Depot" from Sanofi-Aventis and "CinnaFact" from CinnaGen, Histrelin acetate available under the trademark "Vantas" and "Supprelin LA" from Endo Pharmaceuticals, Triptorelin acetate or pamoate available under the trademark "Decapeptyl" from Ipsen, "Diphereline" and "Gonapeptyl" from Ferring Pharmaceuticals, and "Trelstar" from Watson. Any LHRH agonist or antagonist can be used.

A typical pharmaceutical composition of the LHRH agonist or antagonist includes the LHRH agonist or antagonist or a pharmaceutically acceptable acid salt thereof, benzyl alcohol, a phosphate buffer (pH 6.0-6.5) and sterile water.

The LHRH agonist or antagonist for intramuscular or subcutaneous depot injection may be microencapsulated in a biocompatible, biodegradable polymer, e.g., poly (d,1-lactide-co-glycolide) by a phase separation process or formed into a pellet. The microspheres may then be suspended in a carrier to provide an injectable preparation or the depot may be injected in the form of a pellet. Se also European patent application EPA No. 58,481 published Aug. 25, 1982 for solid compositions for subdermal injection or implantation of liquid formulations for intramuscular or subcutaneous injections containing biocompatible, biodegradable polymers such as lactide-glycolide copolymer and LHRH agonist, e.g. D-Ser-t-BuO$^6$, Azgly$^{10}$-LHRH. These formulations permit controlled release of the peptide.

By the term "LHRH agonist" is meant synthetic analogues of the natural luteinizing hormone-releasing hormone (LHRH), for example, a decapeptide of the structure: L-pyroglutamyl-L-histidyl-L-tryptophyl-L-seryl-L-tyrosyl-glycyl-L-leucyl-L-arginyl-L-prolylglycyl-NH$_2$. Suitable LHRH agonists include nonapeptides and decapeptides represented by the formula: L-pyroglutamyl-L-histidyl-L-tryptophyl-L-seryl-L-tyrosyl-X-Y-arginyl-L-prolyl-Z wherein X is D-tryptophyl, D-leucyl, D-alanyl, iminobenzyl-D-histidyl, 3-(2-naphthyl)-D-alanyl, O-tert-butyl-D-seryl, D-tyrosyl, D-lysyl, D-phenylalanyl, 1-benzyl-D-histidyl or N-methyl-D-alanyl and Y is L-leucyl, D-leucyl, N$^α$-methyl D-leucyl, N$^α$-methyl-L-leucyl or D-alanyl and wherein Z is (Aza)glycyl-NHR$_1$ or NHR$_1$ wherein R$_1$ is H, lower alkyl or lower haloalkyl. Lower alkyl includes straight—or branched-chain alkyls having 1 to 6 carbon atoms, e.g., methyl, ethyl, propyl, pentyl or hexyl, isobutyl, neopentyl and the like. Lower haloalkyl includes straight—and branched-chain alkyls of 1 to 6 carbon atoms having a halogen substituent, e.g., —CF$_3$, —CH$_2$CF$_3$, —CF$_2$CH$_3$. Halogen means F, Cl, Br, I with Cl being preferred.

In preferred nonapeptides, Y is L-leucyl, X is an optically active D-form of tryptophan, serine (t-BuO), leucine, histidine (iminobenzyl), and alanine.

Preferred decapeptides include [D-Trp$^6$]-LHRH wherein X=D-Trp, Y=L-leucyl, Z=glycyl-NH$_2$, [D-Phe$^6$]LHRH wherein X=D-phenylalanyl, Y=L-leucyl and Z-glycyl-NH$_2$) or [D-Nal(2)$^6$]LH-RH which is [(3-(2-naphthyl)-D-Ala$^6$] LHRH wherein X=3-(2-naphthyl)-D-alanyl, Y=L-leucyl and Z=glycyl-NH$_2$).

Other LHRH agonists useful within the scope of this invention are the α-aza analogues of the natural LH-RH, especially, [D-Phe$^6$, Azgly$^{10}$]-LHRH, [D-Tyr(Me)$^6$, Azgly$^{10}$]-LHRH, and [D-Ser-(t-BuO)$^6$, Azgly$^{10}$]-LHRH, disclosed by (Dutta, Furr et al. 1978) and U.S. Pat. No. 4,100,274 as well as those disclosed in U.S. Pat. Nos. 4,024,248 and 4,118,483.

Preferred LHRH antagonists are Abarelix available under the trademark "Plenaxis" from Specialty European Pharma, Teverelix developed by Ardana, Cetrorelix acetate available under the trademark "Cetrotide" from Merck Serono, Ganirelix acetate available under the trademark "Antagon" from Organon International, Iturelix under the trademark "Antide" from Serono, Acyline developed by Merrion Pharmaceuticals, Degarelix under the trademark "Firmagon" from Ferring Pharmaceuticals, and Ornirelix developed by Oakwood Laboratories.

Other LHRH antagonists are Azaline B (Salk Institute), Ozarelix (Spectrum Pharmaceuticals), LXT-101 (Department of Pharmaceutical Chemistry, Beijing Institute of Pharmacology and Toxicology), Elagolix (Neurocrine Biosciences), and TAK-013 and TAK-385 (Takeda).

Typical suitable LHRH antagonists include [N—Ac-D-p-Cl-Phe$^{1,3}$, D-Phe$^3$, D-Arg$^6$, D-Ala$^{10}$]LHRH disclosed by (Erchegyi, Coy et al. 1981) [N—Ac-D-p-Cl-Phe$^{1,2}$, D-Trp$^3$, D-Arg$^6$, D-Ala$^{10}$]LHRH disclosed by (Coy, Horvath et al. 1982); [N—Ac-D-(3-(2-naphthyl)-Ala)$^1$, D-p-Cl-Phe$^2$, D-Trp$^3$, D-hArg(Et$_2$)$^6$, D-Ala$^{10}$]-LHRH and [N—Ac-Pro$^1$, D-p-Cl-Phe$^2$, (D-(3-(2-naphthyl(Ala$^{3,6}$]-LHRH disclosed by (Nestor, Ho et al. 1984); the nona- and decapeptides analogs of LHRH useful as LHRH antagonists disclosed in U.S. Pat. No. 4,481,190 analogs of highly constrained cyclic antagonist, cycle [Δ$^3$Pro$^1$, D-p-Cl-Phe$^2$, D-Trp$^{3,5}$, N-Me-Leu$^7$, β-Ala$^{10}$] LHRH disclosed by (Rivier, Rivier et al. 1984), and [N—Ac-D-(3-(2-naphthyl)-Ala)$^1$, D-p-F-Phe$^2$, D-Trp$^3$, D-Arg$^6$]-LHRH disclosed by (Corbin, Bex et al. 1984).

Other LHRH agonist and antagonist analogs are disclosed in LHRH and its Analogues (B. H. Vickery et al., editors at page 3-10 (J. J. Nestor), 11-22 (J. River et al.) and 23-33 (J. J. Nestor et al.) and Gynecological Endocrinology 13 (Suppl. 1) 1999: see GnRH antagonist (T-98475), p. 8, abst. #015. Other LHRH agonist is Deslorelin acetate available under the trademark "Ovuplant" from Peptech.

Example of Efficiency

A—Materials and Methods

A.1—Animals and Treatment

Ten to twelve week-old female Sprague-Dawley rats (Crl:CD(SD)Br) weighing approximately 235-250 g at start of treatment were used. One hundred twenty rats were randomly distributed between 5 groups of 15 intact animals per group as follows: 1) Control; 2) LHRH-A (0.002 mg/animal); 3) LHRH-A+EM-652.HCl (2.5 mg/kg); 4) LHRH-A+ DHEA (100 mg/kg); 5) LHRH-A+EM-652.HCl+DHEA. EM-652.HCl ((S)-(+)-7-hydroxy-3-(4'-hydroxyphenyl)-4- methyl-2-(4"-(2'''-piperidinoethoxy)phenyl)-2H-1 benzopyran hydrochloride) was administered once daily by oral gavage as suspension in 0.4% methylcellulose (0.5 ml/rat) for 3 months, DHEA was applied topically once daily on dorsal skin as a solution in 50% ethanol-50% propylene glycol (0.5 ml/rat) for the same time period while LHRH-A was injected subcutaneously once daily in phosphate buffer (0.5 ml/rat). Approximately after 3 months of treatment, a blood sample was collected at the jugular vein of overnight fasted animals for measurement of total serum cholesterol levels using the Boehringer Mannheim Diagnostic Hitachi 911 Analyzer.

Bone Mineral Density Measurement

After 12 weeks of treatment, individual rats under anesthesia with isoflurane had their whole body skeleton as well as their right femur scanned using dual energy x-ray absorptiometry (DEXA; QDR 4500A, Hologic, Waltham, Mass.) and a Regional High Resolution Scan software. The bone mineral content (BMC), and the bone mineral density (BMD) of whole body skeleton, lumbar spine and femur were determined. The body composition was determined at the same time.

Bone Alkaline Phosphatase

The total activity of serum alkaline phosphatase was determined using the Boehringer Mannheim Diagnostic Hitachi 911 Analyzer (Boehringer Mannheim Diagnostic Laboratory Systems). Then, the serum samples (0.1 ml) were mixed with 0.1 ml of a wheat germ lectin solution (6 mg/ml in water), incubated 30 min at room temperature and centrifuged for 3 min at 10000 g for precipitation of bone ALP. The ALP activity in the resulting supernatant was determined using the Boehringer Mannheim Diagnostic Hitachi 911 Analyzer and the bone ALP activity was calculated as follows: Bone ALP=Total ALP−(2×ALP of supernatant).

Statistical Analyses

Data are expressed as the means±SEM. Statistical significance was determined according to the multiple-range test of Duncan-Kramer.

KIT EXAMPLES

Set forth below, by way of example and not of limitation, are several kits utilizing preferred active SERM Acolbifene (EM-652.HCl, EM-1538), preferred active sex steroid precursor dehydroepiandrosterone (DHEA, Prasterone) and preferred LHRH-agonist Leuprolide acetate (Lupron depot). Other compounds of the invention or combination thereof, may be used in place of (or in addition to) Acolbifene, dehydroepiandrosterone, and Leuprolide acetate. LHRH-antagonist could be used instead of LHRH-agonist. The concentration of active ingredient may be varied over a wide range as discussed herein. The amounts and types of other ingredients that may be included are well known in the art.

Example A

The SERM and the sex steroid precursor are orally together administered in the same formulation (capsules) while LHRH agonist is parenterally administered.

| Ingredient | Weight % (by weight of total composition) |
|---|---|
| SERM and sex steroid precursor composition for oral administration (capsules) | |
| Acolbifene | 5.0 |
| DHEA | 10.0 |
| Lactose hydrous | 70.0 |
| Starch | 4.8 |
| Cellulose microcrystalline | 9.8 |
| Magnesium stearate | 0.4 |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example B

The SERM and the sex steroid precursor are orally together administered in the same formulation (tablets) while LHRH agonist is parenterally administered.

| Ingredient | Weight % (by weight of total composition) |
|---|---|
| SERM and sex steroid precursor composition for oral administration (tablets) | |
| IAcolbifene | 5.0 |
| DHEA | 15.0 |
| Gelatin | 5.0 |
| Lactose | 58.5 |
| Starch | 16.5 |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example C

The SERM and the sex steroid precursor are percutaneously together administered in the same formulation (cream) while LHRH agonist is parenterally administered.

| Ingredient | Weight % (by weight of total composition) |
|---|---|
| SERM and sex steroid precursor composition for percutaneous administration (cream) | |
| DHEA | 1.0 |
| Acolbifene | 0.2 |
| Emulsifying Wax, NF | 18.0 |
| Light mineral oil, NF | 12.0 |
| Benzyl alcohol | 1.0 |
| Ethanol 95% USP | 33.8 |
| Purifed water, USP | 34.0 |

| Ingredient | Weight % (by weight of total composition) |
|---|---|
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example D

The SERM and the sex steroid precursor are intravaginally together administered in the same formulation (suppository or ovule) while LHRH agonist is parenterally administered.

| Ingredient | Weight % (by weight of total composition) |
|---|---|
| SERM and sex steroid precursor composition for intravaginal administration (suppository or ovule) | |
| DHEA | 0.25 to 2.0 |
| Acolbifene | 0.25 to 3.0 |
| Witepsol H-15 base | 95.0 to 99.5 |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example E

The SERM and the sex steroid precursor are orally administered (capsules) while LHRH agonist is parenterally administered.

| Ingredient | Weight % (by weight of total composition) |
|---|---|
| SERM composition for oral administration (capsules) | |
| Acolbifene | 5.0 |
| Lactose hydrous | 80.0 |
| Starch | 4.8 |
| Cellulose microcrystalline | 9.8 |
| Magnesium stearate | 0.4 |
| + | |
| DHEA composition for oral administration (Gelatin capsule) | |
| DHEA | 25.0 |
| Lactose hydrous | 27.2 |
| Sodium Starch Glycolate | 20.0 |
| Microcrystalline Cellulose, Colloidal Silicon Dioxide, Silica Colloidal Anhydrous and Light Anhydrous Silicic Acid | 27.2 |

| Ingredient | Weight % (by weight of total composition) |
|---|---|
| Colloidal Silicon Dioxide | 0.1 |
| Magnesium stearate | 0.5 |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Other SERMs may be substituted for Acolbifene in the above formulations, as well as other sex steroid precursors may be substituted for DHEA, and as well as other LHRH agonists or antagonists may be substituted for Leuprolide acetate. More than one SERM or more than one sex steroid precursor or more than one LHRH agonist may be included in which case the combined weight percentage is preferably that of the weight percentage for the single sex steroid precursor or single SERM or single LHRH agonist given in the examples above.

Example F

The SERM is orally administered and the sex steroid precursor is intravaginally administered while LHRH agonist is parenterally administered.

| Ingredient | Weight % (by weight of total composition) |
|---|---|
| SERM composition for oral administration (capsules) | |
| Acolbifene | 5.0 |
| Lactose hydrous | 80.0 |
| Starch | 4.8 |
| Cellulose microcrystalline | 9.8 |
| Magnesium stearate | 0.4 |
| + | |
| Sex steroid precursor composition for intravaginal administration (suppository or ovule) | |
| DHEA | 0.25 to 2.0 |
| Witepsol H-15 base | 98.0 to 99.75 |
| DHEA suppositories were prepared using Witepsol H-15 base (Paddock Laboratories, Minneapolis, USA). Any other lipophilic base such as Hard Fat, Fattibase, Wecobee, cocoa butter, *theobroma* oil or other combinations of Witepsol bases could be used. | |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example G

The SERM and the sex steroid precursor are intravaginally administered while LHRH agonist is parenterally administered.

| Ingredient | Weight % (by weight of total composition) |
|---|---|
| Sex steroid precursor composition for intravaginal administration (suppository or ovule) | |
| DHEA | 0.25 to 2.0 |
| Witepsol H-15 base | 98.0 to 99.75 |
| + | |
| SERM composition for intravaginal administration (suppository or ovule) | |
| Acolbifene | 0.3 to 3.0 |
| Hard Fat | 97.0 to 99.7 |
| Acolbifene suppositories were prepared using Hard Fat (Witepsol). Any other bases such as Fattibase, Wecobee, cocoa butter, *theobroma* oil or other combinations of Hard Fat could be used. | |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example H

The SERM is orally administered and the sex steroid precursor is percutaneously administrated while LHRH agonist is parenterally administered.

| Ingredient | Weight % (by weight of total composition) |
|---|---|
| SERM composition for oral administration (capsules) | |
| Acolbifene | 5.0 |
| Lactose hydrous | 80.0 |
| Starch | 4.8 |
| Cellulose microcrystalline | 9.8 |
| Magnesium stearate | 0.4 |
| + | |
| Sex steroid precursor composition for percutaneous administration (gel) | |
| DHEA | 2.0 |
| Caprylic-capric Triglyceride (Neobee M-5) | 5.0 |
| Hexylene Glycol | 15.0 |
| Transcutol (diethyleneglycol monomethyl ether) | 5.0 |
| Benzyl alcohol | 2.0 |
| Cyclomethicone (Dow corning 345) | 5.0 |
| Ethanol (absolute) | 64.0 |
| Hydroxypropylcellulose (1500 cps) (KLUCEL) | 2.0 |
| or | |
| Sex steroid precursor composition for percutaneous administration (cream) | |
| | Formulation EM-760-48-1.0% |
| Cyclometicone | 5.0% |
| Light mineral oil | 3.0% |
| 2-ethylhexyl stearate | 10.0% |
| Cutina E24 | 1.0% |
| DC emulsifier 10 | 3.0% |
| BHT | 0.09% |
| Propyleneglycol | 46.01% |
| Ethanol 95 | 10.0% |
| DHEA | 1.0% |
| Eau purifiée | 15.0% |
| MgSO4 | 0.65% |
| Ethanol 95 | 5.25% |
| Total | 100.0% |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example I

The SERM is orally administered (capsules) while LHRH agonist is parenterally administered.

| Ingredient | Weight % (by weight of total composition) |
|---|---|
| SERM composition for oral administration (capsules) | |
| Acolbifene | 5.0 |
| Lactose hydrous | 80.0 |
| Starch | 4.8 |
| Cellulose microcrystalline | 9.8 |
| Magnesium stearate | 0.4 |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Example J

The SERM is orally administered (tablets) while LHRH agonist is parenterally administered.

| Ingredient | Weight % (by weight of total composition) |
|---|---|
| SERM composition for oral administration (tablets) | |
| Acolbifene | 5.0 |
| Gelatin | 5.0 |
| Lactose | 73.5 |
| Starch | 16.5 |
| + | |
| LHRH agonist for intramuscular depot injection | |
| Leuprolide acetate (Lupron depot ®-3 months) | 0.7 |
| Polylactic acid | 6.1 |
| D-mannitol | 5.8 |
| Carboxymethylcellulose sodium | 0.5 |
| Polysorbate 80 | 0.1 |
| Glacial acetic acid (USP) | to control pH |
| Water for injection (USP) | 86.8 |

Other SERMs (Toremifene, Ospemifene, Raloxifene, Arzoxifene, Lasofoxifene, Bazedoxifene acetate (TSE-424), ERA-923, GW 5638) may be substituted for Acolbifene in the above formulations, as well as other sex steroid precursors such as dehydroepiandrosterone sulfate (DHEA-S), 4-androstene-3,17-dione and androst-5-ene-3β,17β-diol (5-diol) may be substituted for DHEA. Other commercial LHRH agonist may be substituted for Leuprolide acetate. More than one SERM or more than one sex steroid precursor or more than one LHRH agonist or antagonist may be included in which case the combined weight percentage is preferably that of the weight percentage for the single sex steroid precursor or single SERM or single LHRH agonist given in the examples above.

The invention has been described in terms of preferred embodiments and examples, but is not limited thereby. Those of skill in the art will readily recognize the broader applicability and scope of the invention which is limited only by the patent claims herein.

What is claimed is:

1. A method for treating or reducing the likelihood of acquiring endometriosis comprising inhibiting ovarian hormonal secretion by administering to woman in need of said treatment or reduction a therapeutically effective amount of an LHRH antagonist selected from the group consisting of abarelix, teverelix, cetrorelix acetate, ganirelix acetate, iturelix, acyline, degarelix, ornirelix, azaline B, ozarelix, LXT-101, elagolix, TAK-013, TAK-385, and T-98475, and further comprising administering to said woman a therapeutically effective amount of a selective estrogen receptor modulator, wherein the selective estrogen receptor modulator is Acolbifene (EM-652.HCl, EM-1538) and a therapeutically effective amount of a sex steroid precursor, wherein the sex steroid precursor is dehydroepiandrosterone, wherein the selective estrogen receptor modulator acolbifene has no estrogenic activity on breast, uterine or endometrial tissues and is orally or percutaneously administered and wherein the method does not include administration of a sex hormone.

* * * * *